United States Patent
Diwu et al.

(10) Patent No.: US 8,105,829 B2
(45) Date of Patent: *Jan. 31, 2012

(54) FLUOROMETRIC ANALYSIS KIT

(75) Inventors: Zhenjun Diwu, Sunnyvale, CA (US);
Jianheng Zhang, Santa Clara, CA (US);
Yi Tang, Sunnyvale, CA (US); Xiang Guobing, Santa Clara, CA (US)

(73) Assignee: AnaSpec Incorporated, Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/925,505

(22) Filed: Oct. 21, 2010

(65) Prior Publication Data

US 2011/0045585 A1 Feb. 24, 2011

Related U.S. Application Data

(60) Continuation of application No. 12/287,071, filed on Oct. 6, 2008, now Pat. No. 7,820,783, which is a division of application No. 11/256,581, filed on Oct. 21, 2005, now Pat. No. 7,465,810.

(60) Provisional application No. 60/621,789, filed on Oct. 25, 2004.

(51) Int. Cl.
*C12N 5/071* (2010.01)
*C12N 1/20* (2006.01)
*C07D 487/14* (2006.01)
*C07K 2/00* (2006.01)
*C08H 1/00* (2006.01)
*C07H 99/00* (2006.01)
*C07H 19/00* (2006.01)
*C07H 21/00* (2006.01)

(52) U.S. Cl. ............ 435/325; 435/252.1; 530/300; 530/409; 536/18.7; 536/22.1; 536/23.1; 540/460

(58) Field of Classification Search ............ 435/252.1, 435/325; 540/460
See application file for complete search history.

(56) References Cited

U.S. PATENT DOCUMENTS

| | | | |
|---|---|---|---|
| 4,147,862 A | 4/1979 | Hayami et al. | |
| 4,314,058 A | 2/1982 | Hayami et al. | |
| 5,439,797 A | 8/1995 | Tsien et al. | |
| 6,074,834 A | 6/2000 | Slezak et al. | |
| 6,926,885 B2 * | 8/2005 | Licha et al. | 424/9.6 |

OTHER PUBLICATIONS

Wolf, David E., "Determination of the sidedness of carbocyanine dye labeling of membranes," Biochemistry (1985) vol. 24, pp. 582-585.
Chen, Ping, et al., "Structure and solvent effective on the photostability of indolenine cyanine dyes," Elsevier Science Ltd., Dyes and Pigments (1999) vol. 41, pp. 227-331.

* cited by examiner

*Primary Examiner* — Yong Chu
(74) *Attorney, Agent, or Firm* — Jeffrey A. McKinney, JD; McKinney Law Group APC

(57) ABSTRACT

Chemically reactive carbocyanine dyes that are intramolecularly crosslinked between the 1-position and 3'-position, their bioconjugates and their uses are described. 1,3'-crosslinked carbocyanines are superior to those of conjugates of spectrally similar 1,1'-crosslinked or non-crosslinked dyes. The invention includes derivative compounds having one or more benzo nitrogens.

10 Claims, 17 Drawing Sheets

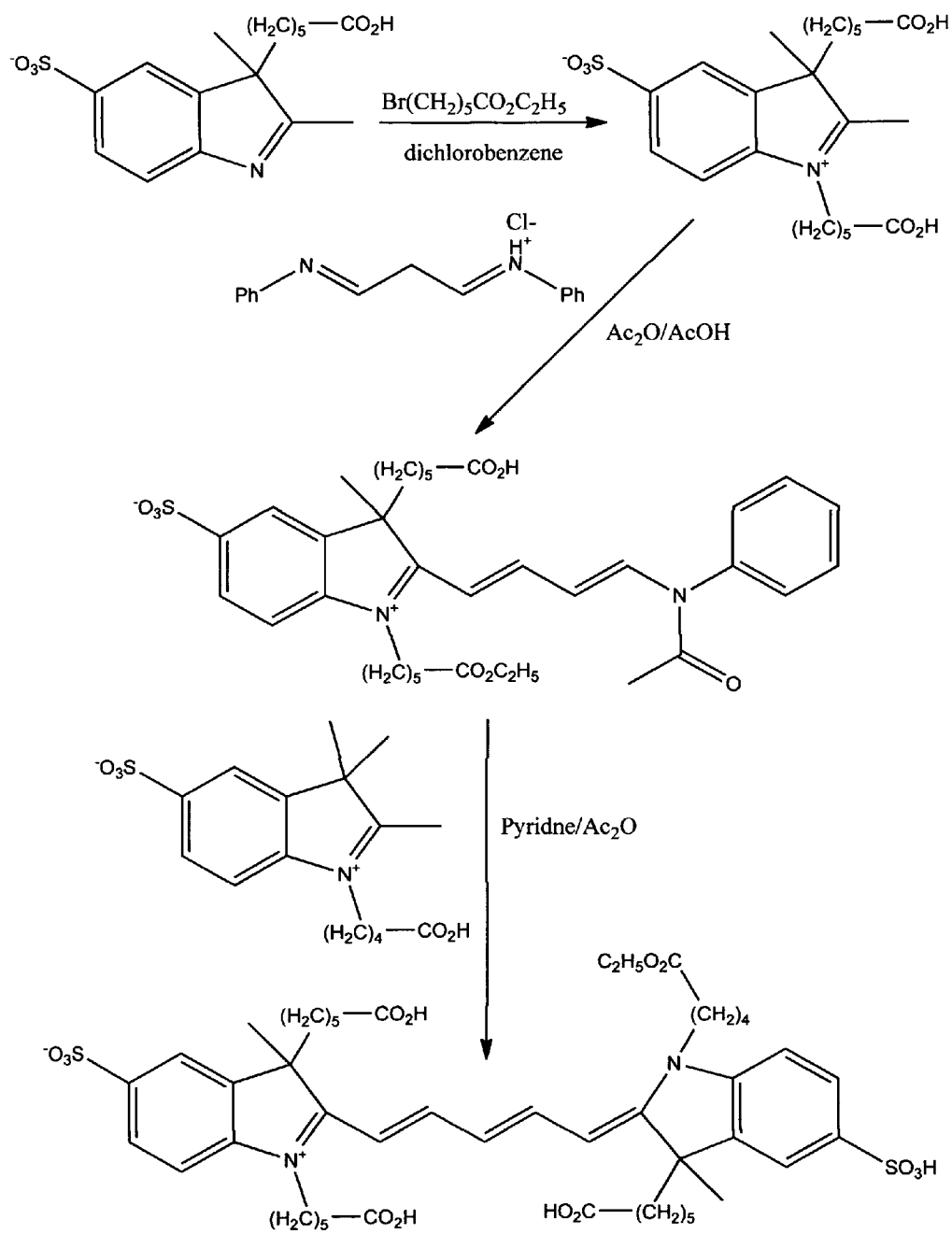
Figure 6 (1 of 2 pages)

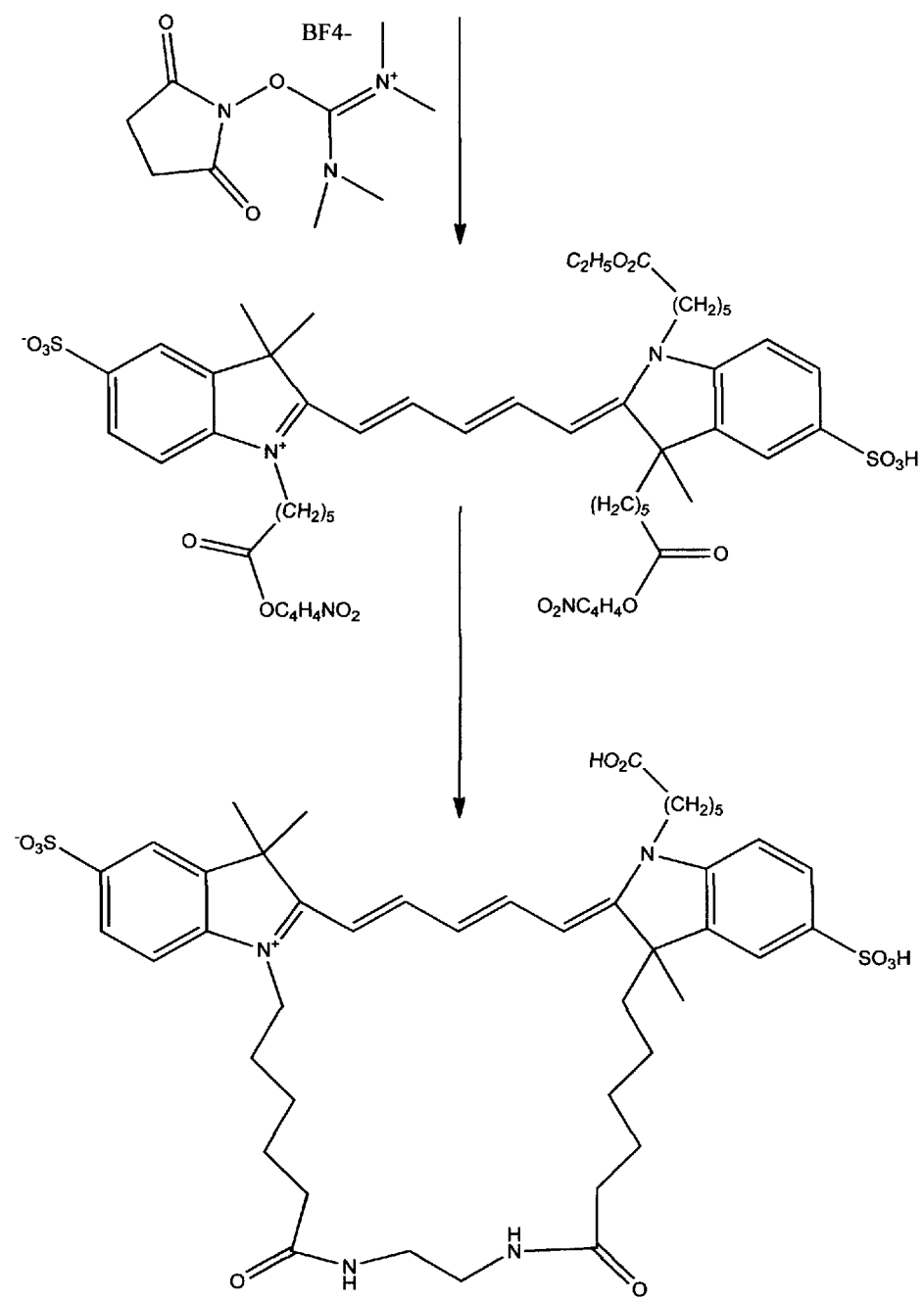
FIG. 6 (2 of 2 pages)

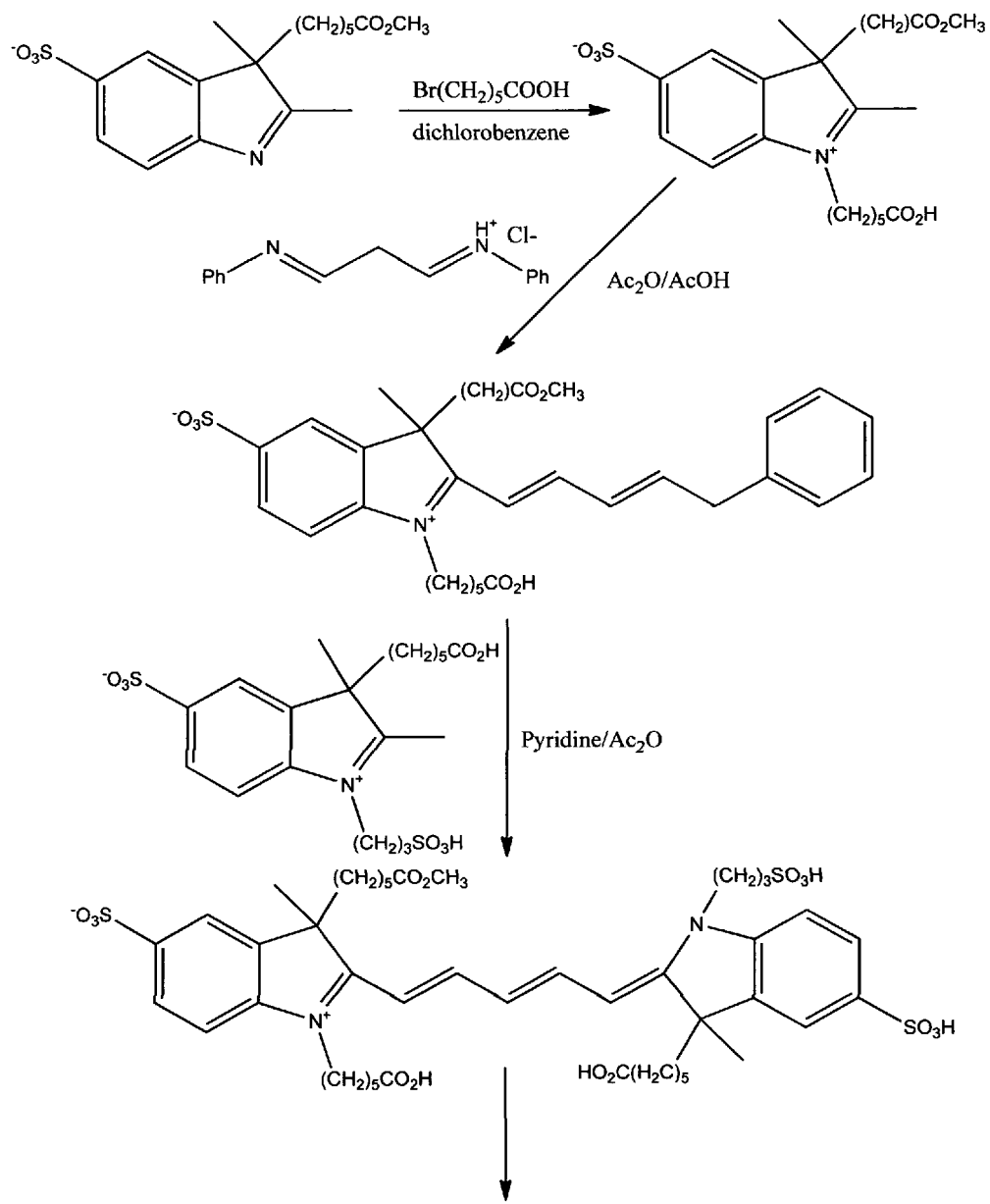
Figure 7 (1 of 2 pages)

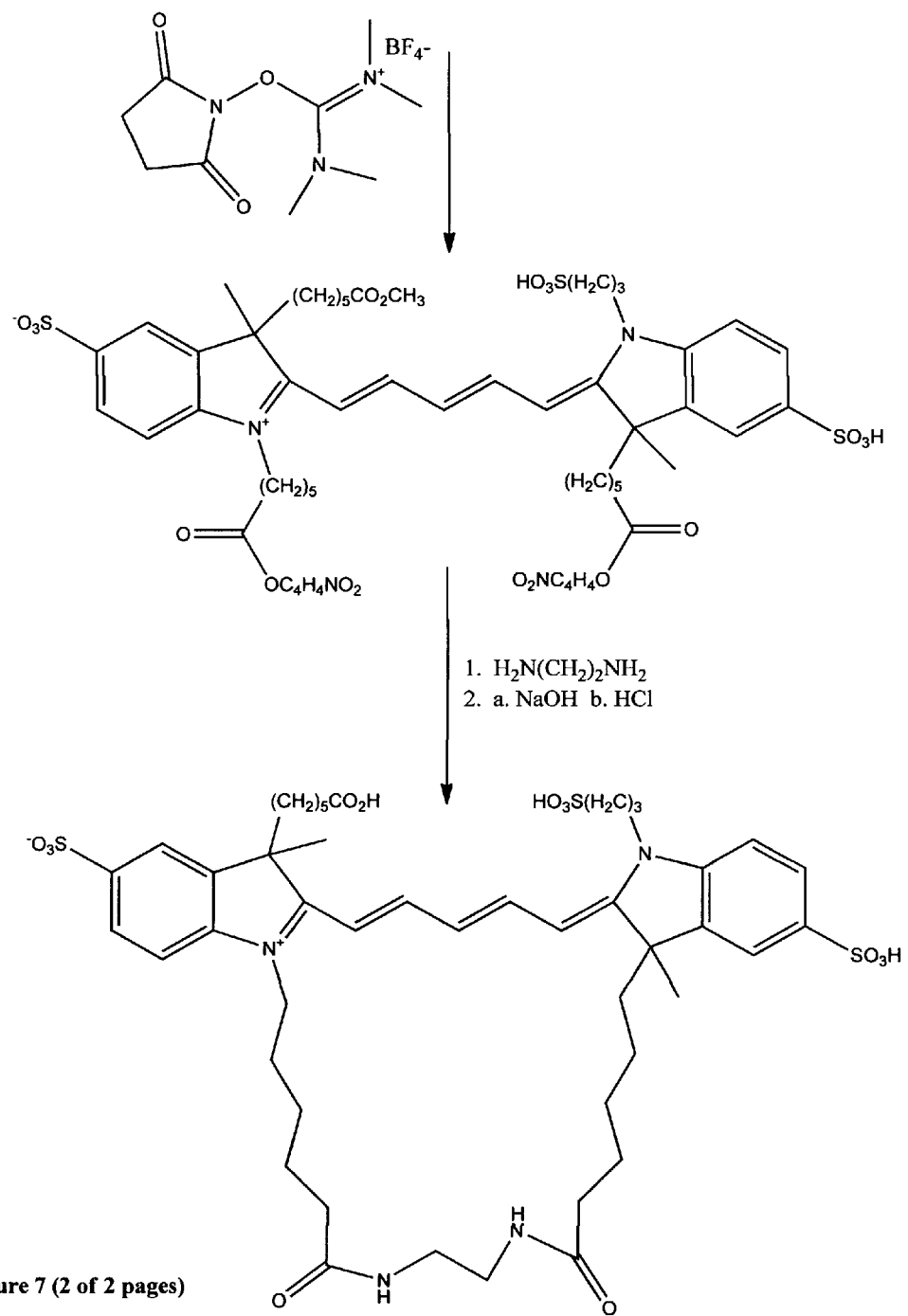
Figure 7 (2 of 2 pages)

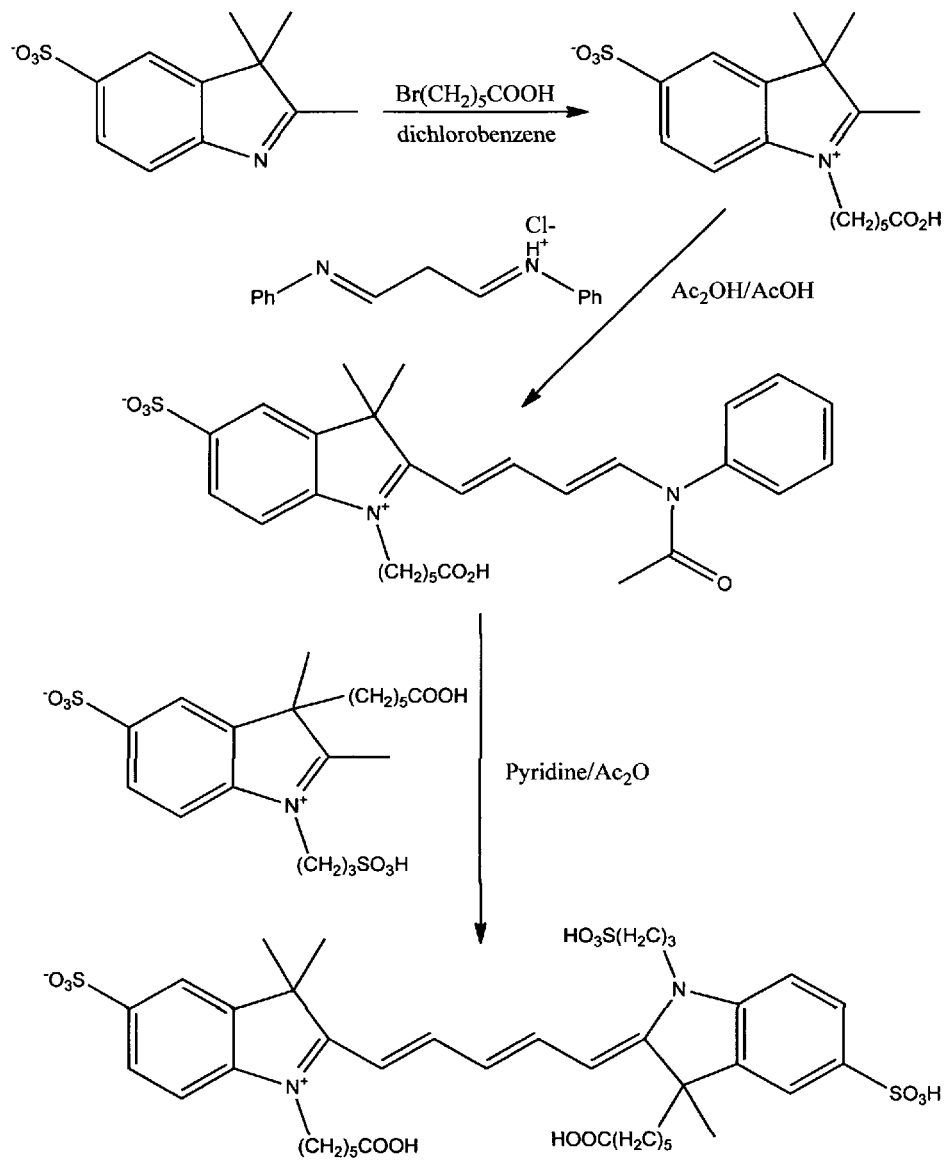
Figure 8 (1 of 2 pages)

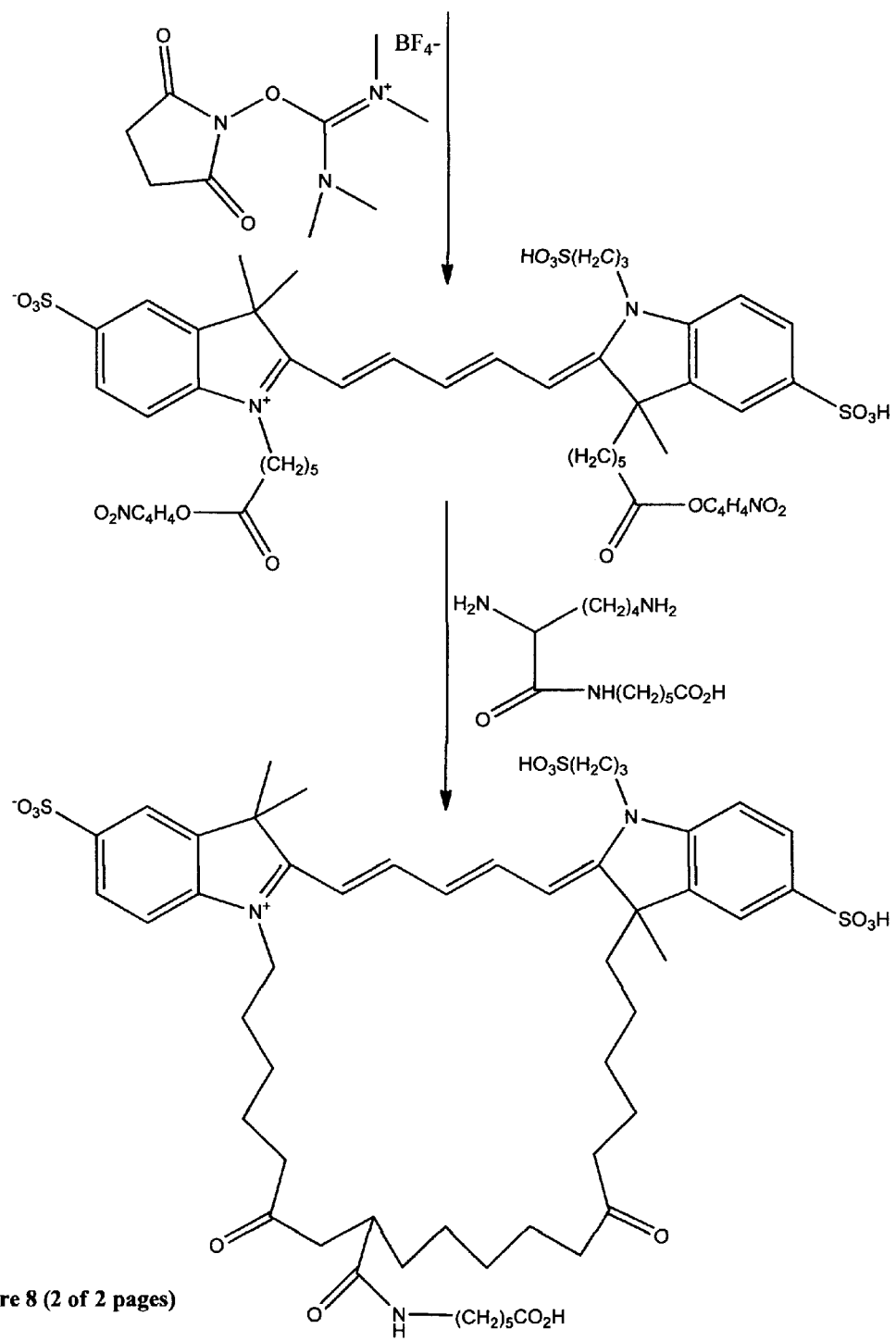
Figure 8 (2 of 2 pages)

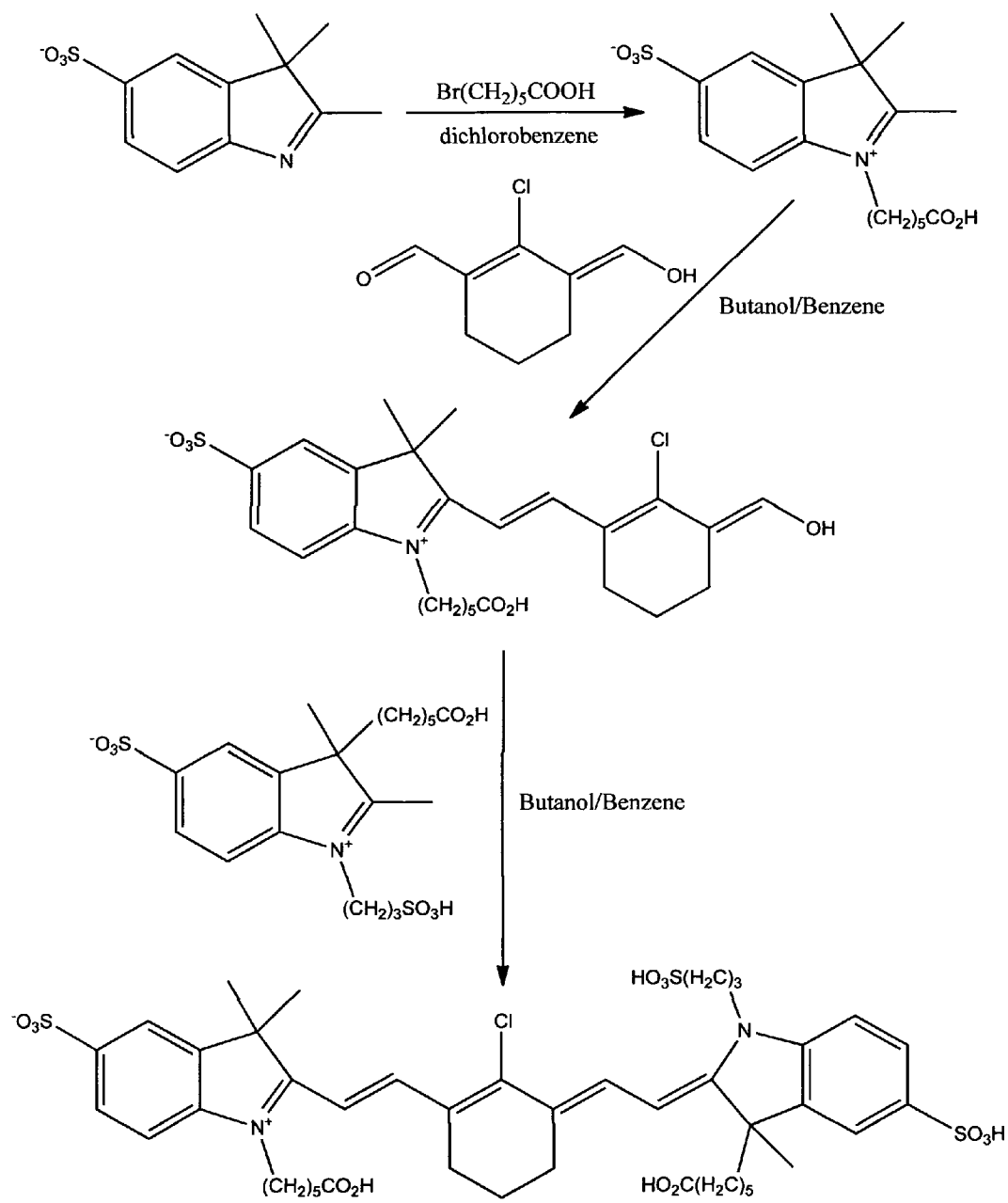
Figure 9 (1 of 2 pages)

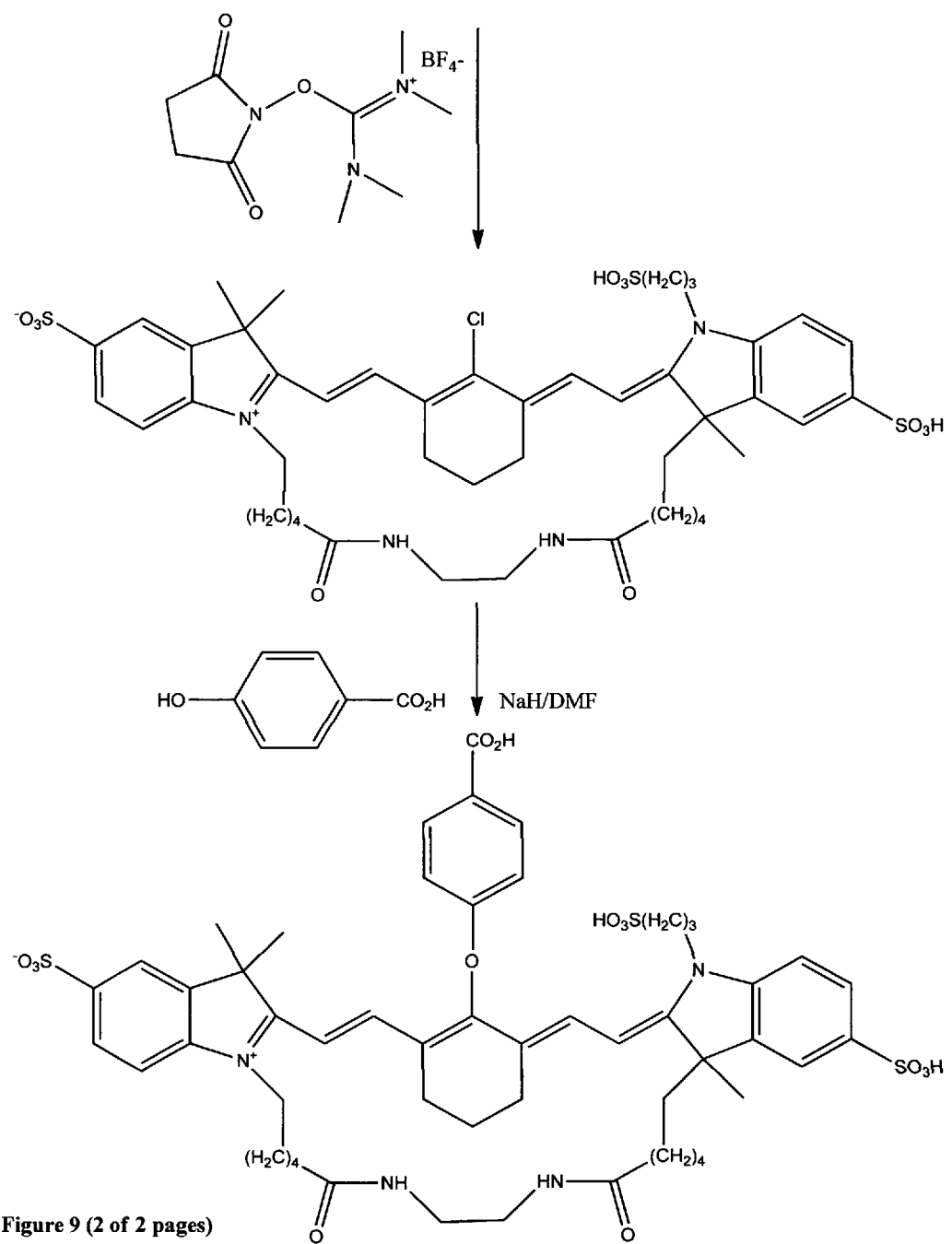
Figure 9 (2 of 2 pages)

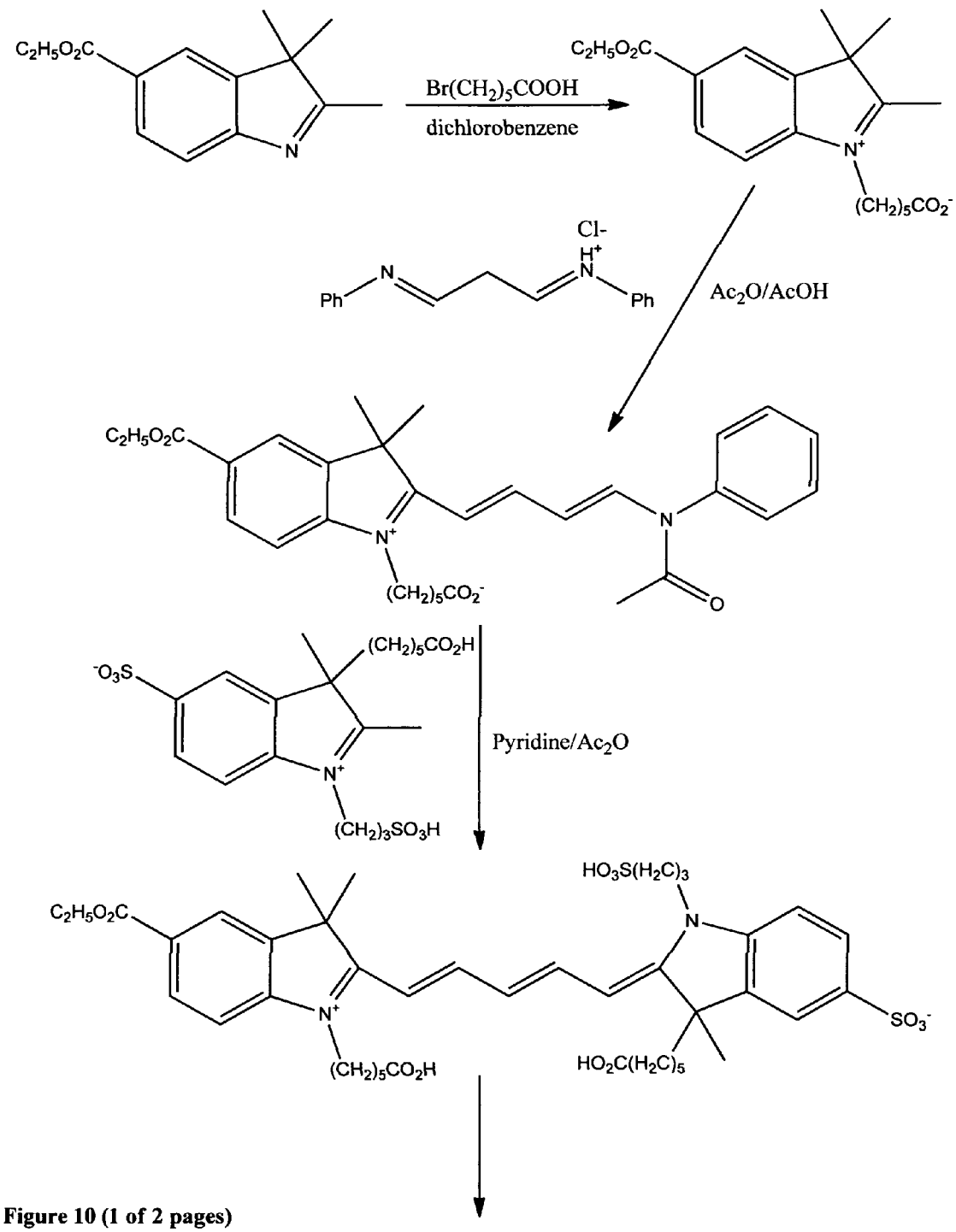
Figure 10 (1 of 2 pages)

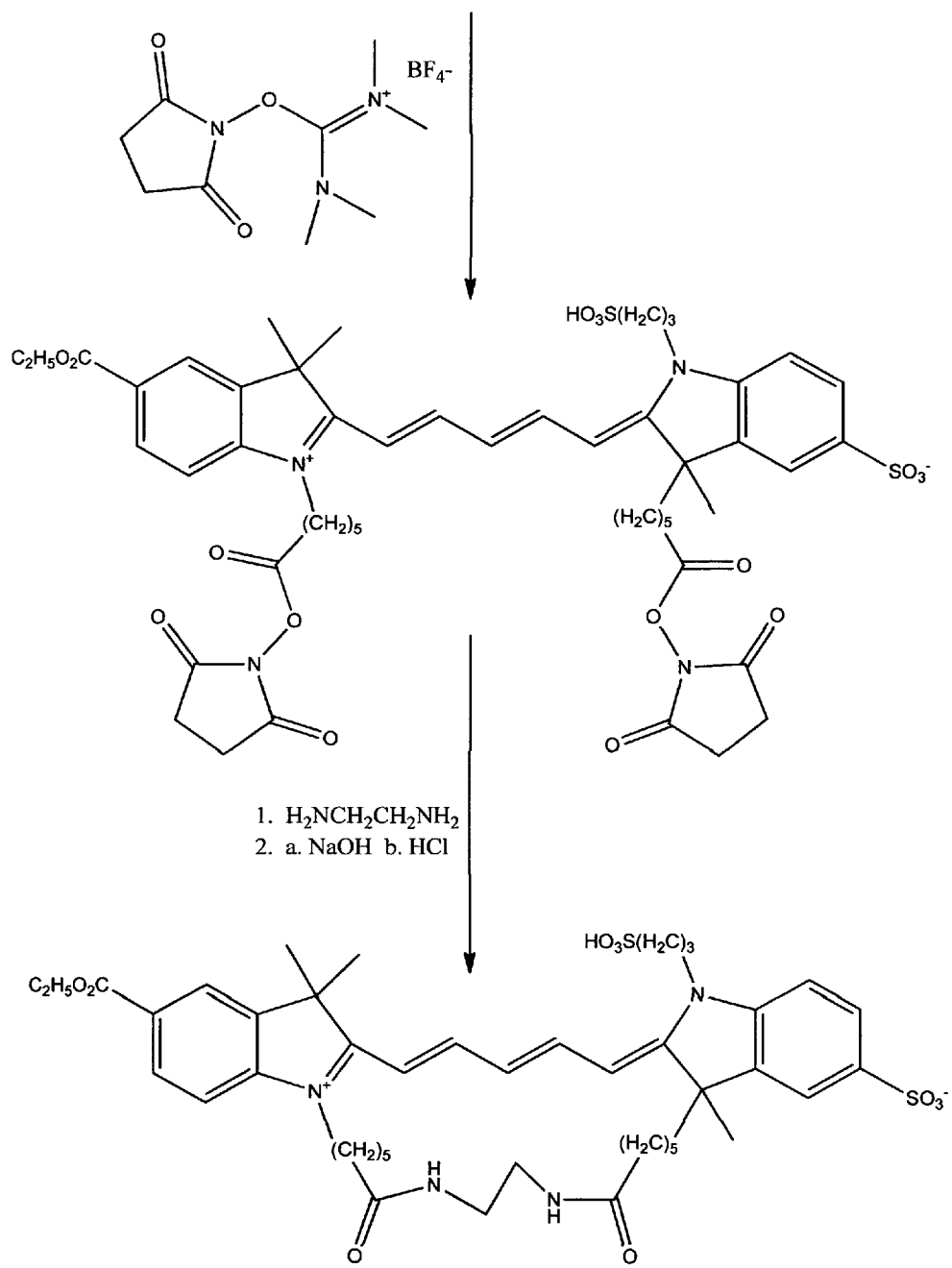
Figure 10 (2 of 2 pages)

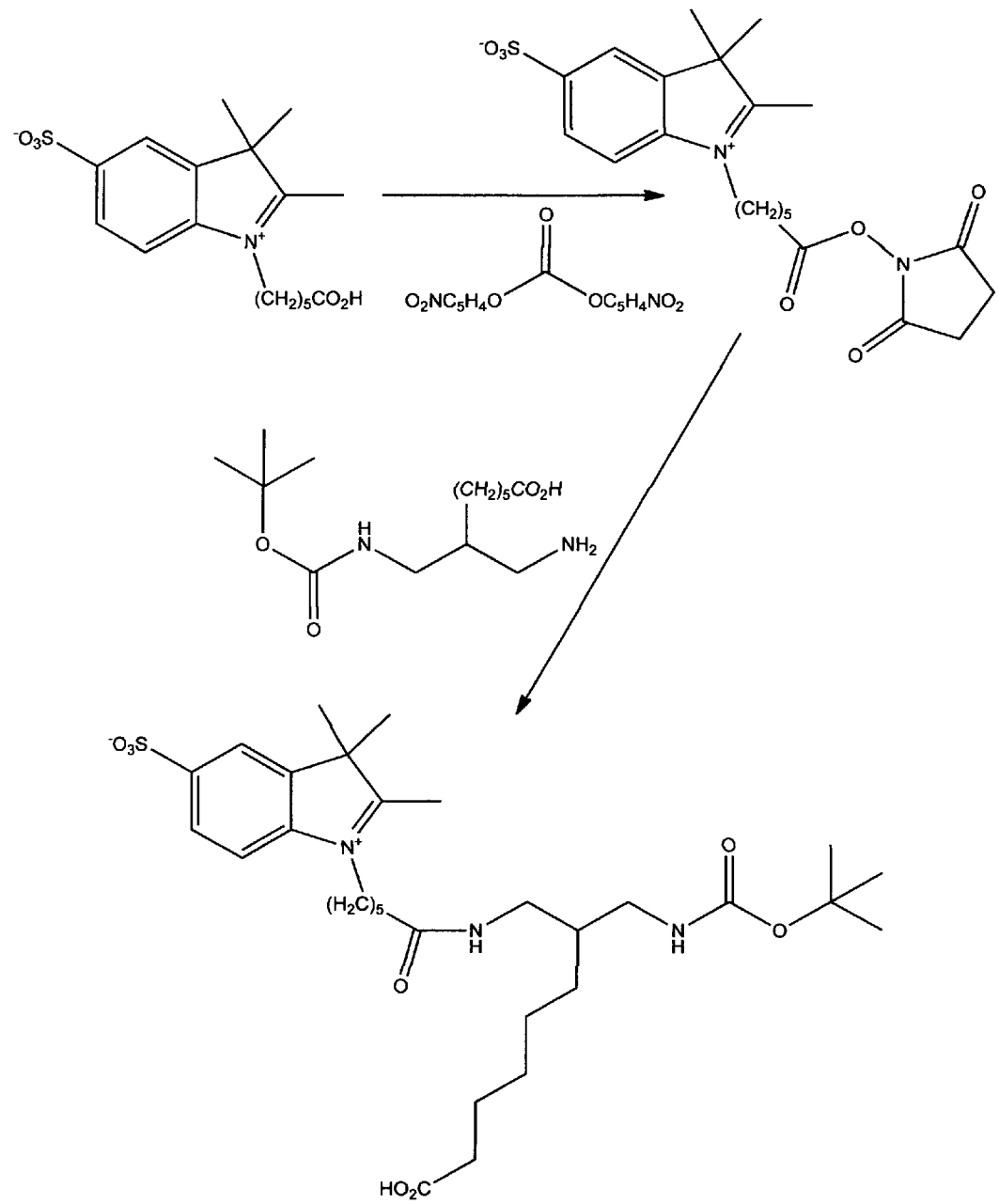
Figure 11 (1 of 2 pages)

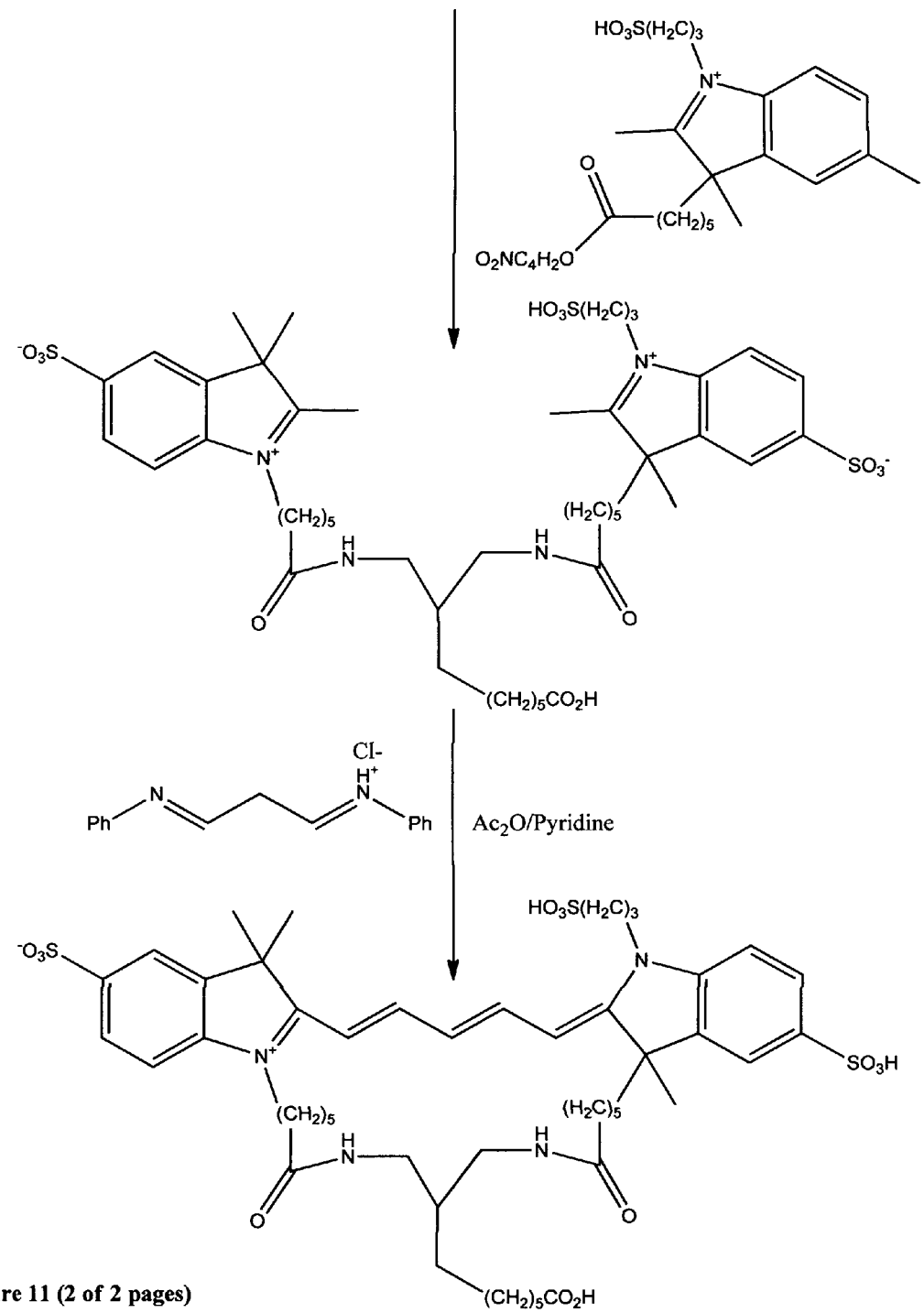
Figure 11 (2 of 2 pages)

FLUOROMETRIC ANALYSIS KIT

CROSS-REFERENCE TO RELATED APPLICATION

This application is a continuation application of, and accordingly claims priority from, U.S. patent application Ser. No. 12/287,071, filed Oct. 6, 2008, now U.S. Pat. No. 7,820,783 which is a divisional application off of U.S. patent application Ser. No. 11/256,581, filed Oct. 21, 2005, now U.S. Pat. No.7,465,810 which claims the benefit of U.S. Provisional Patent Application Ser. No. 60/621,789, filed Oct. 25, 2004, the entire disclosures of which are incorporated by reference into this document.

FIELD OF THE INVENTION

The invention relates to fluorescent chemicals, including reactive dyes and dye-conjugates; and to their uses.

BACKGROUND OF THE INVENTION

Luminescent probes are valuable reagents for the analysis and separation of molecules and cells and for the detection and quantification of other materials. A very small number of luminescent molecules can be detected under optimal circumstances. Barak and Webb visualized fewer than 50 fluorescent lipid analogs associated with the LDL reception of cells using a SIT camera, J. CELL BIOL., 90, 595-604 (1981). Flow cytometry can be used to detect fewer than 10,000 fluorescein molecules associated with particles or certain cells (Muirhead, Horan and Poste, BIOTECHNOLOGY, 3, 337-356 (1985)). Some specific examples of the application of fluorescent probes are (1) identification and separation of subpopulations of cells in a mixture of cells by the techniques of fluorescence flow cytometry, fluorescence-activated cell sorting and fluorescence microscopy; (2) determination of the concentration of a substance that binds to a second species (e.g., antigen-antibody reactions) in the technique of fluorescence immunoassay; (3) localization of substances in gels and other insoluble supports by the techniques of fluorescence staining. These techniques are described by Herzenberg, et al., "CELLULAR IMMUNOLOGY" 3rd ed., Chapter 22; Blackwell Scientific Publications (1978); and by Goldman, "FLUORESCENCE ANTIBODY METHODS", Academic Press, New York, (1968); and by Taylor, et al., APPLICATIONS OF FLUORESCENCE IN THE BIOMEDICAL SCIENCES, Alan Liss Inc., (1986).

When employing fluorescent dyes for the above purposes, there are many constraints on the choice of the fluorescent dye. One constraint is the absorption and emission characteristics of the fluorescent dye, since many ligands, receptors, and materials in the sample under test, e.g. blood, urine, cerebrospinal fluid, will fluoresce and interfere with an accurate determination of the fluorescence of the fluorescent label. This phenomenon is called autofluorescence or background fluorescence. Another consideration is the ability to conjugate the fluorescent dye to ligands and receptors and other biological and non-biological materials and the effect of such conjugation on the fluorescent dye. In many situations, conjugation to another molecule may result in a substantial change in the fluorescent characteristics of the fluorescent dye and, in some cases, substantially destroy or reduce the quantum efficiency of the fluorescent dye. It is also possible that conjugation with the fluorescent dye will inactivate the function of the molecule that is labeled. A third consideration is the quantum efficiency of the fluorescent dyes which should be high for sensitive detection. A fourth consideration is the light absorbing capability, or extinction coefficient, of the fluorescent dyes, which should also be as large as possible. Also of concern is whether the fluorescent molecules will interact with each other when in close proximity, resulting in self-quenching. An additional concern is whether there is non-specific binding of the fluorescent dyes to other compounds or container walls, either by themselves or in conjunction with the compound to which the fluorescent dye is conjugated.

The applicability and value of the methods indicated above are closely tied to the availability of suitable fluorescent compounds. In particular, there is a need for fluorescent substances that emit in the longer wavelength region (yellow to near infrared), since excitation of these chromophores produces less autofluorescence and also multiple chromophores fluorescing at different wavelengths can be analyzed simultaneously if the full visible and near infrared regions of the spectrum can be utilized. Fluorescein, a widely used fluorescent compound, is a useful emitter in the green region although in certain immunoassays and cell analysis systems background autofluorescence generated by excitation at fluorescein absorption wavelengths limits the detection sensitivity. However, the conventional red fluorescent label rhodamine has proved to be less effective than fluorescein.

Phycobiliproteins have made an important contribution because of their high extinction coefficient and high quantum yield. These chromophore-containing proteins can be covalently linked to many proteins and are used in fluorescence antibody assays in microscopy and flow cytometry. The phycobiliproteins have the disadvantages that (1) the protein labeling procedure is relatively complex; (2) the protein labeling efficiency is not usually high (typically an average of 0.5 phycobiliprotein molecules per protein); (3) the phycobiliproteins are natural products and their preparation and purification are complex; (4) the phycobiliproteins are expensive; (5) there are at present no phycobiliproteins available as labeling reagents that fluoresce further to the red region of the spectrum than allophycocyanine, which fluoresces maximally at 680 nm; (6) the phycobiliproteins are large proteins with molecular weights ranging from 33,000 to 240,000 and are larger than many materials that are desirable to label, such as metabolites, drugs, hormones, derivatized nucleotides, and many proteins including antibodies. The latter disadvantage is of particular importance because antibodies, avidin, DNA-hybridization probes, hormones, and small molecules labeled with the large phycobiliproteins may not be able to bind to their targets because of steric limitations imposed by the size of the conjugated complex.

Other techniques involving histology, cytology, immunoassays would also enjoy substantial benefits from the use of a fluorescent dye with a high quantum efficiency, absorption and emission characteristics at longer wavelengths, having simple means for conjugation and being substantially free of nonspecific interference.

Fluorescent compounds are covalently or noncovalently attached to other materials to impart color and fluorescence. Brightly fluorescent dyes permit detection or location of the attached materials with great sensitivity. Certain carbocyanine dyes have demonstrated utility as labeling reagents for a variety of biological applications, e.g. U.S. Pat. No. 4,981,977 to Southwick, et al. (1991); U.S. Pat. No. 5,268,486 to Waggoner, et al. (1993); U.S. Pat. No. 5,569,587 to Waggoner (1996); U.S. Pat. No. 5,569,766 to Waggoner, et al. (1996); U.S. Pat. No. 5,486,616 to Waggoner, et al. (1996); U.S. Pat. No. 5,627,027 to Waggoner (1997); U.S. Pat. No. 5,808,044 to Brush, et al. (1998); U.S. Pat. No. 5,877,310 to Redding-ton, et al. (1999); U.S. Pat. No. 6,002,003 to Shen, et al. (1999); U.S. Pat. No. 6,004,536 to Leung, et al. (1999); U.S. Pat. No. 6,008,373 to Waggoner, et al. (1999); U.S. Pat. No. 6,043,025 to Minden, et al. (2000); U.S. Pat. No. 6,127,134 to Minden, et al. (2000); U.S. Pat. No. 6,130,094 to Waggoner, et al. (2000); U.S. Pat. No. 6,133,445 to Waggoner, et al. (2000); also WO 97/40104, WO 99/51702, WO 01/21624, and EP 1 065 250 A1; and TETRAHEDRON LETT., 41, 9185-88 (2000). Nevertheless, many carbocyanine dyes are known to share certain disadvantages, e.g. severe quenching of the fluorescence of carbocyanine dyes in biopolymer conjugates, e.g. quenching of Cy5 and Cy7 dye variants on conjugates, as discussed by Gruber, et al., BIOCONJUGATE CHEM., 11, 696 (2000), and in EP 1 065 250 A1, 0004. In addition, certain desired sulfoalkyl derivatives of the reactive carbocyanine dyes are difficult to prepare, as indicated for Cy3 and Cy5 variants by Waggoner and colleagues in BIO-CONJUGATE CHEM., 4, 105, 109 (1993). Cyanine dyes also have a very strong tendency to self-aggregate (i.e. stack), which can significantly reduce the fluorescence quantum yields, as described in the extensive review by Mishra, et al., CHEM. REV., 100, 1973 (2000).

Another problem with the existing carbocyanine labeling dyes is the free rotation/vibration of two indolium (or benzothiazolium, or benzoimidazolium) heads around the middle conjugated double bonds that significantly reduce their fluorescence intensities (see Scheme 1). This phenomenon is called 'loose belt effect' that is described in "MODERN MOLECULAR PHOTOCHEMISTRY", Chapters 5 and 6, University Science Books, Sausalito, Calif., authored by Nicholas J. Turro (1991).

Scheme 1. 'Loose Belt Effect' through vibration and rotation around the middle conjugated double bonds

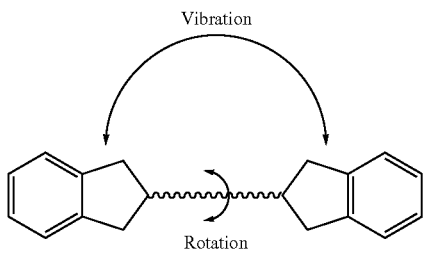

This so-called 'loose belt effect' can be eliminated by the crosslinking of the two heads. 1,1'-crosslinking of cyanines is disclosed by R. Singh, et al. WO 01/02374 (2001), which is supposed to eliminate the 'loose belt effect' described above. However, we observe that the 1,1'-crosslinking actually causes the decreased fluorescence quantum yield of dye-protein conjugates compared to that of non-crosslinked carbocyanineprotein conjugates at the similar ratios of dye/protein (see FIG. 3). This unfavorable fluorescence quantum decrease might be caused by the inappropriate stereochemistry of 1,1'-crosslinking.

BRIEF DESCRIPTION OF THE DRAWINGS

FIG. 6. Synthesis of a cyanine that has a RGM at 1-position.

FIG. 7. Synthesis of a cyanine that has a RGM at 3'-position.

FIG. 8. Synthesis of a cyanine that has a RGM at the non-conjugated Chain C.

FIG. 9. Synthesis of a cyanine that has a RGM at the conjugated double bondbridge.

FIG. 10. Synthesis of a cyanine that has a RGM at Ring A or Ring B.

FIG. 11. Synthesis of a cyanine through intramolecular coupling.

SUMMARY OF INVENTION AND DESCRIPTION OF PREFERRED EMBODIMENTS

Figure 1:
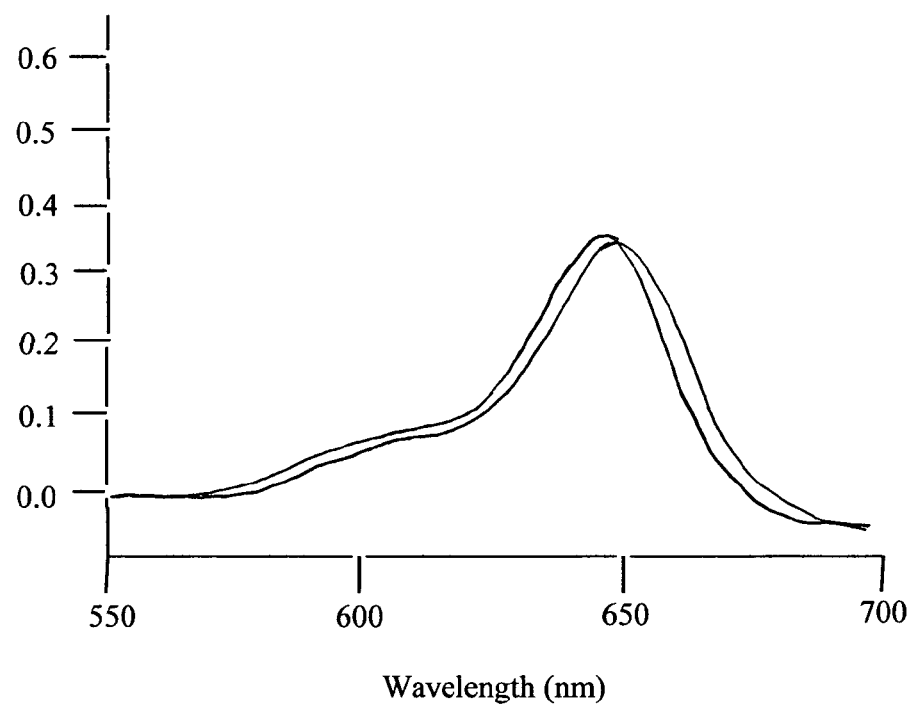
FIG. 1. Absorption spectra of Cy5 free acid (from Amersham Biosciences) and Compound 13 in PBS buffer (pH=7.4). Absorption characteristics of the Compound 13 are similar to those of Cy5, when present as the free-acid.
Figure 2:
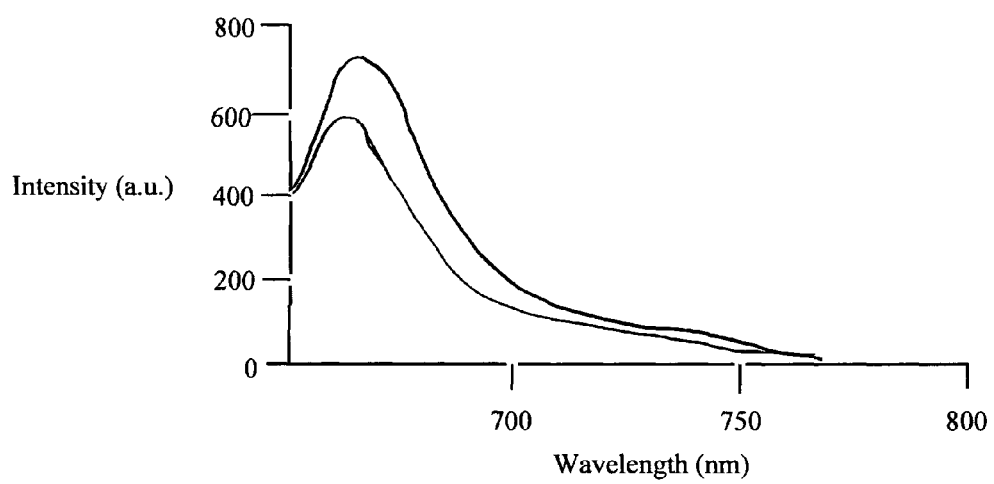
FIG. 2. Fluorescence spectra of Cy5 free acid (from Amersham Biosciences) and Compound 13 in PBS buffer (pH=7.4, excited at 630 nm). Fluorescence characteristics of the Compound 13 are similar to those of Cy5, when present as the free-acid.
Figure 3:
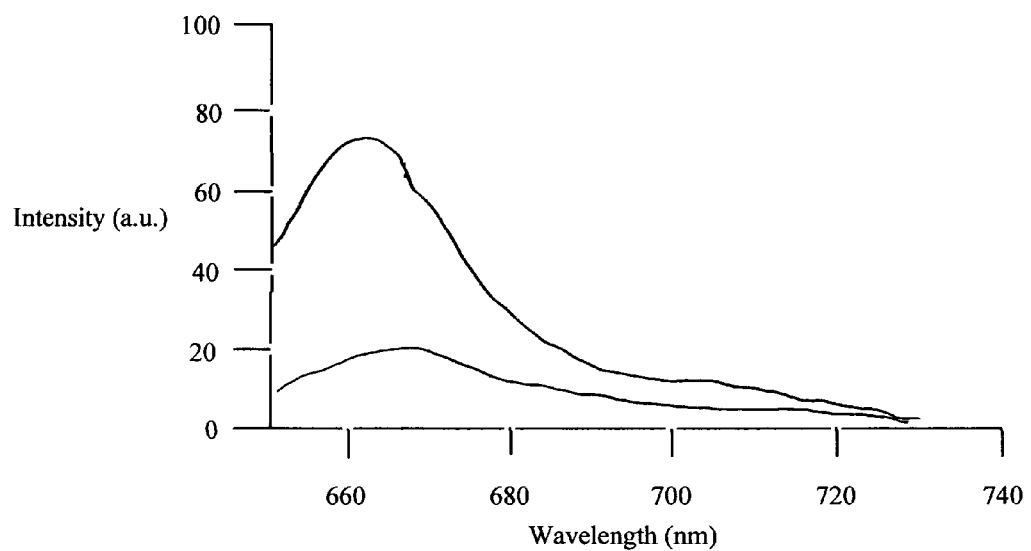
FIG. 3. Comparison of fluorescence quantum yields of Cy5 SE and Compound 38 when conjugated to goat anti-rabbit IgG (GAR). The conjugates are prepared and characterized as described in Examples 58.
Figure 4:
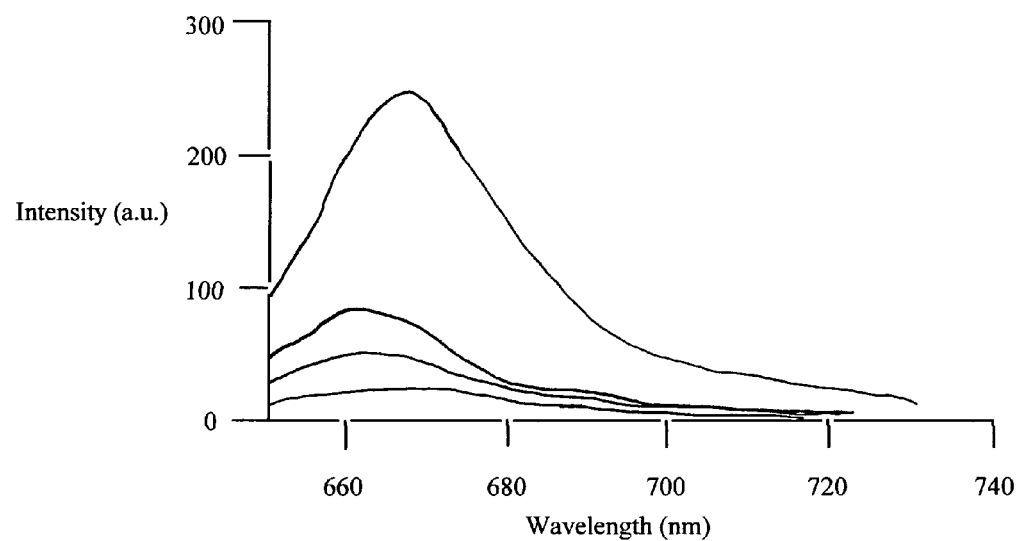
FIG. 4. Comparison of fluorescence quantum yields of Cy5 SE and Compounds 14 and 38 when conjugated to goat anti-rabbit IgG (GAR). The conjugates are prepared and characterized as described in Examples 58.

We discovered that 1,3'-crosslinking of an carbocyanine dye unexpectedly mitigates problems discussed in the background section and results in dye-polymer conjugates that are substantially more fluorescent on proteins, nucleic acids and other biopolymers, than conjugates labeled with structurally similar 1,1'-crosslinked carbocyanine or noncrosslinked dyes (see FIG. 4). The enhanced fluorescence intensity of dye-biomolecule conjugates of the invention results in greater assay sensitivity. The increase in fluorescence quantum yields may result from the reduction of the ground state aggregation caused by the sterohindrance of 1,3'-crosslinking of an carbocyanine dye. This intramolecular 1,3'-crosslinking might also reduce the oxidative dimerization of carbocyanines, and thus decrease their sensitivity to ozone (see T. Katoh, et al. BULL. CHEM. SOC. JPN., 70, 1109-1114 (1997)). The increased ozone resistance provides a great advantage for their applications of the claimed dyes in microarrays. The ozone sensitivity of carbocyanines has been a serious problem for the microarray applications of Cy3, Cy5 and their analogs.

Scheme 2. Oxidative dimerization of carbocyanines

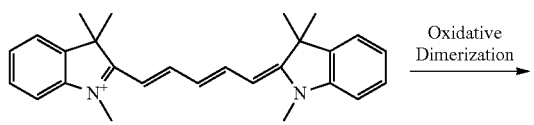

-continued

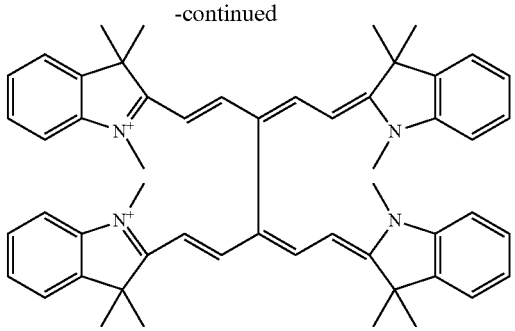

In addition to having more intense fluorescence emission than structurally similar cyanine dyes at similar wavelengths, and decreased artifacts in their absorption spectra upon conjugation to biopolymers, certain embodiments of the invention also have greater photostability (see FIG. 5) and higher absorbance (extinction coefficients) at the wavelength(s) of peak absorbance than such structurally similar dyes. The enhanced photostability might also be related to the reduction of oxidative dimerization. These improvements result in significantly greater sensitivity in assays that use these dyes and their conjugates, while utilizing existing filters and instrumentation already commercially available for use with similar dyes such as Cy3, Cy5, Cy5.5 and Cy7.

Furthermore, the dyes of the invention typically exhibit absorbance maxima between about 530 nm and about 800 nm, so these dyes can be selected to match the principal emission lines of the mercury arc lamp (546 nm), frequency-doubled Nd-Yag laser (532 nm), Kr-ion laser (568 nm and 647 nm). HeNe laser (543 nm, 594 nm, and 633 nm) or long-wavelength laser diodes (especially 635 nm and longer). Some dyes of the invention exhibit very long wavelength excitation (at least 640 nm, but some greater than about 730 nm) and emission bands (at least 665 nm, and some greater than about 750 nm), so they are particularly useful for samples that are transparent to infrared wavelengths.

The present invention comprises reactive 1,3'-crosslinked carbocyanine dyes and their conjugates. The dyes and dye conjugates are used to locate or detect the interaction or presence of analytes or ligands in a sample. Kits incorporating such dyes or dye conjugates facilitate their use in such methods.

The dyes of the invention typically have Formula I:

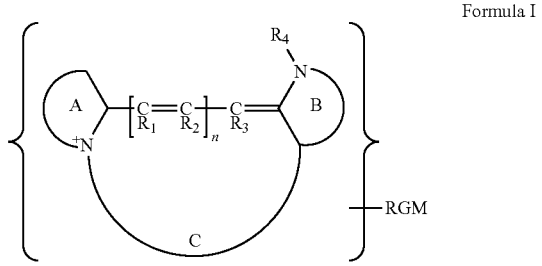

Formula I wherein rings A and B represent the atoms necessary to form a nitrogen-containing five-membered heterocyclic ring that has zero to three fused aromatic rings; and each said fused aromatic ring selected from the group consisting of C, CH, C(alkyl), O, S, N(aryl) and N(alkyl), and said five-membered ring contains =N(alkyl) coupled to the bridged and conjugated double bonds, and said aromatic rings are optionally substituted one or more times by substituents selected from the group consisting of a hydrogen, an alkyl having 1-20 carbons, a hydroxy, an alkoxy having 1-20 carbons, a trifluoromethyl, a halogen, a methylthio, a sulfonyl, a carbonyl, a hydroxy, an amino, a thiol, a sulfate, a phosphonate or a RGM C is a non-conjugated chain of 10-50 linear atoms selected from carbon, nitrogen, oxygen, phosphorus and sulfur that are further substituted by a hydrogen, an alkyl having 1-20 carbons, a hydroxy, an alkoxy having 1-20 carbons, a trifluoromethyl, a halogen, a methylthio, a sulfonyl, a carbonyl, a hydroxy, an amino, an alkylamino, an arylamino, a thiol, a sulfite, a phosphonate or a RGM.

n is 0 to 3.

$R_1$, $R_2$, $R_3$ and $R_4$ are independently-selected from the group consisting of a hydrogen, an alkyl having 1-20 carbons, a cycloalkyl having 3-20 carbons, an aryl, a heteroaryl, an amino, an alkylamino, an arylamino, a thiol and a RGM.

RGM is a chemically reactive group described below.

The dyes of the invention comprise a cyanine dye that contains: 1) a RGM group; and 2) a bridged and non-conjugated chain C that intramolecularlly crosslinks position 1 (ring A) with position 3' (ring B). In one embodiment of the invention, the first or second ring system is substituted by aside chain at position 1 that contains a RGM group. In another embodiment, the first or second ring contains a RGM group directly located on the aromatic rings (A or B). In another embodiment, the bridged methine is substituted by a side chain that contains a RGM group. In another embodiment, the bridged and non-conjugated chain C is substituted by a side chain that contains a RGM group. In another embodiment, the carbon atom at position 3 or 3' is substituted by a side chain that contains a RGM group.

Preferred compounds have at least one substituted indolium ring system wherein the substituent contains a RGM and a non-conjugated bridged chain. Other preferred compounds incorporate at least a charged group (e.g., sulfonate and ammonium moieties) to increase water solubility. By "sulfo" is meant sulfonic acid, or salt of sulfonic acid (sulfonate). Similarly, by "carboxy" is meant carboxylic acid or salt of carboxylic acid. "phosphate", as used herein, is an ester of phosphoric acid, and includes salts of phosphate. "phosphonate", as used herein, means phosphoric acid and includes salts of phosphonate. As used herein, unless otherwise specified, the alkyl portions of substituents such as alkyl, alkoxy, arylalkyl, alkylamino, dialkylamino, trialkylammonium, or perfluoroalkyl are optionally saturated, unsaturated, linear or branched, and all alkyl alkoxy, alkylamino, and dialkylamino substituents are themselves optionally further substituted by carboxy, sulfo, amino, or hydroxy.

A preferred embodiment is a compound of Formula II:

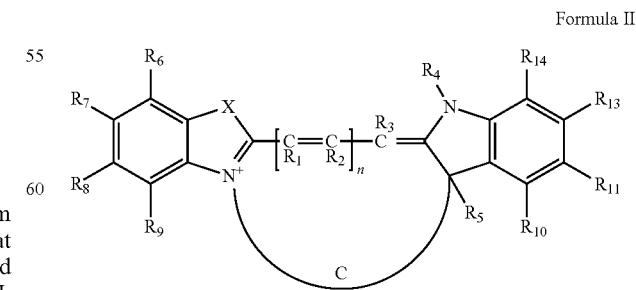

Formula II wherein C is a non-conjugated chain of 10-50 linear atoms selected from carbon, nitrogen, oxygen, phosphorus and sulfur that are further substituted by a hydrogen, an alkyl having 1-20 carbons, an alkoxy having 1-20 carbons, a trifluoromethyl, a halogen, a methylthio, a sulfonyl, a carbonyl, a hydroxy, an amino, a thiol or a RGM. $R_1$ to $R_{16}$ are a hydrogen, an alkyl having 1-20 carbons, an alkoxy having 1-20 carbons, a trifluoromethyl, a halogen, a methylthio, a sulfonyl, a carbonyl, a hydroxy, an amino, a thiol or a RGM; X is O, S, Se, $NR_{15}$ or $CR_{15}R_{16}$; n is 0 to 3.

Another preferred embodiment is a compound of Formula III:

Formula III

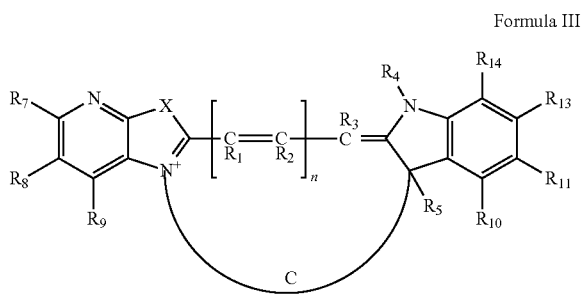

wherein C is a non-conjugated chain of 10-50 linear atoms selected from carbon, nitrogen, oxygen, phosphorus and sulfur that are further substituted by a hydrogen, an alkyl having 1-20 carbons, an alkoxy having 1-20 carbons, a trifluoromethyl, a halogen, a methylthio, a sulfonyl, a carbonyl, a hydroxy, an amino, a thiol or a RGM. $R_1$ to $R_{16}$ are a hydrogen, an alkyl having 1-20 carbons, an alkoxy having 1-20 carbons, a trifluoromethyl, a halogen, a methylthio, a sulfonyl, a carbonyl, a hydroxy, an amino, a thiol or a RGM; X is O, S, Se, $NR_{15}$, $CR_{15}R_{16}$; n is 0 to 3.

Another preferred embodiment is a compound of Formula IV:

Formula IV

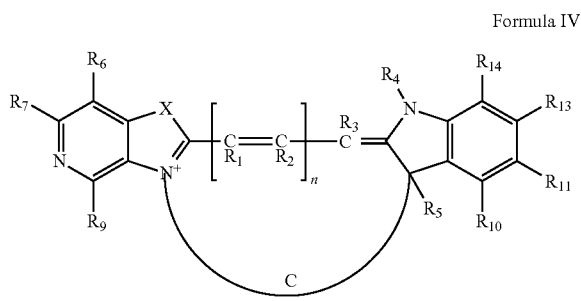

wherein C is a non-conjugated chain of 10-50 linear atoms selected from carbon, nitrogen, oxygen, phosphorus and sulfur that are further substituted by a hydrogen, an alkyl having 1-20 carbons, an alkoxy having 1-20 carbons, a trifluoromethyl, a halogen, a methylthio, a sulfonyl, a carbonyl, a hydroxy, an amino, a thiol or a RGM. $R_1$ to $R_{16}$ are a hydrogen, an alkyl having 1-20 carbons, an alkoxy having 1-20 carbons, trifluoromethyl, a halogen, a methylthio, a sulfonyl, a carbonyl, a hydroxyl, an amino, a thiol or a RGM; X is O, S, Se, $NR_{15}$, $CR_{15}R_{16}$; n is 0 to 3.

Another preferred embodiment is a compound of Formula V:

Formula V

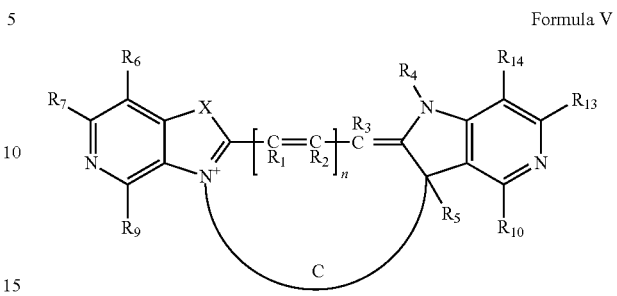

wherein C is a non-conjugated chain of 10-50 linear atoms selected from carbon, nitrogen, oxygen, phosphorus and sulfur that are further substituted by a hydrogen, an alkyl having 1-20 carbons, an alkoxy having 1-20 carbons, a trifluoromethyl, a halogen, a methylthio, a sulfonyl, a carbonyl, a hydroxy, an amino, a thiol or a RGM. $R_1$ to $R_{16}$ are a hydrogen, an alkyl having 1-20 carbons, an alkoxy having 1-20 carbons, a trifluoromethyl, a halogen, a methylthio, a sulfonyl, a carbonyl, a hydroxy, an amino, a thiol or a RGM; X is O, S, Se, $NR_{15}$, $CR_{15}R_{16}$; n is 0 to 3.

The length of the conjugated polymethine bridge between the two ring systems greatly affects the dye's absorption and emission properties. Each of $R_1$, $R_2$, $R_3$, when present, is independently a hydrogen, a fluoro, a chloro, an alkyl having 1-6 carbons, an alkoxy having 1-6 carbons, an aryloxy, a N-heteroaromatic moiety, or an iminium ion. Alternatively, two substituents $R_1/R2$, $R_2/R_3$, when taken in combination, form a 4-, 5-, or 6-membered saturated or unsaturated hydrocarbon ring that is unsubstituted or is optionally substituted one or more times by a saturated or unsaturated alkyl having 1-6 carbons, a halogen, or a carbonyl oxygen. Typically, each of $R_1$, $R_2$ and $R_3$, when present, is a hydrogen. Where one of $R_1$, $R_2$ and $R_3$ is a nonhydrogen, it is typically the substituent on the center carbon of bridged and conjugated double bonds. Similarly, where bridged and conjugated double bonds incorporate a 4-, 5-, or 6-membered ring, it typically occurs at the center of the conjugated bridge moiety.

Additionally, selection of the A, B and X moieties may also significantly affect the dye's absorption and fluorescence emission properties. A and B optionally the same or different, and spectral properties of the resulting dye may be tuned by careful selection of A and B. In one embodiment, X is $CR_{15}R_{16}$ where $R_{15}$ and $R_{16}$ are a hydrogen or an alkyl group having 1-30 carbons, that is optionally substituted one or more times by a hydroxy, a carboxy, a sulfo, an amino, an alkylamino having 1-6 carbons or dialkylamino having 2-20 carbons. Alternatively, $R_{15}$ and $R_{16}$ in combination complete a five or six membered saturated or unsaturated ring that is optionally substituted by a RGM. Preferably $R_{15}$ and $R_{16}$ are independently an alkyl with 1-6 carbon atoms that are unsubstituted or are substituted once by a hydroxy, a sulfo, a carboxy or an amino. In one aspect of the invention, $R_{15}$ and $R_{16}$ are alkyls having 1-6 carbons, preferably methyls. In another aspect of the invention, one of $R_{15}$ and $R_{16}$ is a methyl, and the other is an alkyl having 1-10 carbons that is substituted by a carboxy or by a sulfo or by a hydroxy, or by a RGM.

Incorporation of one or more non-hydrogen substituents on the fused rings can be used to fine tune the absorption and emission spectrum of the resulting dye.

Another preferred embodiment of the invention is a compound of Formula VI

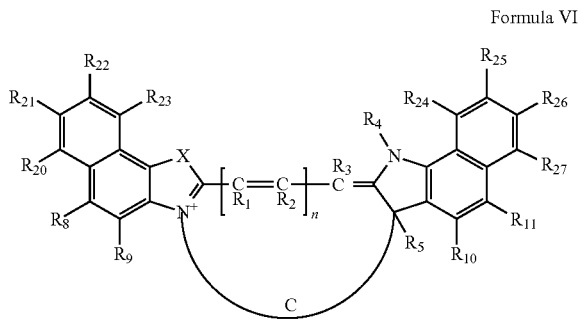

Formula VI wherein C is a non-conjugated chain of 10-50 linear atoms selected from carbon, nitrogen, oxygen, phosphorus and sulfur that are further substituted by a hydrogen, an alkyl having 1-20 carbons, an alkoxy having 1-20 carbons, a trifluoromethyl, a halogen, a methylthio, a sulfonyl, a carbonyl, a hydroxy, an amino, a thiol or a RGM. $R_1$ to $R_{27}$ are a hydrogen, an alkyl having 1-20 carbons, an alkoxy having 1-20 carbons, a trifluoromethyl, a halogen, a methylthio, a sulfonyl, a carbonyl, a hydroxy, an amino, a thiol or a RGM; X is O, S, Se, $NR_{15}$ or $CR_{15}R_{16}$; n is 0 to 3.

Another preferred embodiment of the invention is a compound of Formula VII

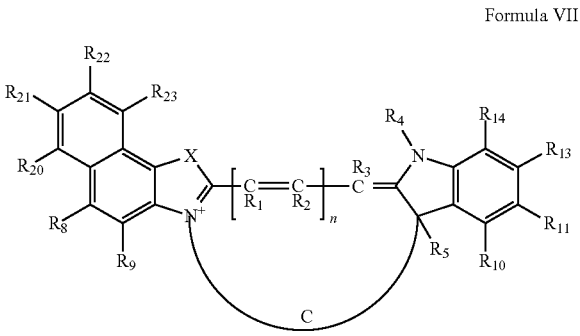

Formula VII wherein C is a non-conjugated chain of 10-50 linear atoms selected from carbon, nitrogen, oxygen, phosphorus and sulfur that are further substituted by a hydrogen, an alkyl having 1-20 carbons, an alkoxy having 1-20 carbons, a trifluoromethyl, a halogen, a methylthio, a sulfonyl, a carbonyl, a hydroxy, an amino, a thiol or a RGM. $R_1$ to $R_{23}$ are a hydrogen, an alkyl having 1-20 carbons, an alkoxy having 1-20 carbons, a trifluoromethyl, a halogen, a methylthio, a sulfonyl, a carbonyl, a hydroxy, an amino, a thiol or a RGM; X is O, S, Se, $NR_{15}$ or $CR_{15}R_{16}$; n is 0 to 3.

In one aspect of the invention, one or two or more of $R_1$ to $R_{27}$ is an amino, a carboxy and a thiol according to Formula I. In one aspect of the invention, the carbocyanine dyes of the invention are sulfonated one or more times.

In addition, the dyes of the invention are substituted by one or more chemically reactive groups (RGM) or conjugated substances as described below. In a preferred embodiment, the dye of the invention is substituted by only one RGM.

Many embodiments of the compounds of the invention possess an overall electronic charge. It is to be understood that when such electronic charges are shown to be present, they are balanced by the presence of appropriate counterions, which may or may not be explicitly identified. A biologically compatible counterion, which is preferred for some applications, is not toxic in biological applications, and does not have a substantially deleterious effect on biomolecules. Where the compound of the invention is positively charged, the counterion is typically selected from, but not limited to, chloride, bromide, iodide, sulfate, alkanesulfonate, arylsulfonate, phosphate, perchlorate, tetrafluoroborate, tetraarylboride, nitrate and anions of aromatic or aliphatic-carboxylic acids. Where the. compound of the invention is negatively charged, the counterion is typically selected from, but not limited to, alkali metal ions, alkaline earth metal ions, transition metal ions, ammonium or substituted ammonium or pyridinium ions. Preferably, any necessary counterion is biologically compatible, is not toxic as used, and does not have a substantially deleterious effect on biomolecules. Counterions are readily changed by methods well known in the art, such as ion-exchange chromatography, or selective precipitation.

It is to be understood that-the dyes of the invention have been drawn in one or another particular electronic resonance structure. Every aspect of the instant invention applies equally to dyes that are formally drawn with other permitted resonance structures, as the electronic charge on the subject dyes is delocalized throughout the dye itself.

In one embodiment of the invention, the dye contains at least one L-RGM, where RGM is the reactive group that is attached to the dye by a covalent linkage L. In certain embodiments, the covalent linkage attaching the dye to RGM contains multiple intervening atoms that serve as a spacer. The dyes with a RGM label a wide variety of organic or inorganic substances that contain or are modified to contain functional groups with suitable reactivity, resulting in chemical attachment of the conjugated substance. As used herein, "reactive group moiety (RGM)" means moiety on the compound that is capable of chemically reacting with a functional group on a different compound to form a covalent linkage. Typically the reactive group is an electrophile or nucleophile that can form a covalent linkage through exposure to the corresponding functional group that is a nucleophile or electrophile, respectively. Alternatively, the reactive group is a photoactivatable group, and becomes chemically reactive only after illumination with light of an appropriate wavelength. Typically, the conjugation reaction between the reactive dye and the substance to be conjugated results in one or more atoms of the reactive group RGM to be incorporated into a new linkage L attaching the dye to the conjugated substance. Selected examples of reactive groups and linkages are shown in Table 1 where the reaction of an electrophilic group and a nucleophilic group yields a covalent linkage.

TABLE 1

Examples of RGM groups that are used for preparing covalent linkages:

| Electrophilic Group | Nucleophilic Group | Resulting Conjugate |
|---|---|---|
| activated esters* | amines/anilines | carboxamides |
| acrylamides | thiols | thioethers |
| acyl azides** | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carbo |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |

TABLE 1-continued

Examples of RGM groups that are used for preparing covalent linkages:

| Electrophilic Group | Nucleophilic Group | Resulting Conjugate |
|---|---|---|
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thioethers |
| aryl halides | amines | aryl amines |
| aziridines | thiols | thioethers |
| boronates | glycols | boronate esters |
| carbodiimides | carboxylic acids | N-acylureas or anhydrides |
| diazoalkanes | carboxylic acids | esters |
| epoxides | thiols | thioethers |
| haloacetarnides | thiols | thioethers |
| haloplatinate | amino | platinum complex |
| haloplatinate | heterocycle | platinum complex |
| haloplatinate | thiol | platinum complex |
| halotriazines | amines/anilines | aminotriazines |
| halotriazines | alcohols/phenols | triazinyl ethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols. | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

*Activated esters, as understood in the art, generally have the formula —COL, where L is a good leaving group (e.g. succinimidyloxy (—ONC$_4$H$_4$0$_2$) sulfosuccinimidyloxy (—ONC$_4$H$_3$O$_2$, —SO$_3$H), -1-oxybenzotriazolyl (—OC$_6$H$_4$N$_3$); or an aryloxy group or aryloxy substituted one or more times by electron withdrawing substituents such as nitro, fluoro, chloro, cyano, or trifluoromethyl, or combinations thereof, used to form activated aryl esters; or a carboxylic acid activated by a carbodiimide to foim an anhydride or mixed anhydride —OCOAlk or —OCN(Alk$_1$)NH(Alk$_2$), where Alk$_1$ and Alk$_2$, which may be the same or different, are C$_1$-C$_{20\ alkyl}$, C$_1$-C$_{20}$ perfluoroalkyl, or C$_1$-C$_{20}$ alkoxy; or cyclohexyl, 3-dimethylaminopropyl, or N-morpholinoethyl).
**Acyl azides can also rearrange to isocyanates.

Choice of the reactive group used to attach the dye to the substance to be conjugated typically depends on the functional group on the substance to be conjugated and the type or length of covalent linkage desired. The types of functional groups typically present on the organic or inorganic substances include, but are not limited to, amines, amides, thiols, alcohols, phenols, aldehydes, ketones, phosphonates, imidazoles, hydrazines, hydroxylamines, disubstituted amines, halides, epoxides, carboxylate esters, sulfonate esters, purines, pyrimidines, carboxylic acids, olefinic bonds, or a combination of these groups. A single type of reactive site may be available on the substance (typical for polysaccharides), or a variety of sites may occur (e.g. amines, thiols, alcohols, phenols), as is typical for proteins. A conjugated substance may be conjugated to more than one dye, which may be the same or different, or to a substance that is additionally modified by a hapten, such as biotin. Although some selectivity can be obtained by careful control of the reaction conditions, selectivity of labeling is best obtained by selection of an appropriate reactive dye.

Typically, RGM will react with an amine, a thiol, an alcohol, an aldehyde or a ketone. Preferably RGM reacts with an amine or a thiol functional group. In one embodiment, RGM is an acrylamide, a reactive amine (including a cadaverine or ethylenediamine), an activated ester of a carboxylic acid (typically a succinimidyl ester of a carboxylic acid), an acyl azide, an acyl nitrile, an aldehyde, an alkyl halide, an anhydride, an aniline, an aryl halide, an azide, an aziridine, a boronate, a carboxylic acid, a diazoalkane, a haloacetamide, a halotriazine, a hydrazine (including hydrazides), an imido ester, an isocyanate, an isothiocyanate, a maleimide, a phosphoramidite, a reactive platinum complex, a sulfonyl halide, or a thiol group. By "reactive platinum complex" is particularly meant chemically reactive platinum complexes such as described in U.S. Pat. Nos. 5,580,990; 5,714,327; 5,985,566.

Where the reactive group is a photoactivatable group, such as an azide, diazirinyl, azidoaryl, or psoralen derivative, the dye becomes chemically reactive only after illumination with light of an appropriate wavelength. Where RGM is an activated ester of a carboxylic acid, the reactive dye is particularly useful for preparing dye-conjugates of proteins, nucleotides, oligonucleotides, or haptens. Where RGM is a maleimide or haloacetamide the reactive dye is particularly useful for conjugation to thiol-containing substances. Where RGM is a hydrazide, the reactive dye is particularly useful for conjugation to periodate-oxidized carbohydrates and glycoproteins, and in addition is an aldehyde-fixable polar tracer for cell microinjection. Preferably, RGM is a carboxylic acid, a succinimidyl ester of a carboxylic acid, a haloacetamide, a hydrazine, an isothiocyanate, a maleimide group, an aliphatic amine, a perfluorobenzamido, an azidoperfluorobenzamido group, or a psoralen. More preferably, RGM is a succinimidyl ester of a carboxylic acid, a maleimide, an iodoacetamide, or a reactive platinum complex. Based on the above-mentioned attributes, the appropriate reactive dyes of the invention are selected for the preparation of the desired dye-conjugates, whose advantageous properties make them useful for a wide variety of applications. Particularly useful dye conjugates include, among others, conjugates where substrate is a peptide, a nucleotide, an antigen, a steroid, a vitamin, a drug, a hapten, a metabolite, a toxin, an environmental pollutant, an amino acid, a protein, a nucleic acid, a nucleic acid polymer, a carbohydrate, a lipid, an ion-complexing moiety, a glass or a non-biological polymer. Alternatively, substrate is a cell, a cellular system, a cellular fragment, or a subcellular particle (e.g. inter alia), a virus particle, a bacterial particle, a virus component, a biological cell (such as animal cell, plant cell, bacteria, yeast, or protist), or a cellular component. Reactive dyes typically label functional groups at the cell surface, in cell membranes, organelles, or cytoplasm.

Typically substrate is an amino acid, a peptide, a protein, a tyrainine, a polysaccharide, an ion-complexing moiety, a nucleoside, a nucleotide, an oligonucleotide, a nucleic acid, a hapten, a psoralen, a drug, a hormone, a lipid, a lipid assembly, a polymer, a polymeric microparticle, a biological cell or virus. More typically, substrate is a peptide, a protein, a nucleotide, an oligonucleotide, or a nucleic acid. When conjugating dyes of the invention to such biopolymers, it is possible to incorporate more dyes per molecule to increase the fluorescent signal. For example, it is possible to incorporate at least three molecules of such dyes per molecule of antibody without loss of total fluorescence, whereas fluorescence of the spectrally comparable Cy5 (wherein n=2) is strongly quenched when greater than approximately two Cy5 dyes are incorporated per antibody. These results confirm problems with Cy5 conjugates reported by others, e.g. BIOCONJUGATE CHEM., 11, 696 (2000). The optimally labeled conjugates of the invention are typically much more fluorescent than conjugates of the Cy5 dye or 1,1'-crosslinked Cy5 at the same antibody concentration.

In one embodiment, substrate is an amino acid (including those that are protected or are substituted by phosphonates, carbohydrates, or $C_1$ to $C_{25}$ carboxylic acids), or is a polymer of amino acids such as a peptide or protein. Preferred conjugates of peptides contain at least five amino acids, more preferably 5 to 36 amino acids. Preferred peptides include, but are not limited to, neuropeptides, cytokines, toxins, protease substrates, and protein kinase substrates. Preferred protein conjugates include enzymes, antibodies, lectins, glycoproteins, histones, albumins, lipoproteins, avidin, streptavidin, protein A, protein G, phycobiliproteins and other fluorescent proteins, hormones, toxins, chemokines and growth factors. In one preferred aspect, the conjugated protein is a phycobiliprotein, such as allophycocyanin, phycocyanin, phycoerythrin, allophycocyanin B, B-phycoerythrin, and phycoerythrocyanin, (for example, see U.S. Pat. No. 5,714,386 to Roederer (1998)). Particularly preferred are conjugates of R-phycoerythrin and of allophycocyanin with selected dyes of the invention that serve as excited-state energy acceptors or donors. In these conjugates, excited state energy transfer results in long wavelength fluorescence emission when excited at relatively short wavelengths.

In one aspect of the invention, substrate is a conjugated substance that is an antibody (including intact antibodies, antibody fragments, and antibody sera, etc.), an amino acid, an angiostatin or endostatin, an avidin or streptavidin, a biotin (e.g. an amidobiotin, a biocytin, a desthiobiotin, etc.), a blood component protein (e.g. an albumin, a fibrinogen, a plasminogen, etc.), a dextran, an enzyme, an enzyme inhibitor, an IgG-binding protein (e.g. a protein A, protein G, protein A/G, etc.), a fluorescent protein (e.g. a phycobiliprotein, an aequorin, a green fluorescent protein, etc.), a growth factor, a hormone, a lectin (e.g. a wheat germ agglutinin, a conconavalin A, etc.), a lipopolysaccharide, a metal-binding protein (e.g. a calmodulin, etc.), a microorganism or portion thereof (e.g. a bacteria, a virus, a yeast, etc.), a neuropeptide and other biologically active factors (e.g. a dermorphin, a deltropin, an endomorphin, an endorphin, a tumor necrosis factor etc.), a non-biological microparticle (e.g. of ferrofluid, gold, polystyrene, etc.), a nucleotide, an oligonucleotide, a peptide toxin (e.g. an apamin, a bungarotoxin, a phalloidin, etc.), a phospholipid-binding protein (e.g. an annexin, etc.), a small-molecule drug (e.g. a methotrexate, etc.), a structural protein (e.g. an actin, a fibronectin, a laminin, a microtubule-associated protein, a tublin, etc.), or a tyramide.

In another embodiment, substrate is a nucleic acid base, nucleoside, nucleotide or a nucleic acid polymer, including those that are modified to possess an additional linker or spacer for attachment of the dyes of the invention, such as an alkynyl linkage (U.S. Pat. No. 5,047,519), an aminoallyl linkage (U.S. Pat. No. 4,711,955), or a heteroatomsubstituted linker (U.S. Pat. No. 5,684,142) or other linkage. In another embodiment, the conjugated substance is a nucleoside or nucleotide analog that links a purine or pyrimidine base to a phosphate or polyphosphate moiety through a noncyclic spacer. In another embodiment, the dye is conjugated to the carbohydrate portion of a nucleotide or nucleoside, typically through a hydroxyl group but additionally through a thiol or amino group (U.S. Pat. Nos. 5,659,025; 5,668,268; 5,679,785). Typically, the conjugated nucleotide is a nucleoside triphosphate or a deoxynucleoside triphosphate or a dideoxynucleoside triphosphate. Incorporation of methylene moieties or nitrogen or sulfur heteroatoms into the phosphate or polyphosphate moiety is also useful. Nonpurine and nonpyrimidine bases such as 7-deazapurines (U.S. Pat. No. 6,150,510) and nucleic acids containing such bases can also be coupled to dyes of the invention. Nucleic acid adducts prepared by reaction of depurinated nucleic acids with amine, hydrazide or hydroxylamine derivatives provide an additional means of labeling and detecting nucleic acids, e.g. "A method for detecting abasic sites in living cells: age-dependent changes in base excision repair." Atamna H, Cheung I, Ames B N. PROC. NATL. ACAD. SCI. U.S.A. 97, 686-691 (2000).

Preferred nucleic acid polymer conjugates are labeled, single- or multi-stranded, natural or synthetic DNA or RNA, DNA or RNA oligonucleotides, or DNA/RNA hybrids, or incorporate an unusual linker such as morpholine derivatized phosphates, or peptide nucleic acids such as N-(2-aminoethyl)glycine units. When the nucleic acid is a synthetic oligonucleotide, it typically contains fewer than 50 nucleotides, more typically fewer than 25 nucleotides. Conjugates of peptide nucleic acids (PNA) (Nielsen, et al. U.S. Pat. No. 5,539,082) may be preferred for some applications because of their generally faster hybridization rates.

In one embodiment, the conjugated oligonucleotides of the invention are aptamers for a particular target molecule, such as a metabolite, dye, hapten, or protein. That is, the oligonucleotides have been selected to bind preferentially to the target molecule. Methods of preparing and screening aptamers for a given target molecule have been previously described and are known in the art [for example, U.S. Pat. No. 5,567,588 to Gold (1996)].

In another embodiment, substrate is a carbohydrate that is typically a polysaccharide, such as a dextran, heparin, glycogen, amylopectin, mannan, inulin, starch, agarose and cellulose. Alternatively, the carbohydrate is a polysaccharide that is a lipopolysaccharide. Preferred polysaccharide conjugates are dextran, or lipopolysaccharide conjugates.

Conjugates having an ion-complexing moiety serve as indicators for calcium, sodium, magnesium, zinc, potassium, or other biologically important metal ions. Preferred ion-complexing moieties are crown ethers (U.S. Pat. No. 5,405,975); derivatives of 1,2-bis(2-aminophenoxyethane)-N,N,M,$N^t$-tetraacetic acid (BAPTA chelators; U.S. Pat. Nos. 5,453,517; 5,516,911 and 5,049,673); derivatives of 2-carboxymethoxyaniline-N,N-diacetic acid (APTRA chelators; AM. J. PHYSIOL., 256, C540 (1989)); or pyridine- and phenanthroline-based metal ion chelators (U.S. Pat. No. 5,648,270); or derivatives of nitrilotriacetic acid, see e.g. "Single-step synthesis and characterization of biotinylated nitrilotriacetic acid, a unique reagent for the detection of histidine-tagged proteins immobilized on nitrocellulose", McMahan S A and Burgess R R, ANAL. BIOCHEM., 236, 101-106 (1996). Preferably, the ion-complexing moiety is a crown ether chelator, a BAPTA chelator, an APTRA chelator or a derivative of nitrilotriacetic acid.

Other conjugates of non-biological materials include dye-conjugates of organic or inorganic polymers, polymeric films, polymeric wafers, polymeric membranes, polymeric particles, or polymeric microparticles (magnetic and non-magnetic microspheres); iron, gold or silver particles; conducting and non-conducting metals and non-metals; and glass and plastic surfaces and particles. Conjugates are optionally prepared by copolymerization of a dye that contains an appropriate functionality while preparing the polymer, or by chemical modification of a polymer that contains functional groups with suitable chemical reactivity. Other types of reactions that are useful for preparing dye-conjugates of polymers include catalyzed polymerizations or copolymerization of alkenes and reactions of dienes with dienophiles, transesterifications or transaminations. In another embodiment, the conjugated substance is a glass or silica, which may be formed into an optical fiber or other structure. In one embodiment, conjugates of biological polymers Such as peptides, proteins, oligonucleotides, nucleic acid polymers are also labeled with at least a second luminescent dye, which is optionally an additional dye of the present invention, to form an energy-transfer pair. In some aspects of the invention, the labeled conjugate functions as an enzyme substrate, and enzymatic hydrolysis disrupts the energy transfer. In another embodiment of the invention, the energy-transfer pair that incorporates a dye of the invention is conjugated to an oligonucleotide that displays efficient fluorescence quenching in its hairpin conformation [the so-called "molecular beacons" of Tyagi, et al., NATURE BIOTECHNOLOGY, 16, 49 (1998)] or fluorescence energy transfer.

The preparation of dye conjugates using reactive dyes is well documented, e.g. Hermanson G T, BIOCONJUGATE TECHNIQUES, Academic Press, New York (1996); Haugland R P, METHODS MOL. BIOL., 45; 205-21 (1995); and Brinkley, BIO0014.TUGATE CHEM., 3, 2 (1992). Conjugates typically result from mixing appropriate reactive dyes and the substance to be conjugated in a suitable solvent in which both are soluble. The majority of the dyes of the invention are readily soluble in aqueous solutions, facilitating conjugation reactions with most biological materials. For those reactive dyes that are photoactivated, conjugation requires illumination of the reaction mixture to activate the reactive dyes.

Synthesis

Synthesis of the cyanine dyes of the invention depends on initial preparation of certain key intermediates. The intermediates have the following general structures (for simplicity, all but a few of the possible substituents are shown as hydrogen):

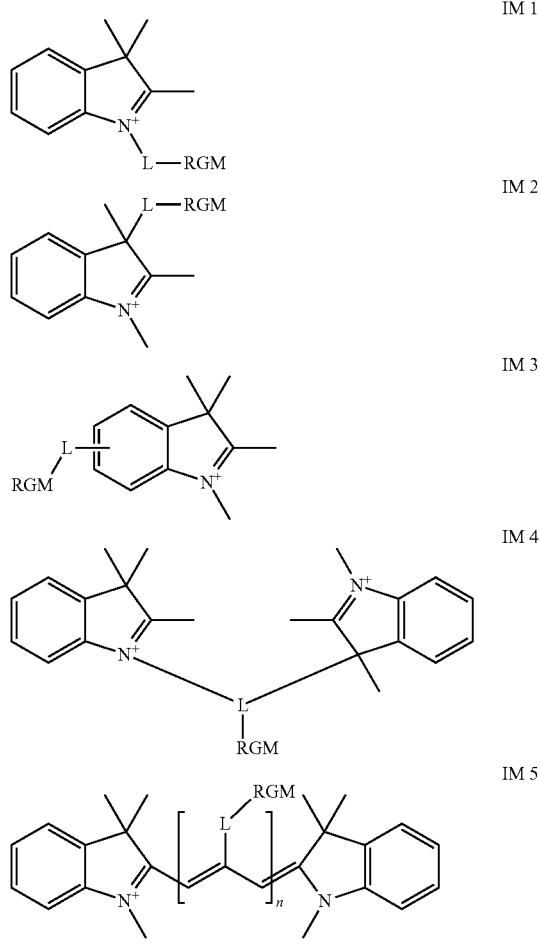

IM 1

IM 2

IM 3

IM 4

IM 5

These basic structures are optionally further substituted, during or after synthesis, to give the corresponding dye substituents as defined above. For carbocyanines, the novel key intermediates are readily synthesized by a reaction that is analogous to a Fischer indole synthesis (see Sundberg R J, THE CHEMISTRY OF INDOLES, Organic chemistry, a series of monographs, 1970, Academic Press). The typical synthesis of different substituted carbocyanines is illustrated in FIGS. 6-11.

Synthesis of the cyanine dyes of the invention, where RGM is at the 3-position of the indolium and imidazolium, depends on initial preparation of key inteiniediate IM 2, Licha, et al., U.S. Pat. No. 6,083,485 (2000) described a typical systhesis of intermediate IM 2. These basic structures are optionally further substituted, during or after synthesis, to give the corresponding dye substituents as defined above. The novel key intermediates are readily synthesized by a reaction that is analogous to a Fischer indole synthesis or through the condensations of phenylendiamine with a carbonyl compound. The typical total synthesis of 3-RGM-substituted carbocyanines is illustrated in FIG. 7.

Synthesis of the cyanine dyes of the invention, where attachment is at the bridged and non-conjugated chain C, is either through the initial preparation of key intermediate IM 4 or through the modification of the disclosed procedures described for the synthesis of 1,1'-crosslinked carbocyanines (WO 01/02374 to Singh, et al). The typical total synthesis of carbocyanines with RGM on the non-conjugated chain C is illustrated in FIGS. 8 and 11.

Synthesis of the cyanine dyes of the invention, where attachment is at the bridged and conjugated double bonds, depends on initial preparation of certain key bridged intermediates such as IM 5. For example, N,N'-diphenylformamidine, triethylorthoformate malonaldehyde bis(phenylimine) hydrochloride, 1,1,3-trimethoxypropane, 1,1,3,3-tetramethoxypropane and glutaconaldehyde dianil monochloride are the well-known bridged intermediates used in the synthesis of carbocycanines. More examples of appropriate carbocyanines that have bridged and conjugated double bonds have been previously described in the literature of U.S. Pat. No. 5,831,098 to Ollmann, Jr (1998); U.S. Pat. No. 6,086, 737 to Patonay, et al. (2000); U.S. Pat. No. 6,048,982 to Waggoner (2000); and U.S. Pat. No. 5,453,505 to Lee, et al. (1995); U.S. Pat. No. 5,639,874 to Middendorf, et al. (1997); U.S. Pat. No. 3,864,644 to Lincoln, et al. (1975); U.S. Pat. No. 4,011,086 to Simson (1977). Typically, each of $R_1$, R2 and R3 in Formula I, when present, is hydrogen. Where one of $R_1$, $R_2$ and $R_3$ is nonhydrogen, it is typically the substituent on the center carbon of BRIDGE. Similarly, where bridged incorporates a 4-, 5-, or 6-membered ring, it typically occurs at the center of the bridged moiety. The typical total synthesis of carbocyanines substituted at the bridged and conjugated carbon atoms with RGM is illustrated in FIG. 9.

Scheme 3. Typical synthesis of indolium intermediate

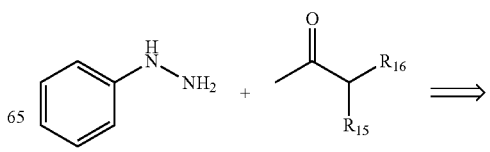

-continued

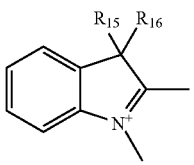

For the synthesis of carbocyanines, an appropriately substituted aryl hydrazine (for simplicity, all but a few of the possible substituents are shown as hydrogen), which is typically an appropriately substituted phenylhydrazine, is reacted with an appropriately substituted methyl ketone to yield a 3,3-disubstituted 2-methylindole derivative (see Scheme 3). It is particularly suitable to utilize a sulfonated phenylhydrazine derivative or a sulfonated naphthylhydrazine derivative to increase the solubility of the final dye. The 3,3-disubstituted-2-methylindole is then quaternized on the nitrogen atom to an indolium derivative with an alkylating agent that is typically an alkyl halide such as ethyl iodide, an alkylsulfonate such as methyl p-toluenesulfonate or a cyclic sulfonate such as propanesultone or butanesultone. Typically, the key indolium or benzoindolium intermediates are sulfonated one or more times before or after quaternization and subsequent condensation with the benzazolium moiety and polymethine moiety to form the subject dyes. Variations on these methods are well known in the art that yield substituents on the polymethine bridge or on the indolium or benzolium portion of the dye precursor.

The azacarbocyanine dyes of the present invention can be analogously synthesized. [for example, see Leung W, et al., WO 02/26891; Brooker, et at, J. AM. CHEM. SOC., 64,199 (1942); Heravi, et al., INDIAN J. CHEM., 36B, 1025 (1997); Smith, et al. SULFUR LETTERS, 17, 197 (1994); Chu-Moyer, et al. J. ORG. CHEM., 60, 5721 (1995); Turner, J. ORG. CHEM., 48, 3401 (1983); Couture, et al. J. HETEROCYCLIC CHEM., 24, 1765 (1987); Petrie, et al. J. HETEROCYCLIC CHEM, 14, 1045, (1977); Barlin, et al. AUST. J. CHEM., 37, 1729 (1984); Saikachi et al. CHEM. & PHARM. BULL., 9, 941 (1961); Barlin, AUST. J. CHEM., 36, 983 (1983); Foye, et al., J. PHARM. SCI., 64, 1371 (1975); Khanna, et al. J. ORG. CHEM., 60, 960 (1995)); British Patent No. 870,753 to Ficken, et al. (1961); Ficken, et al., "DIAZAINDENES AND THEIR QUANTERNARY SALTS-Part I", pp 3202-3212 (1959); Ficken, et al., "DIAZAINDENES AND THEIR QUANTERNARY SALTS-Part II", pp 584-588 (1961)1. In general, the synthesis of these dyes requires three precursors: the appropriate benzazolium or azabenzazolium salt (the "A" and "B" moieties), and a source for the polymethine spacer. Typically each component is selected so as to incorporate the appropriate chemical substituents, or functional groups (e.g. RGM) that can be converted to the appropriate substituents. The chemistry that is required to prepare and combine these precursors so as to yield any of the subject derivatives is generally well understood by one skilled in the art.

It is recognized that there are many possible variations that may yield equivalent results. The substituents on the aromatic carbons of the azabenzazolium moiety are typically incorporated in the parent aza- or polyazabenzazole molecule prior to quaternization with an alkylating agent. However, such substituents may also be incorporated during the synthesis of the azabenzazole moiety. Alkyl, alkoxy, carboxyl, and halogen substituents at aromatic carbons are typically already present as substituents on the benzazole or azabenzazole precursors, or on compounds that are readily converted to such precursors using methods well-known in the art. Sulfonic acid groups are typically introduced on the precursors prior to condensation of the cyanine dye [for example, see U.S. Pat. No. 5,767,287 to Bobrow, et al. (1998)]. Aminoalkyl groups typically contain by a protecting group when they are first introduced, typically by substitution onto the benzazole or azabenzazole precursor. The protecting group is then removed after condensation of the cyanine dye. Aromatic amino groups are typically prepared via the reduction of a nitro substituted benzolium precursor, which in turn is prepared by the nitration of the benzazole precursor.

The methods for synthesis of dyes that contain a variety of reactive groups such as those described in Table 1 are well documented in the art. Particularly useful are amine-reactive dyes such as "activated esters" of carboxylic acids, which are typically synthesized by coupling a carboxylic acid to a relatively acidic "leaving group". Other preferred amine-reactive groups include sulfonyl halides, which are prepared from sulfonic acids using a halogenating agent such as $PCl_5$ or $POCl_3$; halotriazines, which are prepared by the reaction of cyanuric halides with amines; and isocyanates or isothiocyanates, which are prepared from amines and phosgene or thiophosgene, respectively.

Dyes containing amines and hydrazides are particularly useful for conjugation to carboxylic acids, aldehydes and ketones. Most often these are synthesized by reaction of an activated ester of a carboxylic acid or a sulfonyl halide with a diamine, such as cadaverine, or with a hydrazine. Alternatively, aromatic amines are commonly synthesized by chemical reduction of a nitroaromatic compound. Amines and hydrazines are particularly useful precursors for synthesis of thiol-reactive haloacetamides or maleimides by standard methods.

Nucleosides and nucleotides labeled with dyes of the invention are particularly useful for some applications of nucleic acid labeling. The use of carbocyanine-amidites for labeling nucleotides and nucleosides have been previously described [U.S. Pat. No. 5,986,086 to Brush, et al. (1999); U.S. Pat. No. 5,808,044 to Brush, et al. (1998); U.S. Pat. No. 5,556,959 to Brush, et al. (1996)].

Applications and Methods of Use

In one aspect of the invention, the dye compounds of the invention are used to directly stain or label a sample so that the sample can be identified or quantitated. For instance, such dyes may be added as part of an assay for a biological target analyte, as a detectable tracer element in a biological or non-biological fluid; or for such purposes as photodynamic therapy of tumors, in which a dyed sample is irradiated to selectively destroy tumor cells and tissues; or to photoablate arterial plaque or cells, usually through the photosensitized production of singlet oxygen. In one preferred embodiment, dye conjugate is used to stain a sample that comprises a ligand for which the conjugated substance is a complementary member of a specific binding pair (e.g. Table 2).

Typically, the sample is obtained directly from a liquid source or as a wash from a solid material (organic or inorganic) or a growth medium in which cells have been introduced for culturing, or a buffer solution in which cells have been placed for evaluation. Where the sample comprises cells, the cells are optionally single cells, including microorganisms, or multiple cells associated with other cells in two or three dimensional layers, including multicellular organisms, embryos, tissues, biopsies, filaments, biofilms, etc.

Alternatively, the sample is a solid, optionally a smear or scrape or a retentate removed from a liquid or vapor by filtration. In one aspect of the invention, the sample is obtained from a biological fluid, including separated or unfiltered biological fluids such as urine, cerebrospinal fluid, blood, lymph fluids, tissue homogenate, interstitial fluid, cell extracts, mucus, saliva, sputum, stool, physiological secretions or other similar fluids. Alternatively, the sample is obtained from an environmental source such as soil, water, or air; or from an industrial source such as taken from a waste stream, a water source, a supply line, or a production lot.

TABLE 2

Representative specific binding pairs

| Antigen | Antibody |
|---|---|
| Biotin | Anti-biotin or avidin or streptavidin or neutravidin |
| IgG* | Protein A or protein G or anti-IgG antibody |
| Drug | Drug receptor |
| Toxin | Toxin |
| Carbohydrate | Lectin.or carbohydrate receptor |
| Peptide | Peptide receptor |
| Nucleotide | Complimentary nucleotide |
| Protein | Protein receptor |
| Enzyme substrate | Enzyme |
| DNA (RNA) | aDNA (aRNA)** |
| Hormone | Hormone receptor |
| Psoralen | Nucleic acid |
| Target molecule | RNA or DNA aptamer |
| Ion | Ion chelator |

*IgG is an immunoglobulin;
**aDNA and aRNA are the antisense (complementary) strands used for hybridization In yet another embodiment, the sample is present on or in solid or semi-solid matrix. In one aspect of the invention, the matrix is a membrane. In another aspect, the matrix is an electrophoretic gel, such as is used for separating and characterizing nucleic acids or proteins, or is a blot prepared by transfer from an electrophoretic gel to a membrane. In another aspect, the matrix is a silicon chip or glass slide, and the analyze of interest has been immobilized on the chip or slide in an array (e.g. the sample comprises proteins or nucleic acid polymers in a microarray). In yet another aspect, the matrix is a microwell plate or microfluidic chip, and the sample is analyzed by automated methods, typically by various methods of high-throughput screening, such as drug screening.

The dye compounds of the invention are generally utilized by combining a dye compound of the invention as described above with the sample of interest under conditions selected to yield a detectable optical response. The term "dye compound" is used herein to refer to all aspects of the claimed dyes, including both reactive dyes and dye conjugates. The dye compound typically forms a covalent or non-covalent association or complex with an element of the sample, or is simply present within the bounds of the sample or portion of the sample. The sample is then illuminated at a wavelength selected to elicit the optical response. Typically, staining the sample is used to determine a specified characteristic of the sample by further comparing the optical response with a standard or expected response.

A detectable optical response means a change in, or occurrence of, an Opticarsignal that is detectable either by observation or instrumentally. Typically the detectable response is a change in fluorescence, such as a change in the intensity, excitation or emission wavelength distribution of fluorescence, fluorescence lifetime, fluorescence polarization, or a combination thereof. The degree and/or location of staining, compared with a standard or expected response, indicates whether and to what degree the sample possesses a given characteristic. Some dyes of the invention may exhibit little fluorescence emission, but are still useful as chromophoric dyes. Such chromophores are useful as energy acceptors in FRET applications, or to simply impart the desired color to a sample or portion of a sample.

For biological applications, the dye compounds of the invention are typically used in an aqueous, mostly aqueous or aqueous-miscible solution prepared according to methods generally known in the art. The exact concentration of dye compound is dependent upon the experimental conditions and the desired results, but typically ranges from about one nanomolar to one millimolar or higher. The optimal concentration is determined by systematic variation until satisfactory results with minimal background fluorescence are accomplished.

The dye compounds are most advantageously used to stain samples with biological components. The sample may comprise heterogeneous mixtures of components (including intact cells, cell extracts, bacteria, viruses, organelles, and mixtures thereof), or a single component or homogeneous group of components (e.g. natural or synthetic amino acids, nucleic acids or carbohydrate polymers, or lipid membrane complexes). These dyes are generally non-toxic to living cells and other biological components, within the concentrations of use.

The dye compound is combined with the sample in any way that facilitates contact between the dye compound and the sample components of interest. Typically, the dye compound or a solution containing the dye compound is simply added to the sample. Certain dyes of the invention, particularly those that are substituted by one or more sulfonic acid moieties, tend to be impermeant to membranes of biological cells, and once inside viable cells are typically well retained. Treatments that peinteabilize the plasma membrane, such as electroporation, shock treatments or high extracellular ATP can be used to introduce selected dye compounds into cells. Alternatively, selected dye compounds can be physically inserted into cells, e.g. by pressure microinjection, scrape loading, patch clamp methods, or phagocytosis.

Dyes that incorporate an aliphatic amine or a hydrazine residue can be microinjected into cells, where they can be fixed in place by aldehyde fixatives such as foinialdehyde or glutaraldehyde. This fixability makes such dyes useful for intracellular applications such as neuronal tracing.

Dye compounds that possess a lipophilic substituent, such as phospholipids, will noncovalently incorporate into lipid assemblies, e.g. for use as probes for membrane structure; or for incorporation in liposomes, lipoproteins, films, plastics, lipophilic microspheres or similar materials; or for tracing. Lipophilic dyes are useful as fluorescent probes of membrane structure.

Chemically reactive dye compounds will covalently attach to a corresponding functional group on a wide variety of materials, forming dye conjugates as described above. Using dye compounds to label reactive sites on the surface of cells, in cell membranes or in intracellular compartments such as organelles, or in the cell's cytoplasm, permits the determination of their presence or quantity, accessibility, or their spatial and temporal distribution in the sample. Photoreactive dyes can be used similarly to photolabel components of the outer membrane of biological cells or as-photo-fixable polar tracers for cells.

Optionally, the sample is washed after staining to remove residual, excess or unbound dye compound. The sample is optionally combined with one or more other solutions in the course of staining, including wash solutions, peimeabilization and/or fixation solutions, and solutions containing additional detection reagents. An additional detection reagent typically produces a detectable response due to the presence of a specific cell component, intracellular substance, or cellular condition, according to methods generally known in the art. Where the additional detection reagent has, or yields a product with, spectral properties that differ from those of the subject dye compounds, multi-color applications are possible. This is particularly useful where the additional detection reagent is a dye or dye-conjugate of the present invention having spectral properties that are detectably distinct from those of the staining dye.

The dye conjugates of the invention are used according to methods extensively known in the art; e.g. use of antibody conjugates in microscopy and immunofluorescent assays; and nucleotide or oligonucleotide conjugates for nucleic acid hybridization assays and nucleic acid sequencing (e.g., U.S. Pat. No. 5,332,666 to Prober, et al. (1994); U.S. Pat. No. 5,171,534 to Smith, et al. (1992); U.S. Pat. No. 4,997,928 to Hobbs (1991); and WO Appl. 94/05688 to Menchen, et al.). Dye-conjugates of multiple independent dyes of the invention possess utility for multi-color applications.

At any time after or during staining, the sample is illuminated with a wavelength of light selected to give a detectable optical response, and observed with a means for detecting the optical response. Equipment that is useful for illuminating the dye compounds of the invention includes, but is not limited to, hand-held ultraviolet lamps, mercury arc lamps, xenon lamps, lasers and laser diodes. These illumination sources are optionally integrated into laser scanners, fluorescence microplate readers, standard or minifluorometers, or chromatographic detectors. Preferred embodiments of the invention are dyes that are be excitable at or near the wavelengths 633-636 nm, 647 nm, 660 nm, 680 nm and beyond 700 nm, as these regions closely match the output of relatively inexpensive excitation sources.

The optical response is optionally detected by visual inspection, or by use of any of the following devices: CCD cameras, video cameras, photographic films, laser-scanning devices, fluorometers, photodiodes, quantum counters, epifluorescence microscopes, scanning microscopes, flow cytometers, fluorescence microplate readers, or by means for amplifying the signal such as photomultiplier tubes. Where the sample is examined using a flow cytometer, examination of the sample optionally includes sorting portions of the sample according to their fluorescence response.

One aspect of the instant invention is the formulation of kits that facilitate the practice of various assays using any of the dyes of the invention, as described above. The kits of the invention typically comprise a colored or fluorescent dye of the invention, either present as a chemically reactive label useful for preparing dye-conjugates, or present as a dye-conjugate where the conjugated substance is a specific binding pair member, or a nucleoside, a nucleotide, an oligonucleotide, a nucleic acid polymer, a peptide, or a protein. The kit optionally further comprises one or more buffering agents, typically present as an aqueous solution. The kits of the invention optionally further comprise additional detection reagents, a purification medium for purifying the resulting labeled substance, luminescence standards, enzymes, enzyme inhibitors, organic solvent, or instructions for carrying out an assay of the invention.

EXAMPLES

Examples of some synthetic strategies for selected dyes of the invention, as well as their characterization, synthetic precursors, conjugates and method of use are provided in the examples below. Further modifications and permutations will be obvious to one skilled in the art. The examples below are given so as to illustrate the practice of this invention. They are not intended to limit or define the entire scope of this invention.

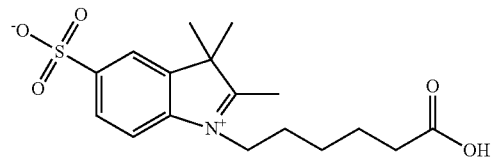

Example 1

Preparation of Compound 1

Compound 1

The potassium salt of 2,3,3-trimethylindolinium-5-sulfonate is synthesized by Fisher indole synthesis through the reaction of 4-hydrazinobenzenesulfonic acid and 3-methyl-2-butanone, followed by neutralizing the indolinyl sulfonic acid with saturated solution of potassium hydroxide in 2-propanol. The mixture of the potassium salt of 2,3,3-trimethylindolinium-5-sulfonate (11 g, 39.7 mmol) and 6-bromohexanoic acid (9.68 g, 49.6 mmol) in 1,2-dichlorobenzene (100 mL) is heated at 120° C. for 10 hours under nitrogen. The crude product is triturated with 2-propanol. The solid is filtered and washed with 2-propanol and ether, and dried under vacuum to give Compound 1 (9.2 g).

Example 2

Preparation of Compound 2

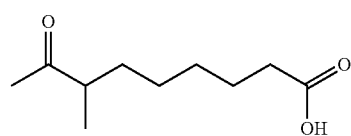

Compound 2

To the solution of sodium ethoxide (173.4 mmol, prepared from 4.0 g sodium in 200 mL dry ethanol) is added ethyl 2-methylacetoacetate (25.0 g, 173.4 mmol), followed by ethyl 6-bromohexanonate (44.5 g, 190.7 mmol). The mixture is heated to reflux for 12 hours. After cooling to room temperature, the mixture is filtered and the filtrate is concentrated. The residue is treated with 1M HCl to pH 1 and the aqueous solution is extracted with chloroform twice. The organic layer is washed with brine and dried over $Na_2SO_4$. After removal of solvent, the residue is purified on silica gel to afford 15 g ethyl 2-(5-ethoxycarbonyl)pentyl-2-methylacetoacetate.

The above acetoacetate (13.6 g) in methanol (130 mL) is mixed with a solution of NaOH (6.6 g) in water (60 mL). The mixture is stirred at 50° C. for 3 hours. After removal of methanol, the residue is acidified with 1M HCl to pH 2. The aqueous solution is extracted with EtOAc (2×100 mL). The organic layer is washed with brine and dried over $Na_2SO_4$. The crude product is purified with silica gel chromatography to yield 7-methyl-8-oxo-nonanoic acid Compound 2 (6.4 g).

Example 3

Preparation of Compound 3

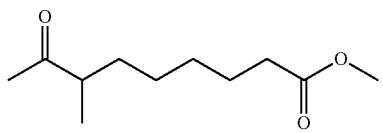

Compound 3

To the solution of Compound 2 (6.4 g) in methanol (50 mL) is added $H_2SO_4$ (1.0 mL) dropwisely. The mixture is refluxed 30 min. After cooling to room temperature, the reaction mixture is concentrated and the residue is diluted with ethyl acetate (100 mL). The solution is washed with saturated $NaHCO_3$ and brine. The organic layer is dried over $Na_2SO_4$. After removal of solvent, the methyl 7-methyl-8-oxo-nonanoate Compound 3 is obtained and used without further purification.

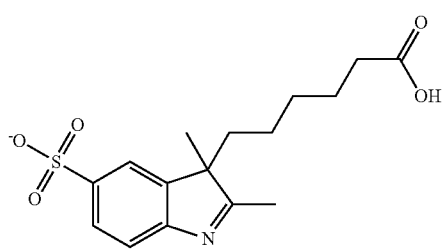

Example 4

Preparation of Compound 4

Compound 4

The mixture of 7-methyl-8-oxo-nonanoic acid (Compound 2, 4.2 g, 21.5 mmol) and 4-hydrazinobenzenesulfonic acid (4.23 g, 22.5 mol) in acetic acid (30 mL) is heated to reflux for 8 hours. After removal of the solvent, the residue is purified on silica gel to give Compound 4 (3.1 g).

Example 5

Preparation of Compound 5

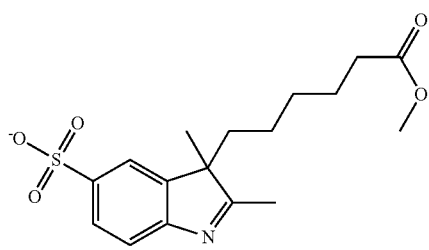

Compound 5

The mixture of methyl 7-methyl-8-oxo-nonanoate (Compound 3, 6.9 g, 34.4 mmol) and 4-hydrazinobenzenesulfonic acid (6.45 g, 32.7 mol) in acetic acid (50 mL) is heated to reflux for 8 hours. After removal of the solvent, the residue is purified on silica gel to give Compound 5 (9.7 g).

Example 6

Preparation of Compound 6

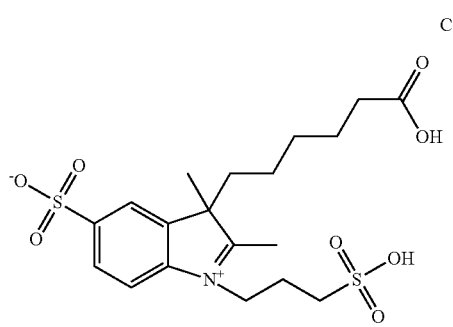

Compound 6

A solution of Compound 4 (3.1 g) and potassium acetate (1.1 g) in methanol (20 mL) is stirred at room temperature for 15 min. After removal of methanol, the resulting potassium salt is heated with 1,3-propanesultone (2.0 g) in 1,2-dichlorobenzene (5 mL) at 110° C. for 1.5 hour. The mixture is cooled to room temperature and 1,2-dichlorobenzene is decanted. The solid is triturated with 2-propanol and the free powder is filtered and washed with 2-propanol and ether and dried under vacuum to yield Compound 6.

Example 7

Preparation of Compound 7

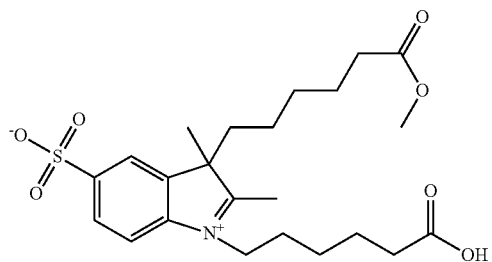

Compound 7

A solution of Compound 5 (3.3 g) and potassium acetate (1.0 g) in methanol (20 mL) is stirred at room temperature for 15 min. After removal of methanol; the resulting potassium salt is heated with 6-bromohexanoic acid (3.4 g) in 1,2-dichlorobenzene (10 mL) at 110° C. overnight. The mixture is cooled to room temperature and 1,2-dichlorobenzene is decanted. The solid is triturated with ethyl ether and the free powder is filtered and washed with ether and dried under vacuum to yield Compound 7.

Example 8

Preparation of Compound 8

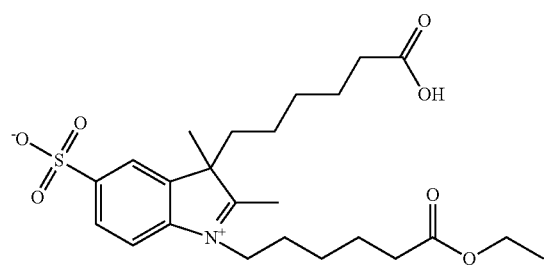

Compound 8

A solution of Compound 4 (3.3 g) and potassium acetate (1.0 g) in methanol (20 mL) is stirred at room temperature for 15 min. After removal of methanol, the resulting potassium salt is heated with ethyl 6-bromohexanonate (8.01 g) in 1,2-dichlorobenzene (10 mL) at 110° C. overnight. The mixture is cooled to room temperature and 1,2-dichlorobenzene is decanted. The solid is triturated with ethyl ether and the free powder is filtered and washed with ether and dried under vacuum to yield Compound 8.

Example 9

Preparation of Compound 9

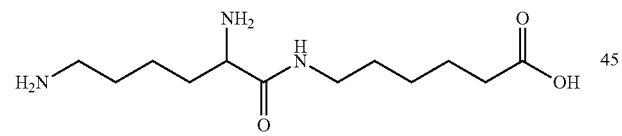

Compound 9

The mixture of Boc-Lys(Boc)-OH (1.0 g, 2.9 mmol), N-hydroxysuccinimide (0.33 g, 2.9 mmol) and DCC (0.63 g, 3.03 mmol) in THF (25 mL) is stirred at room temperature overnight. After removal of solid, the filtrate [Boc-Lys(Boc)-OSu] is added to a solution of 6-aminocaprioic acid (0.38 g, 2.9 mmol) in water (20 mL), followed by addition of 2N $Na_2CO_3$ to adjust pH to 8-9. The mixture is stirred at room temperature overnight. After diluted with water (150 mL), the mixture is acidified with 4% aqueous HCl to pH 3 and extracted with ethyl acetate (2×50 mL). The combined extract is washed with brine and dried over $Na_2SO_4$. After removal of solvent, the residue [Boc-Lys(Boc)-NH(CH$_2$)$_5$COOH] is dissolved in 1,4-dioxane (15 mL), followed by addition of 4M HCl in dioxane (10 mL). The mixture is stirred for 1 hour. The solvent is decanted and the solid is washed with ethyl acetate (3×20 mL) and ether (3×20 mL). The HCl salt of Compound 9 is dried under vacuum.

Example 10

Preparation of Compound 10

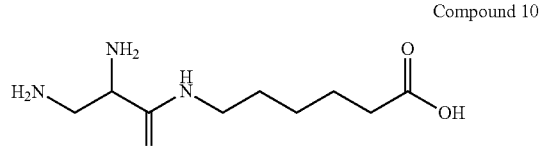

Compound 10

Compound 10 is prepared starting from DL-2,3-diaminopropionic acid analogously to the preparation of Compound 9.

Example 11

Preparation of Compound 11

5-Ethoxycarbonyl-2,3,3-trimethyl-3H-indole is synthesized through the reaction of ethyl 4-hydrazinobenzoate and 3-methyl-2-butanone. Compound 11 is synthesized by the similar procedure described for the synthesis of Compound 1.

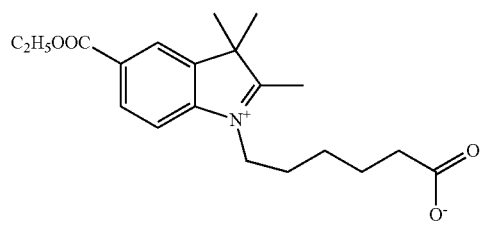

Compound 11

Example 12

Preparation of Compound 12

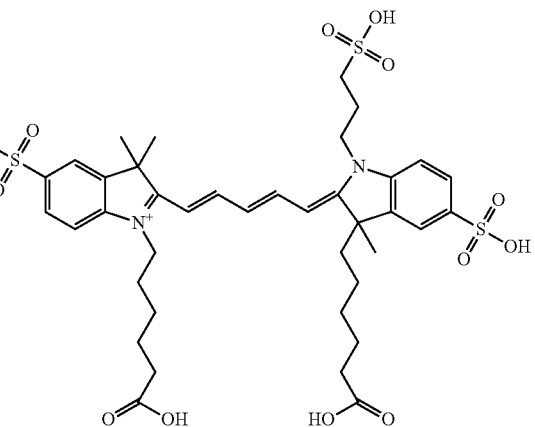

Compound 12

A solution of Compound 1 (100 mg, 0.283 mmol) and malonaldehyde bis(phenylimine) monohydrochloride (77 mg, 0.297 mmol) in acetic acid (0.5 mL) and acetic anhydride (0_5 mL) is heated at 120° C. for 1 hour. The completion of the reaction is monitored by absorption spectra in methanol. The solution of anyl intermediate is mixed with Compound 6 (131 mg, 0.283 mol), then more acetic anhydride (0.5 mL) and pyridine (1.0 mL) is added. The mixture is heated for 30 min until the anyl intermediate disappears (monitored by absorption spectra). The reaction mixture is cooled and poured into ethyl acetate (50 mL). The crude product is collected by centrifugation and washed with ethyl acetate twice. Preparative HPLC purification give Compound 12 as blue powder (35 mg).

Example 13

Preparation of Compound 13

To a solution of Compound 12 (28.4 mg, 0.0334 mmol) and O—(N-succinimidyl)-N,N,N',N'-tetramethyluronium tetrafluoroborate (26 mg, 0.0864 mmol) in DMF (0.65 mL) is added triethylamine (0.04 mL). The mixture is stirred at room temperature for 1 h. The reaction mixture is poured into EtOAc (15 mL). The di-succinimidyl ester of Compound 12 is collected by centrifugation and washed with EtOAc (2×10 mL), EtOEt (1×10 mL) and dried under vacuum.

The above di-succinimidyl ester of Compound 12 is dissolved in water (50 mL) and a solution of Compound 9 (22.2 mg, 0.0667 mmol) in water (25 mL) [neutralized with $Na_2CO_3$ (7.1 mg, 0.0667 mmol)] is added slowly during the period of 30 minutes. The mixture is stirred at room temperature overnight. After removal of solvent, the residue is purified by preparative HPLC to give Compound 13 as blue powder (20 mg).

Example 14

Preparation of Compound 14

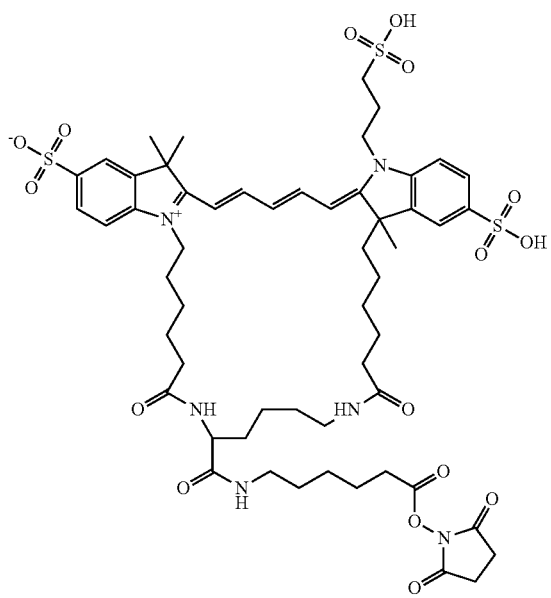

Compound 14

To a solution of Compound 13 (10 mg, 0.0093 mmol) in DMF (0.4 mL) is added O—(N-succinimidyl)-N,N,N',N'-tetramethyluronium tetrafluoroborate (3.64 mg, 0.0121 mmol), followed by triethylamine (0.03 mL). The mixture is stirred at room temperature for 1 h. The solution is poured into EtOAc (15 mL). The solid is centrifuged and washed with EtOAc (3×10 mL), ether (1×10 mL) and dried under vacuum to give Compound 14 as bright blue powder (11 mg).

Example 15

Preparation of Compound 15

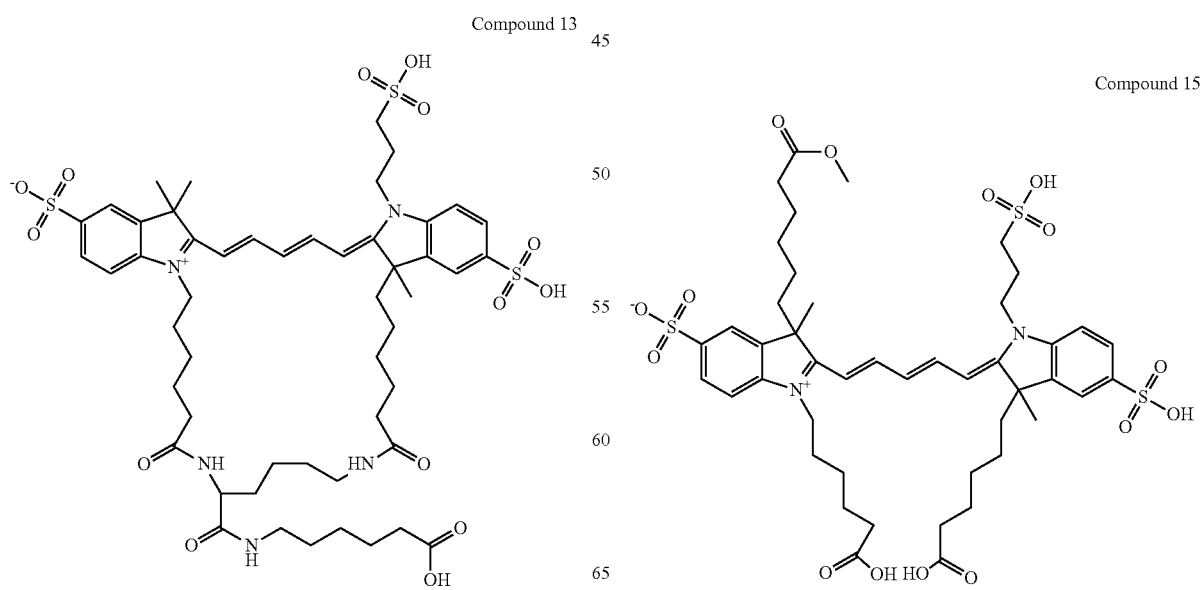

Compound 13

Compound 15

A solution of Compound 6 (100 mg, 0.217 mmol) and malonaldehyde bis(phenylimine) monohydrochloride (56 mg, 0.217 mmol) in acetic acid (0.5 mL) and acetic anhydride (0.5 mL) is heated at 120° C. for 1 hour. The completion of the reaction is monitored by absorption spectra. The solution of anyl intermediate is mixed with Compound 7 (101 mg, 0.217 mol), then more acetic anhydride (0.5 mL) and pyridine (1.0 mL) is added. The mixture is heated for 30 min until the anyl intermediate disappears (monitored by absorption spectra). The reaction mixture is cooled and poured into ethyl acetate (50 mL). The crude product is collected by centrifugation and washed with ethyl acetate twice. Preparative HPLC purification gives Compound 15 as bright blue powder (15 mg).

Example 16

Preparation of Compound 16

To a solution of Compound 15 (6.0 mg, 0.0060 mmol) and O—(N-succinimidyl)-N,N,N',N'-tetramethyluronium tetrafluoroborate (5.4 mg, 0.018 mmol) in DMF (0.40 mL) is added triethylamine (0.04 mL). The mixture is stirred at room temperature for 1 h. The resulting solution of di-succinimidyl ester of Compound 15 is diluted with DMF (30 mL), followed by addition of a solution of ethylenediamine (0.71 mg, 0.012 mmol) in DMF (20 mL) during the period of 30 minutes. The mixture is stirred at room temperature overnight. After removal of solvent, the residue is treated with 1N NaOH (2 mL). After the hydrolysis reaction is completing (monitored by HPLC), the reaction mixture is diluted with water (5 mL) and neutralized with 1N HCl. Preparative HPLC purification gives Compound 16 as blue powder (2 mg).

Compound 16

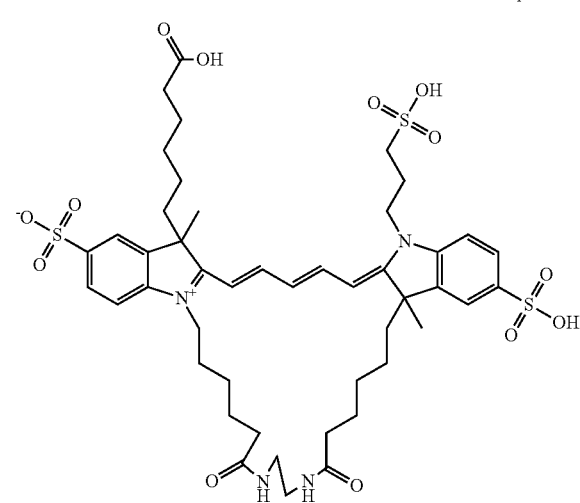

Example 17

Preparation of Compound 17

Compound 17

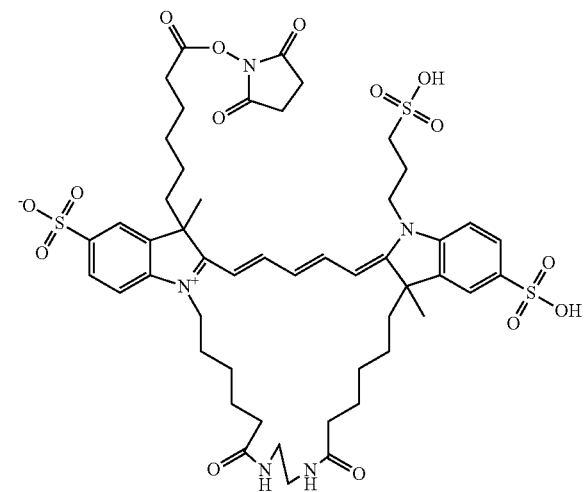

To a solution Compound 16 (2 mg, 0.002 mm91) in MAT (0.4 mL) is added O—(N succinimidyl)-NAN';N'-fetramethyluronium tetrafluoroborate (0.8 mg, 0.0027 mmol), followed by triethylamine (0.02 mL). The mixture is stirred at room temperature for 1 h. The solution is poured into EtOAc (15 mL). The solid is centrifuged and washed with EtOAc (3×10 mL), ether (1×10 mL) and dried under vacuum to give Compound 17 as bright blue powder (2 mg).

Example 18

Preparation of Compound 18

Compound 18

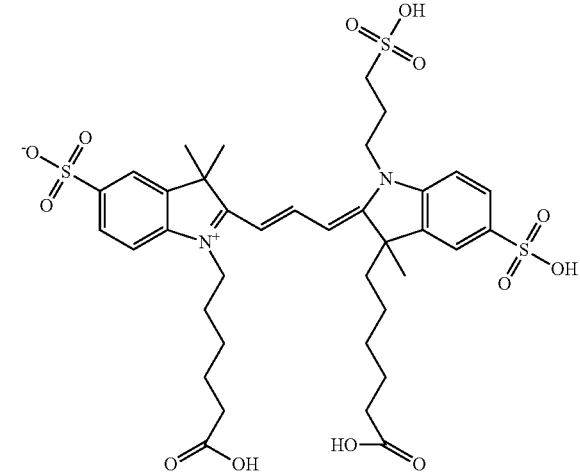

A solution of Compound 1 (100 mg, 0.283 mmol) and N,N⁻-diphenylformamidine (58 mg, 0.297 mmol) in acetic acid (0.5 mL) and acetic anhydride (0.5 mL) is heated at 120° C. for 1 hour. The completion of the reaction is monitored by absorption spectra in methanol. The solution of anyl intermediate is mixed with Compound 6 (131 mg, 0.283. mol), then more acetic anhydride (0.5 mL) and pyridine (1.0 mL) is added. The mixture is heated for 30 min until the anyl intermediate disappears (monitored by absorption spectra). The reaction mixture is cooled and poured into ethyl acetate (50 mL). The crude product is collected by centrifugation and washed with ethyl acetate twice. Preparative HPLC purification gives Compound 18 (33 mg).

Example 19

Preparation of Compound 19

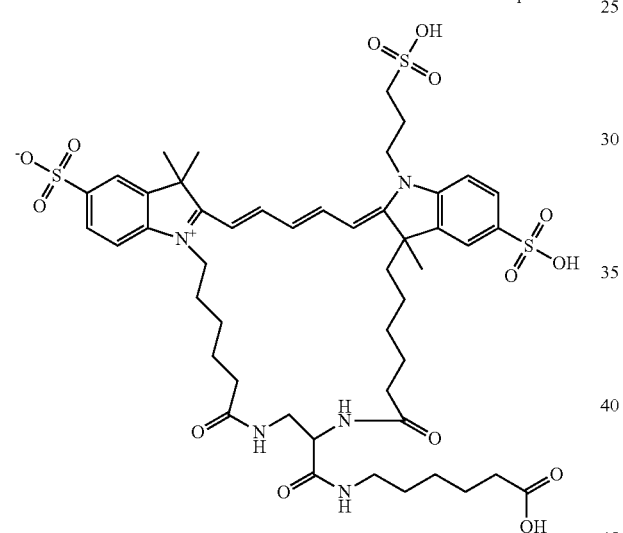

Compound 19

To a solution of Compound 18 (25 mg, 0.0303 mmol) and O—(N-succinimidyl)-N,N,N',N'-tetramethyluronium tetrafluoroborate (24 mg, 0.0788 mmol) in DMF (0.5 mL) is added triethylamine (0.04 mL) The mixture is stirred at room temperature for 1 h. The reaction mixture is poured into EtOAc (15 mL). The di-succinimidyl ester of Compound 18 is collected by centrifugation and washed with EtOAc (2×10 mL), EtOEt (1×10 mL) and dried under vacuum.

The above di-succinimidyl ester of Compound 18 is dissolved in water (50 mL) and a solution of Compound 10 (17.6 mg, 0.0606 mmol) in water (25 mL) [neutralized with. Na$_2$CO$_3$ (7.1 mg, 0.0606 mmol)] is added slowly during the period of 30 minutes. The mixture is stirred at room temperature overnight. After removal of solvent, the residue is purified by preparative HPLC to give Compound 19 (20 mg).

Example 20

Preparation of Compound 20

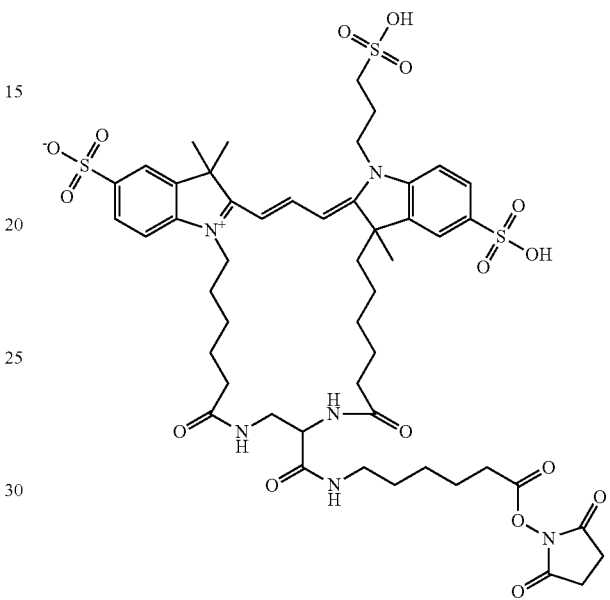

Compound 20

To a solution Compound 19 (10 mg, 0.0099 mmol) in DMF (0.4 mL) is added O—(N-succinimidyl)-N,N,N',N'-tetramethyluronium tetrafluoroborate (3.64 mg, 0.0119 mmol), followed by triethylamine (0.03 mL). The mixture is stirred at room temperature for 1 h. The solution is poured into EtOAc (15 mL). The solid is centrifuged and washed with EtOAc (3×10 mL), ether (1×10 mL) and dried under vacuum to give Compound 20 (10 mg).

Example 21

Preparation of Compound 21

A solution of Compound 1 (100 mg, 0.283 mmol) and glutaconaldehyde dianil hydrochloride (85 mg, 0.297 mmol) in acetic acid (0.5 mL) and acetic anhydride (0.5 mL) is heated at 120° C. for 1.5 hour. The completion of the reaction is monitored by absorption spectra in methanol. The solution of anyl intermediate is mixed with Compound 6 (130 mg, 0.283 mol), then more acetic anhydride (0.5 mL) and pyridine (1.0 mL) is added. The mixture is heated for 30 min until the anyl intermediate disappears (monitored by absorption spectra). The reaction mixture is cooled and poured into ethyl acetate (50 mL). The crude product is collected by centrifugation and washed with ethyl acetate twice. Preparative HPLC purification gives Compound 21 (20 mg).

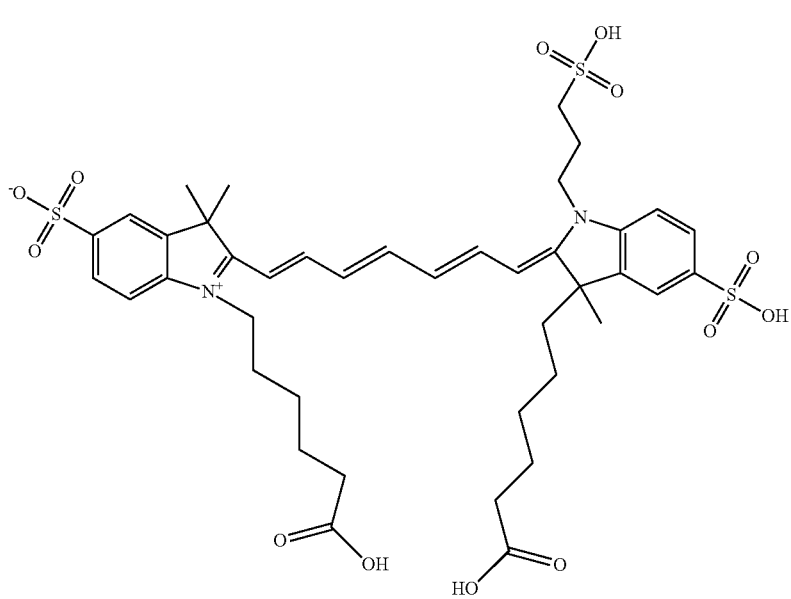

Compound 21

Example 22

Preparation of Compound 22

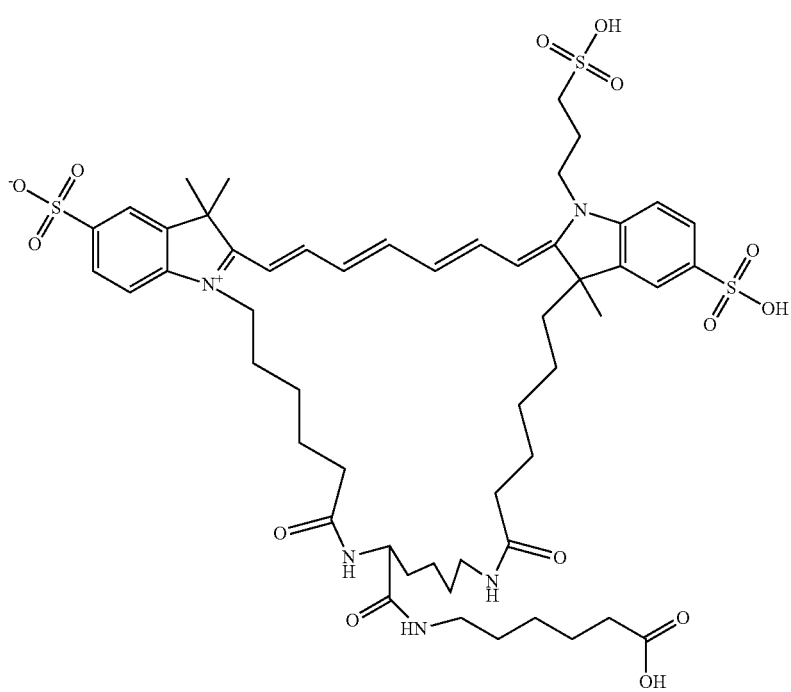

Compound 22

To a solution of Compound 21 (20 mg, 0.0228 mmol) and O—(N-succinimidyl)-N,N,N',N'-tetramethyluronium tetrafluoroborate (17.2 mg, 0.0570 mmol) in DMF (0.5 mL) is added triethylamine (0.03 mL). The mixture is stirred at room temperature for 1 h. The reaction mixture is poured into EtOAc (15 mL). The di-succinimidyl ester of Compound 21 is collected by centrifugation and washed with EtOAc (2×10 mL), EtOEt (1×10 mL) and dried under vacuum.

The above di-succinimidyl ester of Compound 21 is dissolved in water (40 mL) and a solution of Compound 9 (151 mg, 0.0456 mmol) in water (25 mL) (neutralized with $Na_2CO_3$ (4.8 mg, 0.0456 mmol)) is added slowly during the period of 30 minutes. The mixture is stirred at room temperature overnight. After removal of solvent, the residue is purified by preparative HPLC to give Compound 22 (20 mg).

Example 23

Preparation of Compound 23

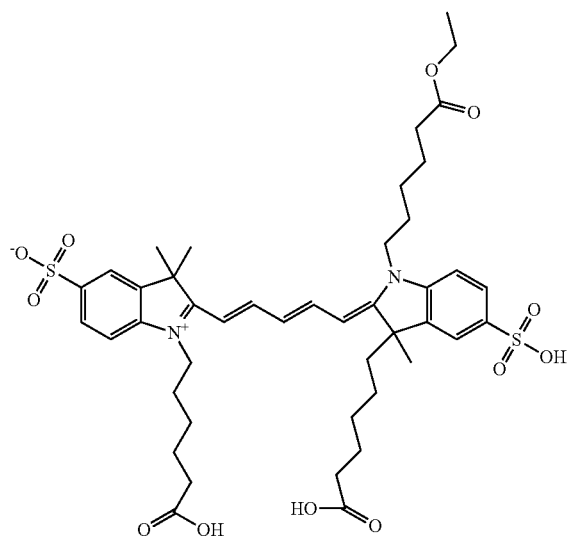

A solution of Compound 1 (100 mg, 0.283 mmol) and malonaldehyde bis(phenylimine) monohydrochloride (77 mg, 0.297 mmol) in acetic acid (0.5 mL) and acetic anhydride (0.5 mL) is heated at 120° C. for 1 hour. The completion of the reaction is monitored by absorption spectra in methanol. The solution of anyl intermediate is mixed with Compound 8 (136 mg, 0.283 mol), then more acetic anhydride (0.5 mL) and pyridine (1.0 mL) is added. The mixture is heated for 30 min until the anyl intermediate disappears (monitored by absorption spectra). The reaction mixture is cooled and poured into ethyl acetate (50 mL). The crude product is collected by centrifugation and washed with. ethyl acetate twice. Preparative HPLC purification gives Compound 23 as bright blue powder (30 mg).

Example 24

Preparation of Compound 24

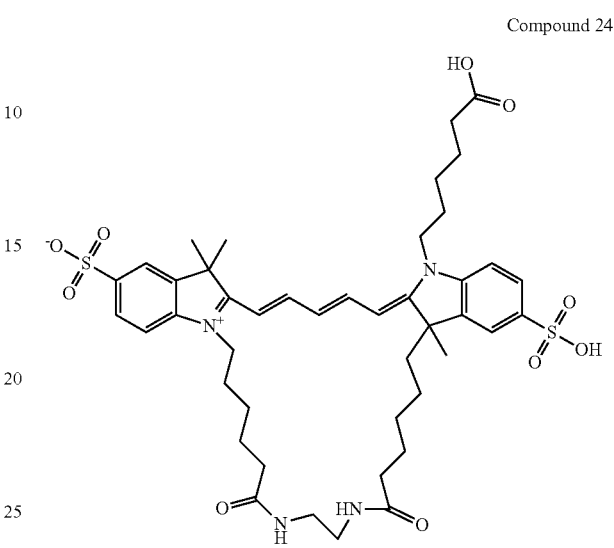

To a solution of Compound 23 (30.0 mg, 0.0344 mmol) and O—(N-succinimidyl)-N,N,N',N'-tetramethyluronium tetrafluoroborate (26.0 mg, 0.0861 mmol) in DMF (0.60 mL) is added triethylamine (0.04 mL). The mixture is stirred at room temperature for 1 h. The resulting solution of di-succinimidyl ester of Compound 23 is diluted with DMF (50 mL), followed by addition of a solution of ethylenediamine (4.1 mg, 0.0688 mmol) in DMF (30 mL) during the period of 30 minutes. The mixture is stirred at room temperature overnight. After removal of solvent, the residue is treated with 1N NaOH (3 mL). After the hydrolysis reaction is completing (monitored by HPLC), the reaction mixture is diluted with water (10 mL) and neutralized with 1N HCl. Preparative HPLC purification gives Compound 24 as blue powder (22 mg).

Example 25

Preparation of Compound 25

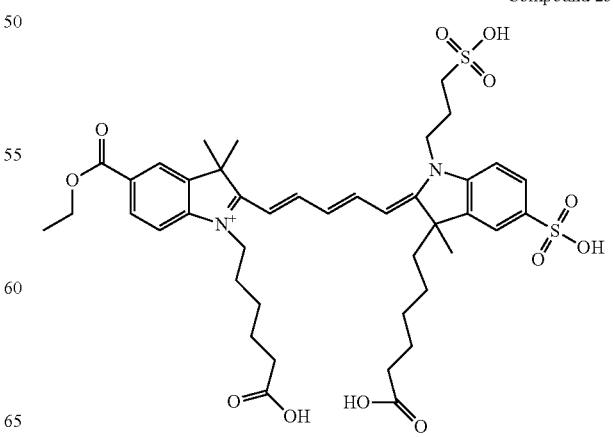

A solution of Compound 11 (100 mg, 0.292 mmol) and. malonaldehyde bis(phenylimine) monohydrochloride (79 mg, 0.306 mmol) in acetic acid (0.5 mL) and acetic anhydride (0.5 mL) is heated at 120° C. for 1 hour. The completion of the reaction is monitored by absorption spectra in methanol. The solution of anyl intelinediate is mixed with Compound 6 (135 mg, 0.292 mol), then more acetic anhydride (0.5 mL) and pyridine (1.0 mL) is added. The Mixture is heated for 30 Min until the anyl intermediate disappears (monitored by absorption spectra). The reaction mixture is cooled and poured into ethyl acetate (50 mL). The crude product is collected by centrifugation and washed with ethyl acetate twice. Preparative HPLC purification gives Compound 25 as bright blue powder (33 mg).

Example 26

Preparation of Compound 26

Compound 26

To a solution of Compound 25 (30.0 mg, 0.0356 mmol) and O—(N-succinimidyl)-N,N,N',N'-tetramethyluronium tetrafluoroborate (26.8 mg, 0.0890 mmol) in DMF (0.60 mL) is added triethylamine (0.04 mL). The Mixture is stirred at room temperature for 1 h. The resulting solution of di-succinimidyl ester of Compound 25 is diluted with DMF (50 mL), followed by addition of a solution of ethylenediamine (4.3 mg, 0.0712 mmol) in DMF (30 mL) during the period of 30 minutes. The mixture is stirred at room temperature overnight. After removal of solvent, the residue is treated with 1N NaOH (3 mL). After the hydrolysis reaction is completing (monitored by HPLC), the reaction mixture is diluted with water (10 mL) and neutralized with 1N HCl. Preparative HPLC purification gives Compound 26 as blue powder (20 mg).

Example 27

Preparation of Compound 27

The reaction of di-potassium salt of 1,1,2-trimethylbenzindolenium-6,8-disulfonic acid [BIOCONJUGATE CHEM., 356-362 (1996)] (5.0 g, 0.011 mmol) and 6-bromohexanoic acid (5.3 g, 0.027 mmol) in dichlorobenzene at 120° C. overnight, followed by the same work-up procedure as described for the synthesis of Compound 1, affords Compound 27 (4.5 g).

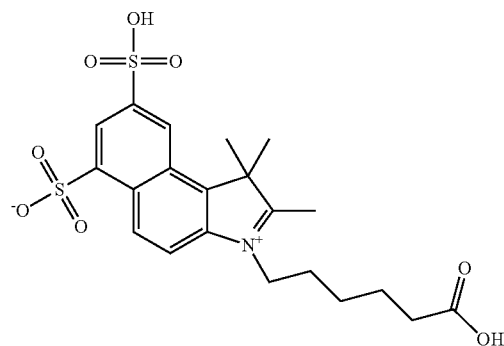

Compound 27

Example 28

Preparation of Compound 28

Compound 28

The Compound 28 is analogously synthesized by the same procedure described for the synthesis of Compound 4 and Compound 6, starting from the reaction of 6-hydrazinonaphthalene 1,3-disulfonate [BIOCONJUGATE CHEM., 356-362 (1996)] with 7-methyl-8-oxo-nonanoic acid Compound 2, followed by quaternization with 1,3-propanesultone.

Example 29

Preparation of Compound 29

A solution of Compound 27 (100 mg, 0.207 mmol) and malonaldehyde bis(phenylimine) monohydrochloride (56 mg, 0.217 mmol) in acetic acid (0.5 mL) and acetic anhydride (0.5 mL) is heated at 120° C. for 1 hour. The completion of the reaction is monitored by absorption spectra in methanol. The solution of anyl intermediate is mixed with Compound 28 (123 mg, 0.207 mol), then more acetic anhydride (0.5 mL) and pyridine (1.0 mL) is added. The mixture is heated for 30 min until the anyl intermediate disappears (monitored by absorption spectra). The reaction mixture is cooled and poured into ethyl acetate (50 mL). The crude product is collected by centrifugation and washed with ethyl acetate twice. Preparative HPLC purification gives Compound 29 as bright blue powder (30 mg).

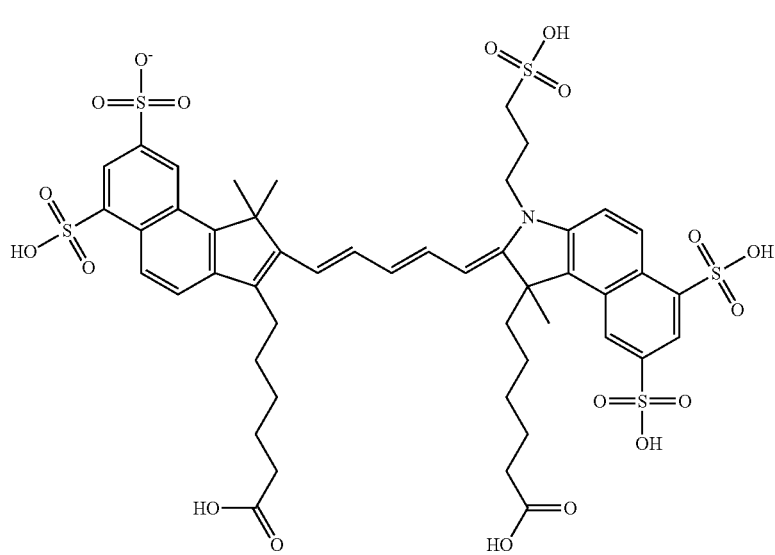

Compound 29

Example 30

Preparation of Compound 30

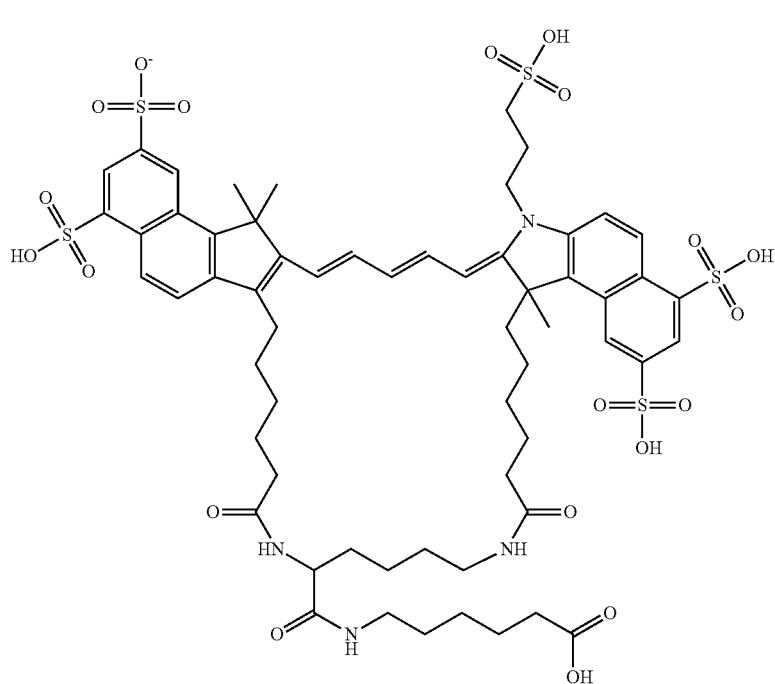

Compound 30

To a solution of Compound 29 (25 mg, 0.0225 mmol) and O—(N-succinimidyl)-N,N,N',N'-tetramethyluronium tetrafluoroborate (17 mg, 0.0562 mmol) in DMF (0.6 mL) is added triethylamine (0.03 mL) The mixture is stirred at room temperature for 1 h. The reaction mixture is poured into EtOAc (15 mL). The di-succinimidyl ester of Compound 29 is collected by centrifugation and washed with EtOAc (2×10 mL), EtOEt (1×10 mL) and dried under vacuum.

The above di-succinimidyl ester of Compound 29 is dissolved in water (50 mL) and a solution of Compound 9 (15 mg, 0.0450 mmol) in water (25 mL) [neutralized with $Na_2CO_3$ (4.8 mg, 0.0450 mmol)] is added slowly during the period of 30 minutes. The mixture is stirred at room temperature overnight. After removal of solvent, the residue is purified by preparative HPLC to give Compound 30 as blue powder (20 mg).

Example 31

Preparation of Compound 31

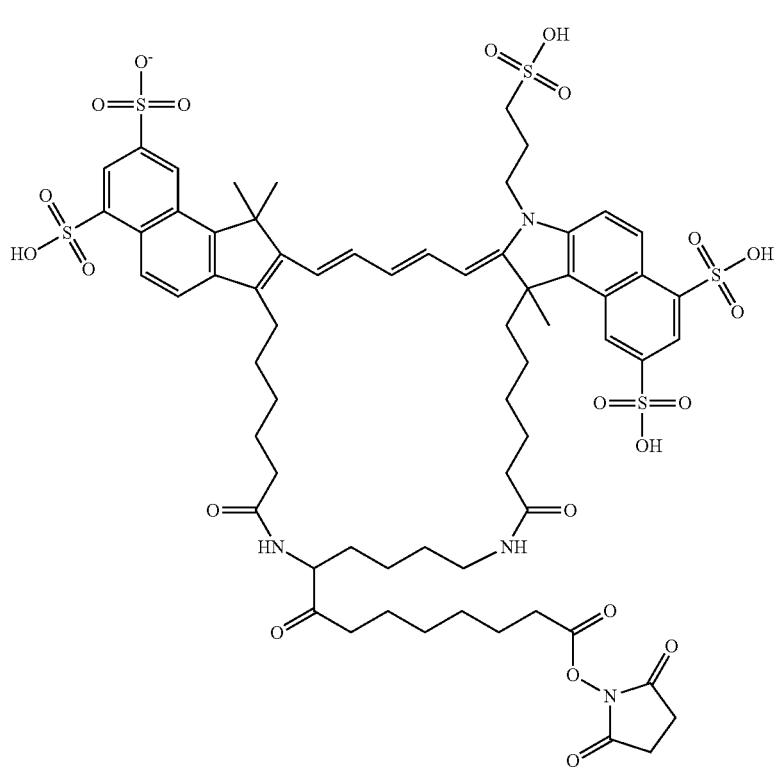

Compound 31

To a solution Compound 30 (10 mg, 0.0075 mmol) in DMF (0.4 mL) is added O—(N-succinimidyl)-N,N,N',N'-tetramethyluronium tetrafluoroborate (2.82 mg, 0.0094 mmol), followed by triethylamine (0.03 mL). The mixture is stirred at room temperature for 1 h. The solution is poured into EtOAc (15 mL). The solid is centrifuged and washed with EtOAc (3×10 mL), ether (1×10 mL) and dried under vacuum to give Compound 31 as bright blue powder (11 mg).

Example 32

Preparation of Compound 32

A solution of Compound 1 (353 mg, 1 mmol) and 2-chloro-1-formyl-3-(hydroxymethylene)-cyclohex-1-ene (173 mg, 1 mmol) in 1-butanol (48 mL) and benzene (12 mL) is heated to reflux for 2 h. After the reaction mixture is cooled to room temperature, a suspension of Compound 6 (462 mg, 1 mmol) in 1-butanol (7 mL) and benzene (3 mL) is added. The mixture is continued to reflux for 10 h with removal of water by a Dean-Stark condenser. After removal of solvent, the residue is purified by preparative HPLC to give Compound 32.

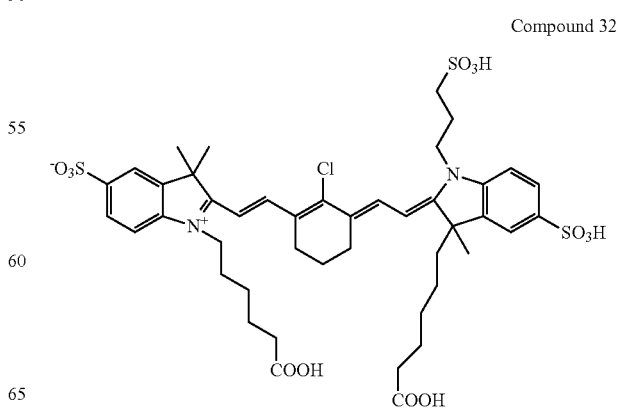

Compound 32

Example 33

Preparation of Compound 33

Compound 33

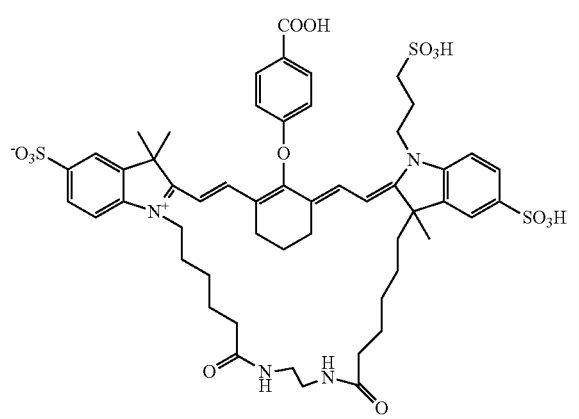

To a solution of Compound 32 (50.0 mg, 0.0574 mmol) and O—(N-succinimidyl)-N,N,N',N'-tetramethyluronium tetrafluoroborate (43 mg, 0.143 mmol) in DMF (1.0 mL) is added triethylamine (0.05 mL). The mixture is stirred at room temperature for 1 h. The resulting solution of di-succinimidyl ester of Compound 32 is diluted with DMF (50 mL), followed by addition of a solution of ethylenediamine (6.9 mg, 0.115 mmol) in DMF (30 mL) during the period of 30 minutes. The mixture is stirred at room temperature overnight. After removal of solvent, the chloro dye is converted to Compound 33 by 4-hydroxybenoic acid and-sodium hydride in DMF according to the procedure of N. Narayanan and G. Patonary (J. ORG. CHEM, 60, 2391 (1995)). Preparative HPLC purification gives pure Compound 33 (20 mg).

Example 34

Preparation of Compound 34

Compound 34

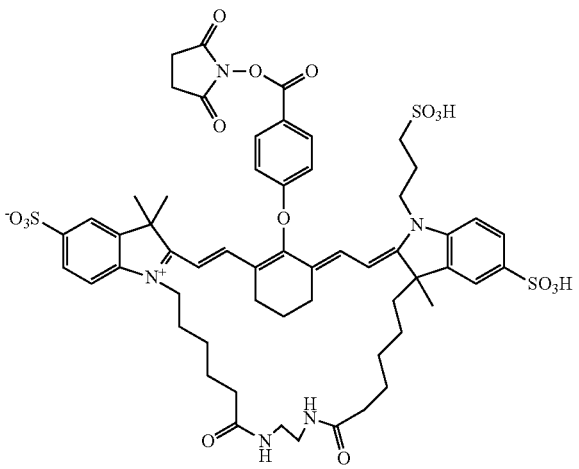

To a solution of Compound 33 (10.0 mg, 0.01 mmol) and O—(N-succinimidyl)-N,N,N',N'-tetramethyluronium tetrafluoroborate (8 mg, 0.05 mmol) in DMF (0.5 mL) is added triethylamine (5 µL). The mixture is stirred at room temperature for 1 h, and precipitated with ether to give the blue powder.

Example 35

Preparation of Compound 35

To Compound 20 in DMF is added 5 equivalents of anhydrous hydrazine. The mixture is stirred at ambient temperature for 15 minutes. The product is precipitated with 4 20 volumes of ethyl acetate and purified by HPLC.

Compound 35

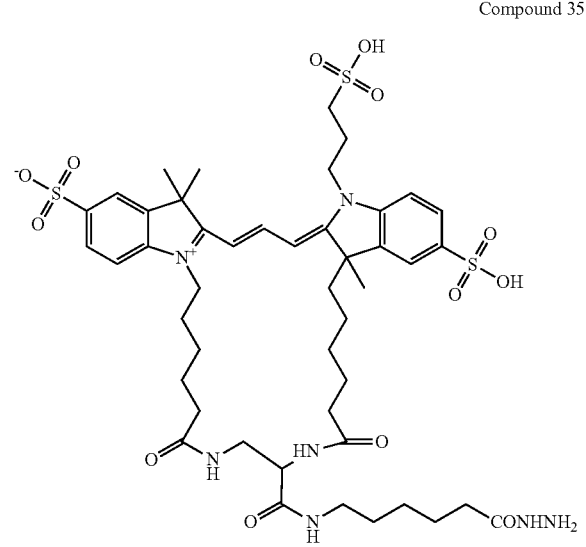

Example 36

Preparation of Compound 36

Compound 36

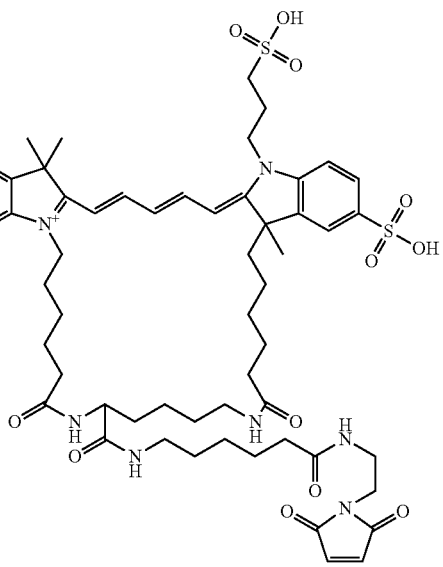

To Compound 14 in DMF at room temperature is added 4 equivalents of triethylamine and 1.2 equivalents of N-(2-aminoethyl)maleimide, trifluoroacetic acid salt. The mixture is stirred at ambient temperature for 15 minutes. The product is precipitated with 4 volumes of ethyl acetate and purified by HPLC.

Example 37

Preparation of Compound 37 (1,1'-Crosslinked Cyanine)

Compound 37 is prepared from Compound 9 by modification of WO 01/02374 (to R. Singh, et al.).

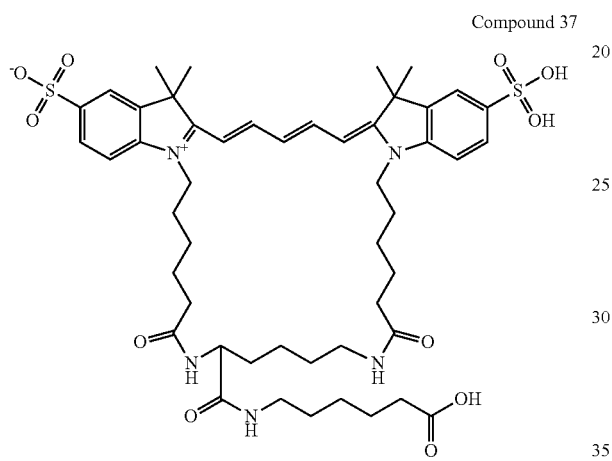

Compound 37

Example 38

Preparation of Compound 38 (1,1'-Crosslinked Cyanine, SE)

Compound 37 is converted to Compound 38 analogous to the procedure of Compound 14 as described in Example 14.

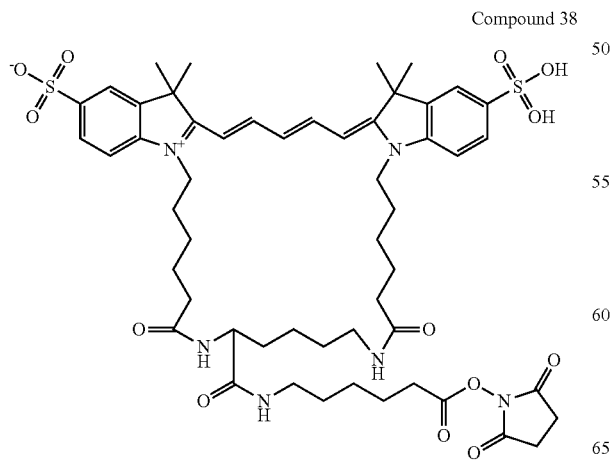

Compound 38

Example 39

Preparation of Compound 39

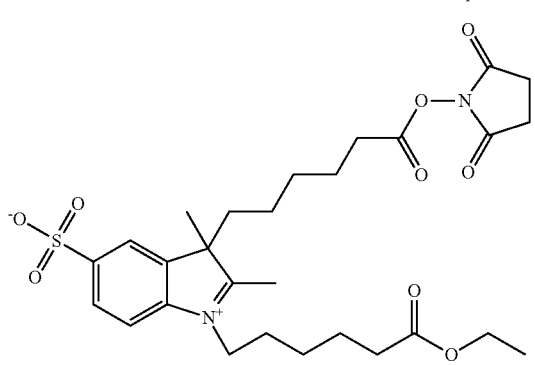

Compound 39

To a solution Compound 1 (5.0 g, 14.14 mmol) in DMF (20 mL) is added di(N-succinimidyl) carbonate (3.81 g, 14.85 mmol), followed by triethylamine (3.9 mL, 228.29 mmol). The mixture is stirred at room temperature for 1 h. The solution is poured into EtOAc (150 mL). The solid is centrifuged and washed with EtOAc (3×100 mL), ether 10 (1×100 mL) and dried under vacuum to give Compound 39, 6.0 g.

Example 40

Preparation of Compound 40

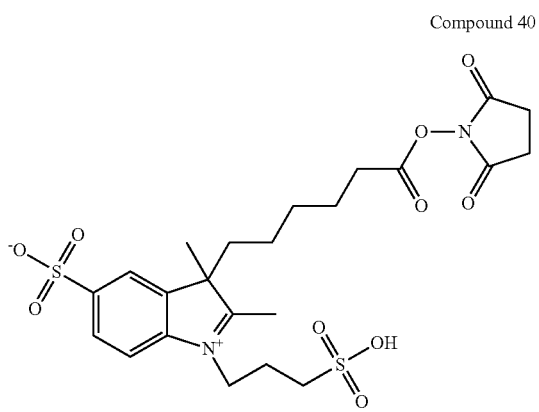

Compound 40

Compound 40 is prepared starting from Compound 6 analogously to the preparation of Compound 39.

Example 41

Preparation of Compound 41

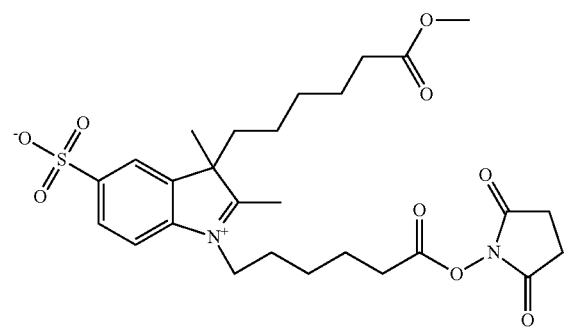

Compound 41

Compound is prepared starting from Compound 7 analogously to the preparation of Compound 39.

Example 42

Preparation of Compound 42

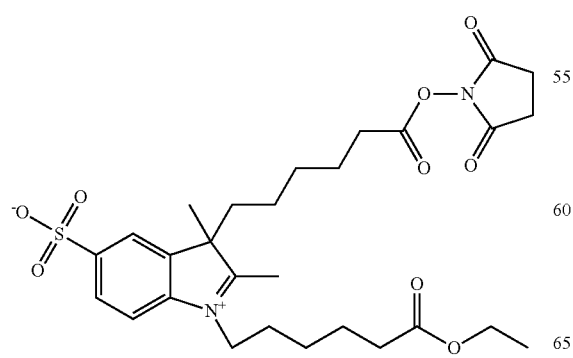

Compound 42

Compound 42 is prepared starting from Compound 8 analogously to the preparation of Compound 39.

Example 43

Preparation of Compound 43

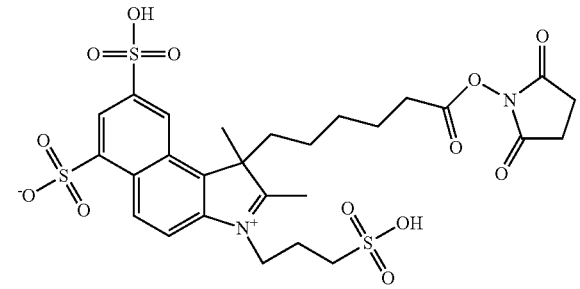

Compound 43

Compound 43 is prepared starting from Compound 27 analogously to the preparation of Compound 39.

Example 44

Preparation of Compound 44

Compound 44

Compound 44 is prepared starting form Compound 28 analogously to the preparation of Compound 39.

Example 45

Preparation of Compound 45

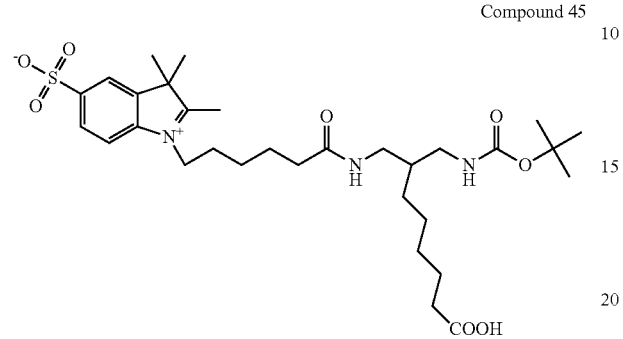
Compound 45

To a solution of Compound 39 (1.5 g, 3.33 mmol) in DMF (15 mL) is added and t-BuOCONHCH₂CH(CH₂CH₂CH₂CH9CH₂COOH)CH₂NH₂.HCl (product of AnaSpec, Inc.) (1.1 g, 3.33 mmol), followed by addition of triethylamine (0.34 g, 0.46 mL, 3.33 mmol). The reaction mixture is stirred at room temperature and the reaction is monitored by HPLC. After reaction is complete, the solvent is removed and the residue is used for the next reaction without further purification.

Example 46

Preparation of Compound 46

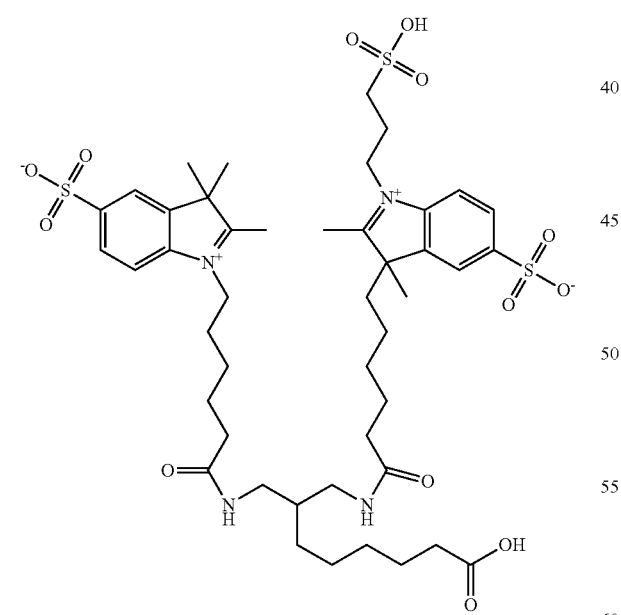
Compound 46

The above Compound 45 is dissolved in TFA (10 mL) at 0° C. and the solution is stirred at room temperature for 30 minutes. After removal of TFA, the residue is treated with ethyl ether. The solid is collected by filtration and washed with ether twice. After dried under vacuum, the solid is dissolved in DMF (15 mL) and the solution is neutralized with triethylamine. Then a solution of Compound 40 (1.86 g, 3.33 mmol) in DMF (10 mL) is added. The reaction mixture is stirred at room temperature. After the reaction is complete (monitored by HPLC), the solvent is removed and the residue is treated with ethyl acetate to give Compound 46.

Example 47

Preparation of Compound 47

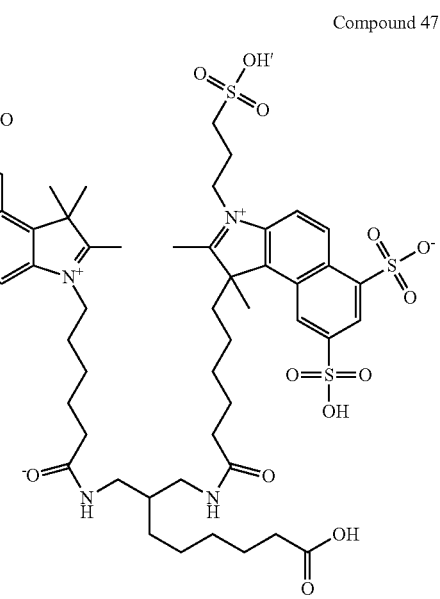
Compound 47

Compound 47 is prepared starting from Compound 43 and Compound 44 analogously to ther preparation of Compound 46.

Example 48

Preparation of Compound 48

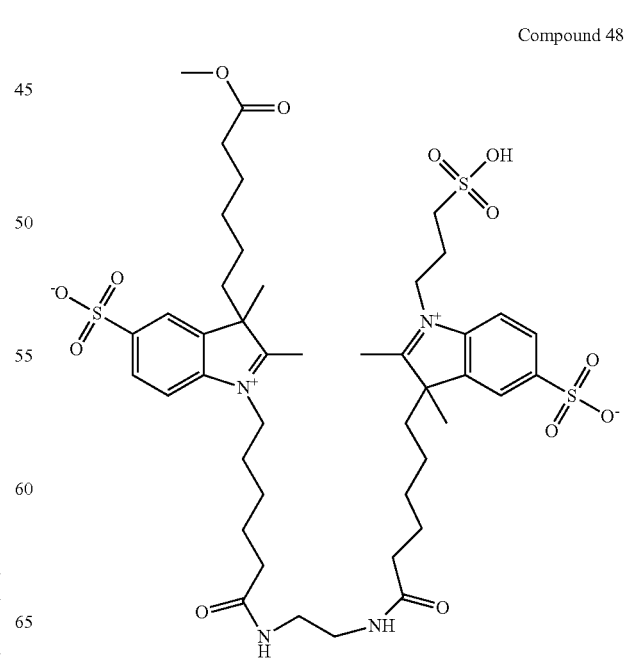
Compound 48

Compound 48 is prepared starting from Compound 40, BocNHCH₂CH₂NH₂ and Compound 41 analogously to the preparation of Compound 46.

Example 49

Preparation of Compound 49

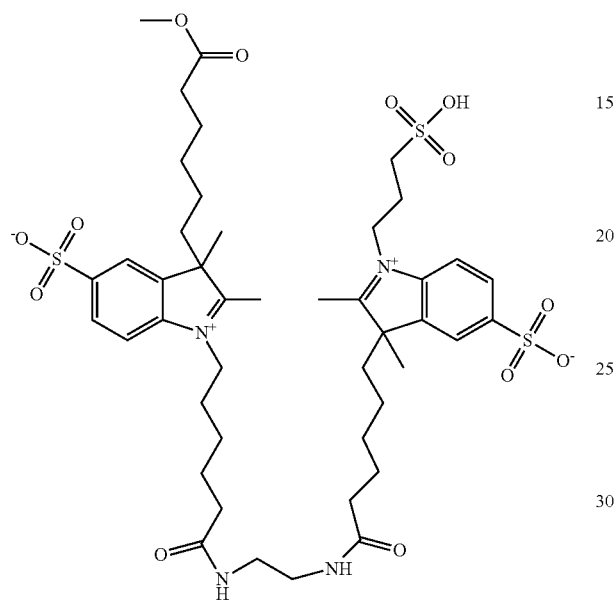

Compound 49 is prepared starting from Compound 39, BocNHCH2CH2NH2 and compound 42 analogously to the preparation of Compound 46.

Example 50

Preparation of Compound 50

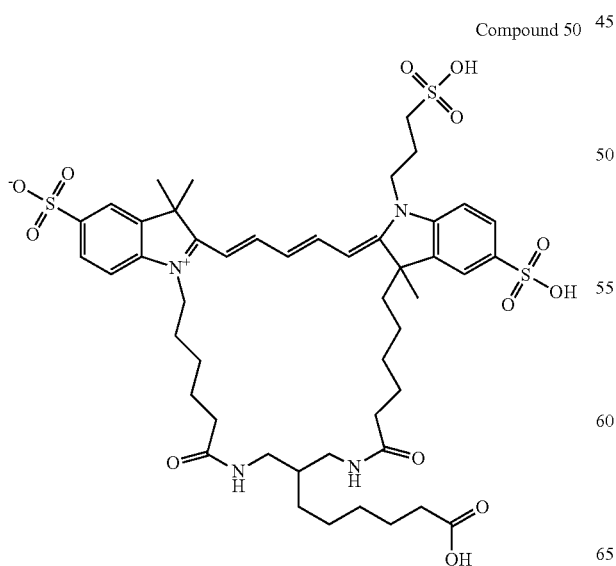

Compound 46 (500 mg, 0.517 mmol) and malonaldehyde bis(phenylimine) monohydrochloride (67 mg, 0.258 mmol) are dissolved in acetic anhydride (3 mL), followed by addition of pyridine (3 mL). The mixture is heated to 120° C. for 1 h. After cooling to room temperature, the mixture is dropped into ethyl acetate. The crude dye is collected by centrifugation and washed with ethyl acetate twice. Preparative HPLC purification gives Compound 50 as bright blue powder (200 mg).

Example 51

Preparation of Compound 51

Compound 51

Compound 46 (500 mg, 0.517 mmol) and N,N-diphenylformamidine (51 mg, 0.258 mmol) are dissolved in acetic anhydride (3 mL), followed by addition of pyridine (3 mL). The mixture is heated to 120° C. for 1 h. After cooling to room temperature, the mixture is dropped into ethyl acetate. The crude dye is collected by centrifugation and washed with ethyl acetate twice. Preparative HPLC purification gives Compound 51 (220 mg).

Example 52

Preparation of Compound 52

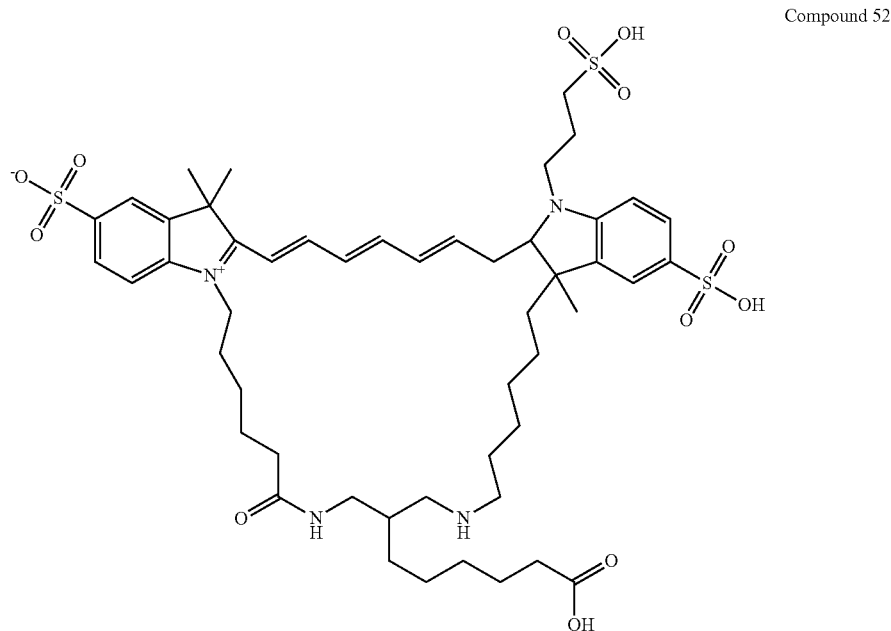

Compound 52

Compound 46 (500 mg, 0.517 mmol) and glutaconaldehyde dianil hydrochloride (74 mg, 0.258 mmol) are dissolved in acetic anhydride (3 mL), followed by-addition of pyridine (3 mL). The mixture is heated to 120° C. for 1 h. After Cooling to room temperature, the mixture is dropped into ethyl acetate. The crude dye is collected by centrifugation and washed with ethyl acetate twice. Preparative HPLC purification gives Compound 52 (190 mg).

Example 53

Preparation of Compound 53

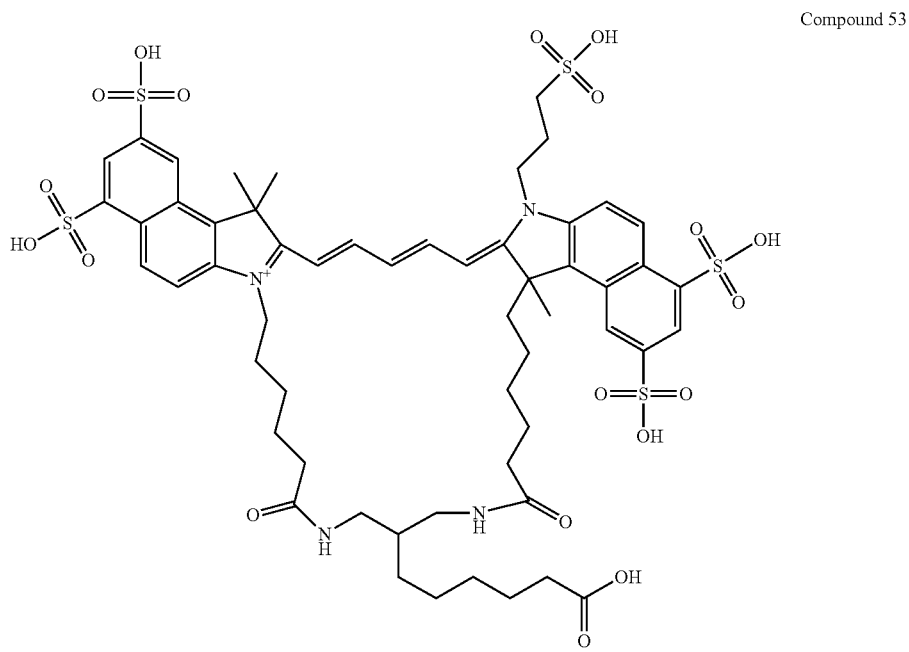

Compound 53

Compound 47 (500 mg, 0.407 mmol) and malonaldehyde bis(phenylimine) monohydrochloride (53 mg, 0.204 mmol) are dissolved in acetic anhydride (3 mL), followed by addition of pyridine (3 mL). The mixture is heated to 120° C. for 1 h. After cooling to room temperature, the mixture is dropped into ethyl acetate. The crude dye is collected by centrifugation and washed with ethyl acetate twice. Preparative HPLC purification gives Compound 53 as bright blue powder (180 mg).

Example 54

Preparation of Compound 54

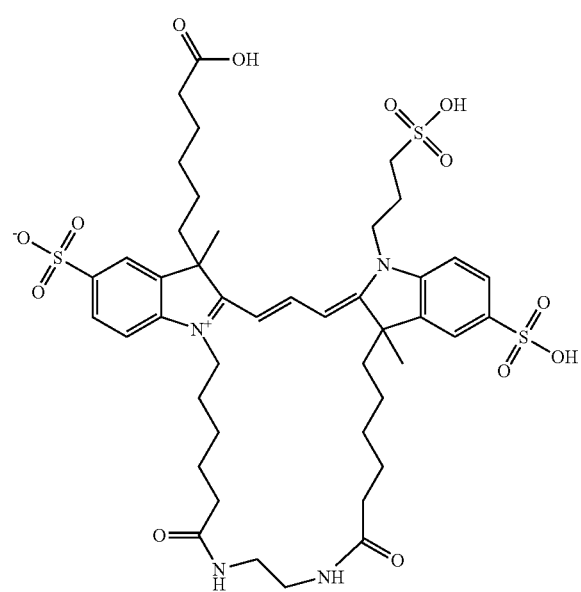

Compound 54

Compound 48 (500 mg, 0.525 mmol) and N,N-diphenyl-formamidine (51.5 mg, 0.262 mmol) are dissolved in acetic anhydride (3 mL), followed by addition of pyridine (3 mL). The mixture is heated to 120° C. for 1 h. After cooling to room temperature, the mixture is dropped into ethyl acetate. The crude dye is collected by centrifugation and washed with ethyl acetate twice and then dissolved in 1N NaOH (10 mL). After the hydrolysis reaction is completing (monitored by HPLC), the reaction mixture is diluted with water (10 mL) and neutralized with 1N HCl. Preparative HPLC purification gives Compound 54 (180 mg).

Example 55

Preparation of Compound 55

Compound 55

Compound 49 (500 mg, 0.582 mmol) and N,N-diphenyl-foiniamidine (57 mg, 0191 mmol) are dissolved in acetic anhydride (3 mL), followed by addition of pyridine (3 mL) The mixture is heated to 120° C. for 1 h. After cooling to room temperature, the mixture is dropped into ethyl acetate. The crude dye is collected by centrifugation and washed with ethyl acetate twice and then dissolved in 1N NaOH (10 mL). After the hydrolysis reaction is completing (monitored by HPLC), the reaction mixture is diluted with water (10 mL) and neutralized with 1N HCl. Preparative HPLC purification gives Compound 55 (180 mg).

Example 56

Preparation of a Peptide-Dye Conjugate

To aminophalloidin (3.5 mg, 4 mmol, Alexis Corp.) and the succinimidyl ester derivative Compound 14 (6.0 mg, 5 p.mol) in DMF is added N,N-diisopropylethylamine (2 pL, 11 μmol). The mixture is stirred at room temperature for 3 hours. To this solution is added 7 mL of diethyl ether. The solid is collected by centrifugation. The crude product is purified on SEPHADEX LH-20, eluting with water, followed by preparative HPLC to give the pure phaltoidin conjugate. The product is art effective stain for F-actin filaments in fixed-cell preparations.

Example 57

Preparation of a Drug-Dye Conjugate

A fluorescent dopamine ID, antagonist is prepared as follows: 10 mg of N-(p-aminophenethyl)spiperone (Amlalky, et al., FEBS LETT., 176, 436 (1984)), and 10 N,N-diisopropylethylamine in 1 mL of DMF is added 15 mg of Compound 14 or 20. After 3 hours, the reaction mixture is poured into 5 mL ether. The precipitate is centrifuged, then purified by chromatography on silica gel using 10-30% methanol in chloroform.

Example 58

Preparation of Protein-Dye Conjugates

A series of dye conjugates of goat anti-mouse IgG (GAM), goat anti-rabbit IgG (GAR), streptavidin, transferrin and other proteins, including R-phycoerythrin (R-PE) and allophycocyanin (APC) are prepared by standard means (Haugland, et al., METH. MOL. BIOL., 45, 205 (1995); Haugland, METH: MOL. BIOL., 45, 223 (1995); Haugland, METH. MOL. BIOL., 45,235 (1995); Haugland, CURRENT PROTOCOLS IN CELL BIOLOGY, 16.5.1-16.5.22 (2000)) using Compound 14 or 20 and a mono-succinimidyl ester derivative of the Cy5 dye (Amersham Biosciences).

The typical method for protein conjugation with succinimidyl esters of the invention is as follows. Variations in ratios of dye to protein, protein concentration, time, temperature, buffer composition and other variables that are well known in the art are possible that still yield useful conjugates. A solution of the protein is prepared at about 10 mg/mL in 0.1 M sodium bicarbonate. The labeling reagents are dissolved in a suitable solvent such as DMF or DMSO at about 10 mg/mL. Water is a suitable solvent for many dyes of the invention. Predetermined amounts of the labeling reagents are added to the protein solutions with stirring. A molar ratio of 10 equivalents of dye to 1 equivalent of protein is typical, though the optimal amount varies with the particular labeling reagent, the protein being labeled and the protein's concentration, and is determined empirically.

When optimizing the fluorescence yield and determining the effect of degree of substitution (DOS) on this brightness, it is typical to vary the ratio of reactive dye to protein over a several-fold range. The reaction mixture is incubated at room temperature for one hour or on ice for several hours. The dye-protein conjugate is typically separated from free unreacted reagent by size-exclusion chromatography, such as on Amersham PD-10 resin equilibrated with phosphate-buffered saline (PBS). The initial, protein-containing colored band is collected and the degree of substitution is determined from the absorbance at the absorbance maximum of each fluorophore, using the extinction coefficient of the free fluorophore. The dye-protein conjugate thus obtained can be subfractionated to yield conjugates with higher, lower or more uniform DOS.

Following is a specific example of using Compound 14 to prepare IgG-dye conjugate:

Step 1. Preparing protein solution (Solution A): Mix 50 µL of 1 M NaHCO$_3$ with 450 µL of IgG protein solution (4 mg/mL) to give 0.5 mL protein sample solution. The resulted solution should have pH 8.5±0.5.

Step 2. Preparing dye solution (Solution B): To 50 µL of DMSO add 1 mg of Compound 14, and stir until the compound is completely dissolved.

Step 3. Running conjugation reaction: Add the protein solution (A) to the dye solution (B) with effective stirring or shaking, and keep the reaction mixture stirred or shaken for 1-3 hrs.

Step 4. Purifying the conjugate:
a) Dilute 10× elution buffer with de-ionized water to give 1× elution buffer (Solution C) that is used to elute the protein conjugate from PD-10 column;

b) Load the column with the reaction mixture (from step 3, filtrated if necessary) or supernatant as soon as the liquid in the pre-packed column runs just below the top surface;

c) Add 1 mL of the IX elution buffer as soon as the sample runs just below the top resin surface; Repeat this 'sample washing' process twice; Add more IX elution buffer solution to elute the desired sample;

d) Collect the faster-running band that is usually the desired labeled protein. Keep the slower-running band that is usually free or hydrolyzed dye until the desired product is identified.

Step 5. Characterizing the desired dye-protein conjugate:
a). Measure OD (absorbance) at 280 nm and 650 nm (Note: for most spectrophotometers, the sample (from the column fractions) need be diluted with de-ionized water so that the OD values are in the range 0.1 to 0.9). The O.D. (absorbance) 280 nm is the maximum absorption of protein while 650 nm is the maximum absorption of Compound 14 amide (Note: to obtain accurate DOS, you must make sure that the conjugate is free of the non-conjugated dye); b). Calculating DOS using the following equation:

$$DOS=[dye]/[protein]=A650\times\epsilon_p/250000(A280-0.05A650)$$

[dye] is the dye concentration, and can be readily calculated from the Beer-Lambert Law: $A=s_{dye}CxL$; [protein] is the target protein concentration. This value can be either estimated by the weight (added to the reaction) if the conjugation efficiency is high enough (preferably >70%) or more accurately calculated by the Beer-Lambert Law: $A=\epsilon_{protein}CxL$. For example, IgG has the s value to be 203,000 cm$^{-1}$M$^{-1}$. For effective labeling, the degree of substitution should fall between 2-6 moles of Compound 14 to one mole of antibody.

Example 59

Fluorescent Labeling of Periodate-Oxidized Proteins

Two samples of 5 mg each of goat IgG antibody in 1 mL of 0.1 M acetate, 0.135 M NaCl, pH 5.5, are treated with 2.1 mg of sodium metaperiodate on ice, for 1 and 2 hours, respectively. The reactions are stopped by addition of 301.1 L ethylene glycol. The antibodies are purified on a Sephadex G25 column packed in PBS pH 7.2. One-tenth volume of 1 M sodium bicarbonate is added to raise the pH and Compound 35 is added at a molar ratio of dye to protein of 50:1. The reaction is stirred for 2 hours at room temperature. Sodium cyanoborohydride is added to a final concentration of 10 mM and the reaction is stirred for 4 hours at room temperature. The antibody conjugates are purified by dialysis and on Sephadex G25 columns as described above. Antibodies that are oxidized for 1 hour typically yield a degree of substitution of 1 mole of dye per mole of IgG. Antibodies that are oxidized for 2 hours typically yield a DOS of approximately 2 mole of dye per mole of IgG. Periodate-oxidized proteins in gels and on blots can also be labeled, essentially as described in Estep T N and Miller T J, (ANAL. BIOCHEM., 157, 100-105 (1986)). The conjugates of Compound 35 exhibit greater fluorescence than the conjugates of Cy3 dye at similar DOS when conjugated to a wide variety of proteins.

Example 60

Labeling Beta-Galactosidase with a Thiol-Reactive Dye

A solution of beta-galactosidase, a protein rich in free thiol groups, is prepared in PBS (2.0 mg in 400 µL). The protein solution is then treated with a 20 mg/L solution of the maleimide derivative Compound 36 in DMF. Unreacted dye is removed on a spin column. The degree of substitution by the dye is estimated using the extinction coefficient of the free dye as described in Example 58. The protein concentration is estimated from the absorbance at 280 nm, corrected for the absorbance of Compound 36 at that wavelength.

Example 61

Total Fluorescence of Selected Dye Protein Conjugates Compared with Cy5

In general, the higher the DOS, the brighter the Compounds 14 and 17 bioconjugates relative to the Cy5 bioconjugates, although, Compound 14 and 17 bioconjugates are brighter at all DOS tested. The decrease in the RQY of the Cy5 bioconjugates is found to be accompanied by an increase in the 600-nm absorbance band relative to the 650-nm absorbance band. The increase in extinction of the 600 nm band is always associated with a large quenching of the fluorescence. This result is completely supportive of the work of Gruber, et al. (BIOCONJUGATE CHEM., 11, 696 (2000)) who observed a similar correlation of an increased absorbance at 600 nm and a large decrease in fluorescence intensity. FIG. 4 shows a direct comparison of the fluorescence emission of the Compound 14 conjugate of GAR IgG at nearly equivalent DOS. The 600 nm absorbance band is always much lower in extinction for Compound 14 than for an equivalently labeled Cy5 derivative. This general observation has now been confirmed with several other proteins.

Example 62

Comparison of the Protein Conjugates Prepared from 1,1'-Crosslinked and Non-Crosslinked "Cy5-Like" Isomers with Compound 14

1,1'-Crosslinked Cy5 isomer is synthesized as described in Example 37 and conjugated to GAR at various DOS. FIG. 4 is a direct comparison of fluorescence properties of GAR conjugates prepared from Cy5 SE, Compounds 14 and 38. One can see that the 1,3'-intramolecular crosslinking has resulted in a drastic improvement of fluorescence performance of Compound 14 GAR conjugates over those of Cy5 (non-crosslinked cyanine) and Compound 38 (1,1'-crosslinked cyanine). Compound 14 GAR conjugate also has much weaker absorbance around 600 nm (non-fluorescent excitation). The brighter fluorescence emission of compound 14 GAR conjugate (than Cy5 and Compound 38) is observed at all of the tested DOS's.

Example 63

Comparison of the Fluorescence of goat Anti-Mouse IgG (GAM)

Conjugates of Cy3 and Compound 20 are prepared analogously to the procedure of Example 58 with Compound 20 and the Cy3 reactive dyes at a variety of degrees of substitution ranging from 1.0-12. The conjugates are characterized using excitation wavelength=532 nm analogously to Example 58.

Example 64

The Photostability of Compound 13 is Greater than that of Cy5 Free Acid

Figure 5:
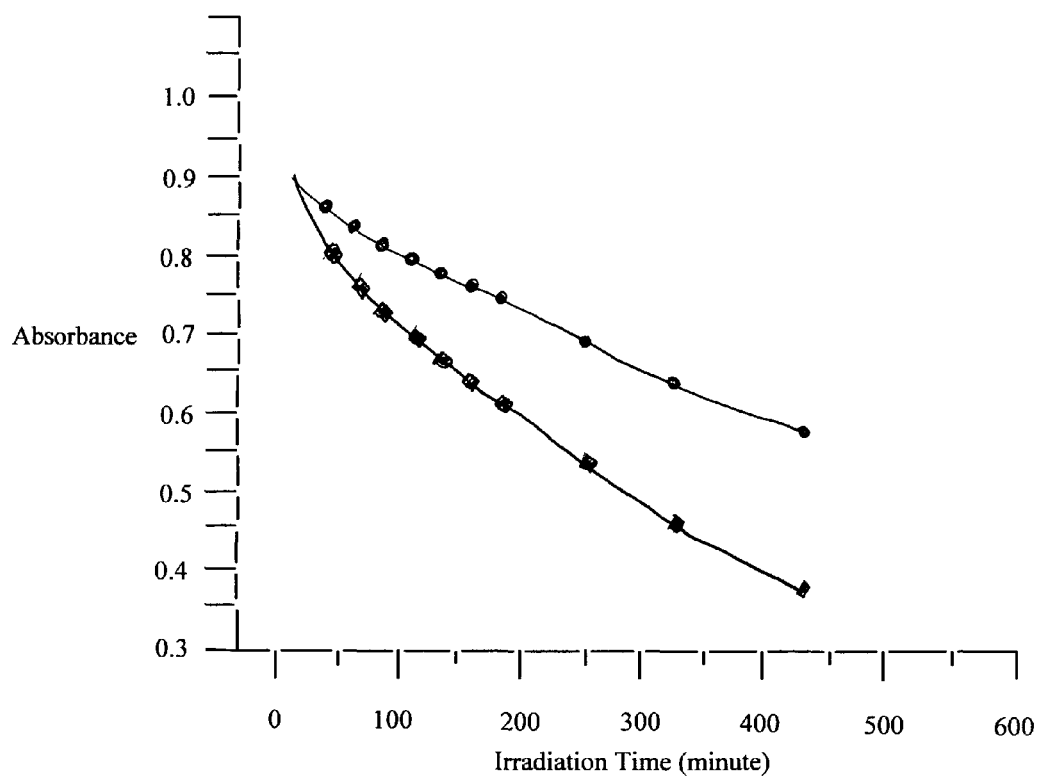
FIG. 5. Photostability comparison of Compound 13 (solid circles) with Cy5 free acid (squares) in PBS buffer (pH 7.4). The detailed experimental conditions are described in Example 64.

Photobleaching experiments are performed at 0.111M concentrations of Compound 13 and commercially available Cy5 free acid. Both of the compounds are irradiated with A100 W Mercury lamp in PBS (pH 7.0), where both of the dyes receive the same amount of irradiation as determined by photometric measurements. As shown in FIG. 5, Compound 13 remains about 3 times brighter than the Cy5 free acid after 500 minutes of illumination.

Example 65

Fluorescence Energy Transfer in Conjugates of R-Phycoerythrin and Allophycocyanin R-phycoerythrin (R-PE) conjugate of Compound 14 or 17 is prepared as in Example 58 with a DOS sufficiently high to quench the donor fluorescence almost completely (DOS about 4-8). The resulting phycobiliprotein conjugate is excited at 488 um and the fluorescence emission is compared to that of unmodified R-phycoerythrin excited at the same wavelength. Highly efficient energy transfer (>99%) occurs from the protein to the fluorescent dye. A conjugate of these complexes with streptavidin is prepared essentially as described by Haugland (METH. MOL. BIOL., 45, 205 (1995)). This streptavidin conjugate retains the energy transfer properties and is useful for cell staining in flow cytometers that utilize the argon-ion laser for excitation. Tandem conjugates of allophycocyanin can also be made, with longer wavelength dyes of the invention such as Compound 34 yield emission well beyond 700 um when excited near 633 um.

Example 66

Labeling of Actin in Cultured Mammalian Cells

Bovine pulmonary artery cells (BPAEC) are grown to 30-50% of confluence on glass. The cells are fixed with 3.7% formaldehyde, permeabilized with 0.2% Triton X-100, and blocked with 6% BSA. The cells are incubated with the phalloidin dye-conjugate of Example 56. The cells are rinsed with blocking buffer and mounted in PBS pH 7.4. The stained cells display actin filaments decorated with red fluorescence.

Example 67

Preparation and Use of a Fluorescent Alpha-Bungarotoxin Dye-Conjugate

Alpha-Bungarotoxin (1 mg) in 25 μL, 0.1 M NaHCO$_3$ is treated with 1.5 equivalents of Compound 14 or 20 at room temperature for 2 hours. The product is purified by size exclusion, by ion exchange chromatography, and finally by reverse-phase HPLC. The conjugate is used for staining of acetylcholine receptors.

Example 68

Preparation and Use of a Fluorescent Tyramide

A 2-fold molar excess of tyramine hydrochloride is added to Compound 20 in aqueous solution at room temperature followed by an excess of triethylamine. After 30 minutes the red solid is precipitated with acetone, washed with ether and purified by preparative HPLC. Bovine pulmonary artery cells (BPAEC) are grown to 30-50% of confluence on glass. The cells are fixed with 3.7% formaldehyde, permeabilized with 0.2% Triton X100, and blocked with 1 mg/mL streptavidin and 1 mM biotin. After washing, cells are exposed to about 0.05 p.g/mL of biotinylated anti-cytochrome C oxidase (anti-COX) then incubated with Streptavidin-HRP conjugate at room temperature. Cells are rinsed again. The sample is then incubated with Compound 20 tyramide and examined using fluorescence microscopy.

Example 69

Preparation of Aminodextran Dye-Conjugates 70,000 MW aminodextran (50 mg) derivatized with an average of 13 amino groups is dissolved at 10 mg/mt, in 0.1 M $NaHCO_3$. Compound 14 or 20 or 31 is added so as to give a dye/dextran ratio of about 10-15. After 6-12 hours the conjugate is purified on SEPHADEX G-50, eluting with water. Typically 4-6 moles of dye are conjugated to 70,000 MW dextran.

Example 70

Preparation of Fluorescent-Dye Labeled Microspheres

Uniform microspheres are chemically modified to have functional groups such as amino or carboxyl or aldehydes. These functionalized microspheres are covalently conjugated with the corresponding reactive dyes as listed in Table 1. For example, the amine-modified microspheres are readily conjugated to the dyes of the invention through succinimidyl esters such as Compounds 14, 17, 20 and 31. A dye-labeled protein is covalently coupled through its amine residues to the carboxylate groups of the polymer using ethyl 3-(dimethylaminopropyl)carbodiimide (EDAC).

The dyes of invention can also be physically adsorbed on microspheres. For example, carboxylate-modified microspheres are suspended in a solution of a protein that has been conjugated to a dye of the invention. The protein is passively adsorbed on the microspheres, and excess protein is removed by centrifugation and washing. Microparticles of a size that cannot be centrifuged are separated from excess protein by dialysis through a semi-permeable membrane with a high MW cutoff or by gel filtration chromatography. Another example is that biotinylated microspheres are treated with a streptavidin, avidin or anti-biotin conjugate of a dye of the invention.

Example 71

Preparation of Fluorescent Liposoines Using Dyes of the Invention

Selected dyes of the invention (such as Compound 13 and 19) are sufficiently water soluble to be incorporated into the interior of liposomes by methods well known in the art (S. BIOL. CHEM., 257, 13892 (1982) and PROC. NATL. ACAD. SCI., USA 75, 4194 (1978)). Alternatively, liposomes containing dyes of the invention having a lipophilic substituent (e.g. alkyl having 11-22 carbons), within their membranes are prepared by co-dissolving the fluorescent lipid and the unlabeled lipids. hospholipid(s) that make up the liposome before forming the liposome dispersion essentially as described by Szoka Jr., et al. (ANN. REV. BIOPHYS. BIOENG., 9, 467 (1980)).

Example 72

Preparation of Dye-Bacteria Conjugates

Heat-killed *Escherichia coli* are suspended at 10 mg/mL in pH 8-9 buffer then incubated with 0.5-1.0 mg/mL of an amine-reactive dye, typically a succinimidyl ester derivative (such as Compound 14 or 20 or 31). After 30-60 minutes the labeled bacteria are centrifuged and washed several times with buffer to remove any unconjugated dye. Labeled bacteria is analyzed by flow cytometry.

Example 73

Preparation of Nucleotide-Dye Conjugates

To 2 mg of 5-(3-aminoallyl)-2'-deoxyuridine 5'-triphosphate (Sigma Chemical) in 100 μL water is added Compound 14 or 20 in 100 μL DMF and 5 μl, triethylamine. After 3 hours, the solution is evaporated and the residue is purified by HPLC. The product fractions are lyophilized to give the red-fluorescent nucleotide conjugate. Alternatively, fluorescent dye-conjugates of deoxyuridine 5'-triphosphate are prepared from 5-(3-amino-1-propynyl)-2'-deoxyuridine 5'-triphosphate, or by treating a thiolated nucleotide or a thiophosphate nucleotide with a thiol-reactive dye of the invention (such as the maleimide Compound 36). Additionally, 2'-(or 3')-2-aminoethylaminocarbonyladenosine 5'-triphosphate is reacted with a slight excess of Compound 14 and, following precipitation with ethanol, the ribose-modified product is purified by preparative HPLC. Additional nucleotides conjugated with the dyes of invention can be readily prepared by someone skilled in the art following the published procedures such as Nimmakayalu M, et al., BIOTECHNIQUES, 28, 518-522 (2000); Muhlegger K, et al., BIOL. CHEM. HOPPE SEYLER, 371, 953-965 (1990); Giaid A, et al. HISTOCHEMISTRY, 93, 191-196 (1989)., Example 74

Preparation of an Oligonucleotide Dye-Conjugate

A 5'-amine-modified, 18-base M13 primer sequence (about 100 μL is dissolved in 4 μL water. To this is added 250 μg of Compound 14 or 20 in 100 μL 0.1 M sodium borate, pH 8.5. After 16 hours, 10 μL of 5 M NaCl and 3 volumes of cold ethanol are added. The mixture is cooled to −20° C., centrifuged, the supernatant is decanted the pellet is rinsed with ethanol and then dissolved in 100 μL water. The labeled oligonucleotide is purified by HPLC. The desired peak is collected and evaporated to give the fluorescent oligonucleotide.

Example 75

In Situ Hybridization of an RNA Probe

Mouse fibroblasts are fixed and prepared for mRNA in situ hybridization using standard procedures. A dye-labeled RNA probe is prepared by in vitro transcription of a plasmid containing the mouse actin structural gene cloned downstream of a phage T3 RNA polymerase promoter. Labeling reactions comprise combining 2 μL DNA template (1 μg DNA), 1 μL each of 10 mM ATP, CTP and GTP, 0.75 µL 10 mM UTP, 2.5 µL 1 mM aminoallyl-labeled UTP, 2 µL 10× transcription buffer (400 mM Tris, pH 8.0, 100 mM MgCl$_2$, 20 mM spermidine, 100 mM NaCl), 1 µLT3 RNA polymerase (40 units/µL), 1 µL 2 mg/mL BSA, and 8.75 µL water. Reactions are incubated at 37° C. for two hours. The DNA template is removed by treatment with 20 units DNase I for 15 minutes, at 37° C. The RNA transcript is purified by extraction with an equal volume of phenol:chloroform, 1:1, then by chromatography on SEPHADEX G50. Labeled RNA is denatured for 5 minutes at 50° C., then hybridized to cellular preparations using standard procedures. The long-wavelength fluorescence of the labeled cells is detected by excitation through an optical filter optimized for Cy5-like dyes.

Example 76

Preparing DNA Hybridisation Probes Using Amine-Modified DNA and an Amine-Reactive Dye of the Invention Nick translation is performed using pUC 1.77 plasmid DNA containing a chromosome 1 human alpha-satellite probe. To a microcentrifuge tube is added, in the following order: 23.5 µL water, 5 µL 10× Nick Translation buffer (0.5 M Tris-HCl, 50 mM MgCl$_2$, 0.5 mg/mL BSA, pH 7.8), 5 µL, 0.1 M DTT, 4 µL d(GAC)TP mix (0.5 mM dATP, 0.5 mM dCTP, 0.5 mM dGTP), 1 µL 0.5 mM-dTTP, 4 µL 0:5 mM aminoallyl-dUTP, 1 µL 1 µg/µL template DNA, 5 µL DNase I (1 µg/mL, 2000 Kunitz units/mg), 1.5 µL DNA polymerase I (10 U/µL). The tube is incubated 2 hours at 15° C., then brought to a final volume of 100 µL with water. The amine-modified DNA is purified using a QIAQUICK PCR purification Kit (Qiagen). The amine-modified DNA is resuspended in 5 µL water. To the solution is added 3 µL 25 mg/mL sodium bicarbonate and 50 µg of Compound 14 or 20 in 5 µL DMF. The reaction is incubated for 1 hour at room temperature in the dark, to the reaction is added 90 µL water, and it is purified using a QIAQUICK PCR purification kit (Qiagen). The labeled DNA products are suitable for in situ hybridization experiments, use on microarrays and as fluorescence donors or acceptors in hybridization-based assays.

Example 77

Staining Cells with Tandem Dye-Labeled Streptavidin

Jurkat cells are washed twice with 1% BSA/PBS and resuspended at a concentration of 1×10$^7$ cells/mL. The Jurkat cells are then incubated on ice for 60 minutes with mouse anti human CD4 biotin (Biosource International) at the recommended concentration of 10 µL for 1×10$^6$ cells. After incubation with the primary antibody, the cells are washed with 1% BSA/PBS and incubated on ice for 30 minutes with 1 µg of either the fluorescent streptavidin-phycoerythrin conjugate of Example 58, or a streptavidin conjugate of GII3CO'S RED 670. The cells are washed with 1% BSA/PBS, centrifuged, and resuspended with 400 µL of 1% BSA/PBS. The samples are analyzed on a FacsVantage flow cytometer exciting with the 488-nm line of an argon laser, collecting the emission by a 700-nm long pass filter (XF-48). Using a FSC versus SSC dot plot the live cells are gated and the geometric mean of the fluorescence for FL3 is measured. The data is analyzed for both fluorescence and signal/noise ratio.

The invention claimed is:

1. A kit for fluorometric analysis of a biological sample, comprising: a dye solution comprising a conjugate of a biological substance and dye I,

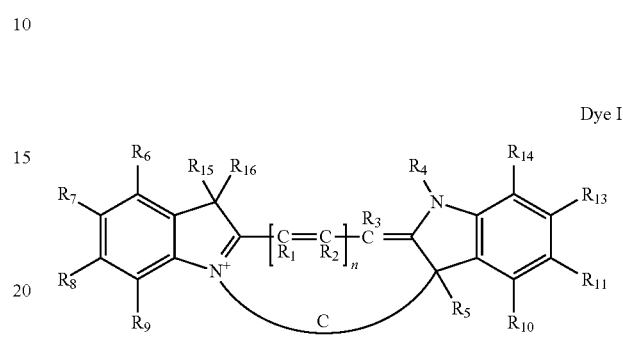

Dye I wherein C is a non-conjugated chain of 10 to 50 linear atoms selected from a group consisting of carbon and nitrogen that are further substituted by substituents selected from a group consisting of hydrogen, alkyl having 1-20 carbons, hydroxyl, carbonyl, and RGM;

n is 0, 1, 2 or 3;

$R_1$, $R_2$ and $R_3$ are independently a hydrogen having 1-20 carbons, a cycloalkyl having 3-20 carbons, an aryl, a heteroaryl, an amino, an alkylamino, an arylamino, a thiol, an alkylthio or a RGM;

$R_4$-$R_{11}$ and $R_{13}$-$R_{16}$ are independently a hydrogen, an alkyl having 1-20 carbons, a hydroxyl, an alkoxy having 1-20 carbons, a fluorinated alkyl, a halogen, an alkylthiol, a sulfonyl, a carbonyl, a hydroxyl, an amino, an alkylthio, a thiol, a sulfate, a phosphonate or a RGM;

RGM is a carboxylic acid, an activated ester of a carboxylic acid, an acyl azide, an acyl nitrile, an imido ester, an isocyanate, an isothiocyanate, or a maleimide;

wherein the biological substance is selected from a group consisting of a peptide, protein, nucleotide, nucleic acid, carbohydrate, lipid, membrane or cell.

2. The kit according to claim 1, wherein RGM is an activated ester of a carboxylic acid, an imido ester, or a maleimide.

3. The kit according to claim 1, wherein $R_{15}$ and $R_{16}$ are an alkyl having 1-20 carbons.

4. The kit according to claim 1, wherein C is a non-conjugated chain of 10 to 50 linear atoms selected from a group consisting of carbon and nitrogen that are further substituted by substituents selected from a group consisting of hydrogen, carbonyl, and RGM.

5. The kit according to claim 1, wherein the biological substance is a nucleotide or a nucleic acid.

6. A kit for fluorometric analysis of a biological sample, comprising: a dye solution comprising a conjugate of a biological substance and dye II, Dye II

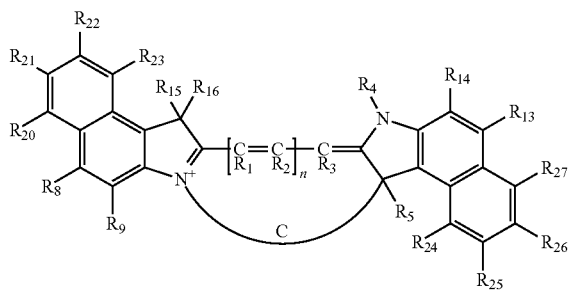

wherein C is a non-conjugated chain of 10 to 50 linear atoms selected from a group consisting of carbon and nitrogen that are further substituted by substituents selected from a group consisting of hydrogen, alkyl having 1-20 carbons, hydroxyl, carbonyl, and RGM;

n is 0, 1, 2 or 3;

$R_1$, $R_2$ and $R_3$ are independently a hydrogen, an alkyl having 1-20 carbons, a cycloalkyl having 3-20 carbons, an aryl, a heteroaryl, an amino, an alkylamino, an arylamino, a thiol, an alkylthio or a RGM;

$R_4$-$R_5$, $R_8$-$R_9$, $R_{15}$-$R_{16}$ and $R_{20}$-$R_{27}$ are independently a hydrogen, an alkyl having 1-20 carbons, a hydroxyl, an alkoxy having 1-20 carbons, a fluorinated alkyl, a halogen, an alkylthiol, a sulfonyl, a carbonyl, a hydroxyl, an amino, an alkylthiol, a thiol, a sulfate, a phosphonate or a RGM;

RGM is a carboxylic acid, an activated ester of a carboxylic acid, an acyl azide, an acyl nitrile, an imido ester, an isocyanate, an isothiocyanate, or a maleimide;

wherein the biological substance is selected from a group consisting of a peptide, protein, nucleotide, nucleic acid, carbohydrate, lipid, membrane or cell.

7. The kit according to claim 6, wherein RGM is an activated ester of a carboxylic acid, an imido ester, or a maleimide.

8. The kit according to claim 6, wherein $R_{15}$ and $R_{16}$ are an alkyl having 1-20 carbons.

9. The kit according to claim 6, wherein C is a non-conjugated chain of 10 to 50 linear atoms selected from a group consisting of carbon and nitrogen that are further substituted by substituents selected from a group consisting of hydrogen, carbonyl, and RGM.

10. The kit according to claim 1, wherein the biological substance is a nucleotide or a nucleic acid.

* * * * *